US012643939B2

(12) United States Patent
Khanna et al.

(10) Patent No.:  US 12,643,939 B2
(45) Date of Patent:  Jun. 2, 2026

(54) ANTIBODY TO EPSTEIN BARR VIRUS AND USES THEREOF

(71) Applicant: The Council of the Queensland Institute of Medical Research, Herston (AU)

(72) Inventors: Rajiv Khanna, Herston (AU); Kristine Hua, Herston (AU)

(73) Assignee: The Council of the Queensland Institute of Medical Research, Herston (AU)

( * ) Notice: Subject to any disclaimer, the term of this patent is extended or adjusted under 35 U.S.C. 154(b) by 187 days.

(21) Appl. No.: 16/638,125

(22) PCT Filed: Aug. 10, 2018

(86) PCT No.: PCT/AU2018/050851
§ 371 (c)(1),
(2) Date: Feb. 10, 2020

(87) PCT Pub. No.: WO2019/028530
PCT Pub. Date: Feb. 14, 2019

(65) Prior Publication Data
US 2020/0255499 A1     Aug. 13, 2020

(30) Foreign Application Priority Data
Aug. 10, 2017     (AU) ................................. 2017903197

(51) Int. Cl.
| | |
|---|---|
| *C07K 16/08* | (2006.01) |
| *C07K 16/085* | (2026.01) |
| *G01N 33/569* | (2006.01) |
| *A61K 39/00* | (2006.01) |

(52) U.S. Cl.
CPC ..... *C07K 16/085* (2013.01); *G01N 33/56994* (2013.01); *A61K 2039/505* (2013.01); *C07K 2317/24* (2013.01); *C07K 2317/56* (2013.01); *C07K 2317/76* (2013.01); *C07K 2317/92* (2013.01); *G01N 2333/05* (2013.01); *G01N 2500/10* (2013.01)

(58) Field of Classification Search
None
See application file for complete search history.

(56) References Cited

U.S. PATENT DOCUMENTS

| | | | | |
|---|---|---|---|---|
| 6,180,370 B1 * | 1/2001 | Queen | ...................... | A61P 19/02 |
| | | | | 435/69.6 |
| 9,376,485 B2 * | 6/2016 | Wang | ...................... | A61P 37/02 |

FOREIGN PATENT DOCUMENTS

| | | | | |
|---|---|---|---|---|
| WO | WO-2013130565 A1 * | 9/2013 | .............. | A61P 31/22 |
| WO | WO 2015/117244 A1 | 8/2015 | | |

OTHER PUBLICATIONS

Stryer, Biochemistry 4th, WH Freeman, New York. 1995 (Year: 1995).*
Colman, Peter M. Research in Immunology 145.1 (1994): 33-36 (Year: 1994).*
Haque, Tanzina, et al. "A mouse monoclonal antibody against Epstein-Barr virus envelope glycoprotein 350 prevents infection both in vitro and in vivo." The Journal of infectious diseases 194.5 (2006): 584-587. (Year: 2006).*
Islas-Ohlmayer, Miguel et al. "Experimental infection of NOD/SCID mice reconstituted with human CD34+ cells with Epstein-Barr virus." Journal of virology vol. 78,24 (2004): 13891-900. doi:10.1128/JVI.78.24.13891-13900.2004 (Year: 2004).*
Kleiveland CR. Peripheral Blood Mononuclear Cells. In: Verhoeckx K, Cotter P, López-Expósito I, et al., editors. The Impact of Food Bioactives on Health: in vitro and ex vivo models [Internet]. Cham (CH): Springer; 2015. Chapter 15. (Year: 2015).*
Kipriyanov, Sergey M., and Fabrice Le Gall. "Generation and production of engineered antibodies." Molecular biotechnology 26.1 (2004): 39-60. (Year: 2004).*
Janeway, Charles A. "Immunobiology: The Immune System in Health and Disease." 2001 (Year: 2001).*
Haque, T. et al., "A Mouse Monoclonal Antibody against Epstein-Barr Virus Envelope Glycoprotein 350 Prevents Infection Both In Vitro and In Vivo," Journal of Infectious Diseases, vol. 194; 584-587 (2006).
Notification of Transmittal of the International Search Report and the Written Opinion for International Application No. PCT/AU2018/050851, titled: "Antibody to Epstein Barr Virus and Uses Thereof," mailed: Oct. 31, 2018.
Notification of Transmittal of International Preliminary Report on Patentability for International Application No. PCT/AU2018/050851, titled: "Antibody to Epstein Barr Virus and Uses Thereof," mailed: Dec. 5, 2019.
Coghill, A. E. and A. Hildesheim, "Epstein-Barr Virus Antibodies and the Risk of Associated Malignancies: Review of the Literature." American Journal of Epidemiology, vol. 180; No. 7; 687-695 (2014).
Gu, S. Y. et al., "First EBV vaccine trial in humans using recombinant vaccinia virus expressing the major membrane antigen." Dev Biol Stand, vol. 84; 171-177 (1995). (Abstract Only).
Moutschen, M. et al., "Phase I/II studies to evaluate safety and immunogenicity of a recombinant gp350 Epstein-Barr virus vaccine in healthy adults." Vaccine, vol. 25; No. 24; 4697-4705 (2007).
Sashihara, J. et al., "Soluble rhesus lymphocryptovirus gp350 protects against infection and reduces viral loads in animals that become infected with virus after challenge." PLoS Pathog, vol. 7; No. 10; c1002308 (2011).
Szakonyi, G. et al., "Structure of the Epstein-Barr virus major envelope glycoprotein." Nat Struct Mol Biol, vol. 13; No. 11; 996-1001 (2006).

(Continued)

*Primary Examiner* — Michael Szperka
*Assistant Examiner* — Lia E Taylor
(74) *Attorney, Agent, or Firm* — Hamilton, Brook, Smith & Reynolds, P.C.

(57) ABSTRACT

A recombinant, humanized antibody or antibody fragment that is capable of at least partly preventing or inhibiting Epstein Barr Virus gp350 binding to a human cell. The antibody may be useful for passively immunizing humans against Epstein Barr Virus and/or treating or preventing Epstein Barr Virus-associated diseases, disorders or conditions. The antibody or antibody fragment may also be used to detect Epstein Barr Virus.

15 Claims, 15 Drawing Sheets

Specification includes a Sequence Listing.

(56) References Cited

OTHER PUBLICATIONS

Tanner, J.E. et al., "Peptides Designed to Spatially Depict the Epstein-Barr Virus Major Virion Glycoprotein gp350 Neutralization Epitope Elicit Antibodies That Block Virus-Neutralizing Antibody 72A1 Interaction with the Native gp350 Molecule," Journal of Virology, vol. 89; No. 9; 4932-4941 (2015).

Weiss, E.R. et al., "High Epstein-Barr Virus Load and Genomic Diversity Are Associated with Generation of gp350-Specific Neutralizing Antibodies following Acute Infectious Mononucleosis," Journal of Virology, vol. 91; Issue 1; 16 pages (2017).

Communication pursuant to Rule 164(1) EPC, Partial European Search Report for EP Application No. 18844134.9, titled: "Antibody to Epstein Barr Virus and Uses Thereof," mailed Mar. 31, 2021.

* cited by examiner

10 µg/mL each
| Dilution | EBV- | EBV+ | RG1.E11. C11 | RG1.E11. D11b | RF1.H3b. E3.B8 | RF1.H3b.E3. D7b |
|---|---|---|---|---|---|---|
| Neat | 100 | 0 | 75 | 75 | 75 | 100 |
| 1/2 | 100 | 0 | 100 | 100 | 100 | 100 |
| 1/4 | 100 | 0 | 100 | 100 | 100 | 100 |
| 1/8 | 100 | 0 | 100 | 100 | 100 | 100 |
| 1/16 | 100 | 0 | 100 | 100 | 100 | 100 |
| 1/32 | 100 | 50 | 100 | 100 | 100 | 100 |
| 1/64 | 100 | 50 | 100 | 100 | 100 | 100 |
| 1/128 | 100 | 100 | 100 | 100 | 100 | 100 |
100 = 4/4 wells transformed
Figure 2A
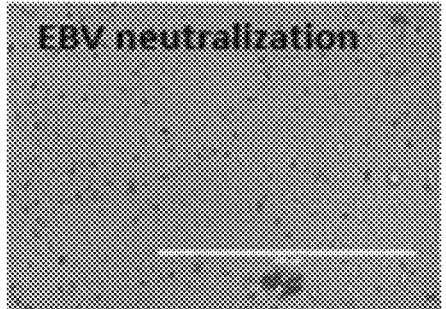 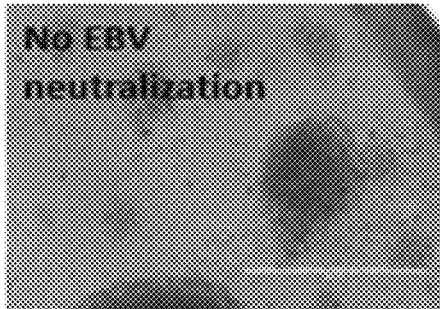
Figure 2B

```
                  Signal Sequence
B8_HC    MGWSCIILFLVATATGVHSEVQLVESAGEVQKPGESLRISCKASGYTFSHYWIGWVRQLP
A11_HC   MGWSCIILFLVATATGVHSEMQLVQSGAEVKKPGASVKVSCKTSGYNFNHQGISWLRQAP
E10_HC   MGWSCIILFLVATATGVHSEVQLVQSGAEVKKPGASVEVSCKASGYTFNAYYIHWVRQAP
B7_HC    MGWSCIILFLVATATGVHSEVQLVQSGAEVKKPGASVEVSCKASGYTFNAYYIHWVRQAP
D7_HC    MGWSCIILFLVATATGVHSEVQLVQSGAEVKKPGASVEVSCKASGYTFNAYYIHWVRQAP
C10_HC   MGWSCIILFLVATATGVHSEVQLVQSGAEVKKPGASVKVSCKASGYTFNAYYIHWVRQAP
         ******************:***.*..**:*** *:..:***:***.*.   * *:** *

B8_HC    GKGLEWMGIIYPDDSDSRYSPSFQGQVTMSVDKSINTAYLQWNSLKVSDTATYYCVRHWL
A11_HC   GQGLEWMGWISGFNGKTNYAQKFQGRVTMTADRSTTTAYMELRSLRSDDTAVYYCASGG-
E10_HC   GQGLDWMGWINPNSGGTNYAQNFKGRVTMTRDTSISTAYLELRSLTSDDTAVYFCATERG
B7_HC    GQGLDWMGWINPNSGGTNYAQNFKGRVTMTRDTSISTAYLELRSLTSDDTAVYFCATERG
D7_HC    GQGLDWMGWINPNSGGTNYAQNFKGRVTMTRDTSISTAYLELRSLTSDDTAVYFCATERG
C10_HC   GQGLDWMGWINPNSGGTNYAQNFKGRVTMTRDTSISTAYLELRSLTSDDTAVYFCATERG
         *:**:*** *    .. :.*: .*:*:***: * *  .***:: .**  .***.*:*.

B8_HC    KRGSNFGFGFDPWGQGTTLTVSSASTKGPSVFPLAPSSKSTSGGTAALGCLVKDYFPEPV
A11_HC   --EQWLVQNFVHWGQGTLLTVSSASTKGPSVFPLAPSSKSTSGGTAALGCLVKDYFPEPV
E10_HC   YTSSFRRDAFDKWGQGTLLTVSSASTKGPSVFPLAPSSKSTSGGTAALGCLVKDYFPEPV
B7_HC    YTSSFRRDAFDKWGQGTMLTVSSASTKGPSVFPLAPSSKSTSGGTAALGCLVKDYFPEPV
D7_HC    YTSSFRRDAFDKWGQGTMLTVSSASTKGPSVFPLAPSSKSTSGGTAALGCLVKDYFPEPV
C10_HC   YTSSFRRDAFDKWGQGTMLTVSSASTKGPSVFPLAPSSKSTSGGTAALGCLVKDYFPEPV
         *  ***** *******************************************

B8_HC    TVSWNSGALTSGVHTFPAVLQSSGLYSLSSVVTVPSSSLGTQTYICNVNHKPSNTKVDKK
A11_HC   TVSWNSGALTSGVHTFPAVLQSSGLYSLSSVVTVPSSSLGTQTYICNVNHKPSNTKVDKK
E10_HC   TVSWNSGALTSGVHTFPAVLQSSGLYSLSSVVTVPSSSLGTQTYICNVNHKPSNTKVDKK
B7_HC    TVSWNSGALTSGVHTFPAVLQSSGLYSLSSVVTVPSSSLGTQTYICNVNHKPSNTKVDKK
D7_HC    TVSWNSGALTSGVHTFPAVLQSSGLYSLSSVVTVPSSSLGTQTYICNVNHKPSNTKVDKK
C10_HC   TVSWNSGALTSGVHTFPAVLQSSGLYSLSSVVTVPSSSLGTQTYICNVNHKPSNTKVDKK
         ************************************************************

B8_HC    VEPKSCDKTHTCPPCPAPELLGGPSVFLFPPKPKDTLMISRTPEVTCVVVDVSHEDPEVK
A11_HC   VEPKSCDKTHTCPPCPAPELLGGPSVFLFPPKPKDTLMISRTPEVTCVVVDVSHEDPEVK
E10_HC   VEPKSCDKTHTCPPCPAPELLGGPSVFLFPPKPKDTLMISRTPEVTCVVVDVSHEDPEVK
B7_HC    VEPKSCDKTHTCPPCPAPELLGGPSVFLFPPKPKDTLMISRTPEVTCVVVDVSHEDPEVK
D7_HC    VEPKSCDKTHTCPPCPAPELLGGPSVFLFPPKPKDTLMISRTPEVTCVVVDVSHEDPEVK
C10_HC   VEPKSCDKTHTCPPCPAPELLGGPSVFLFPPKPKDTLMISRTPEVTCVVVDVSHEDPEVK
         ************************************************************

B8_HC    FNWYVDGVEVHNAKTKPREEQYNSTYRVVSVLTVLHQDWLNGKEYKCKVSNKALPAPIEK
A11_HC   FNWYVDGVEVHNAKTKPREEQYNSTYRVVSVLTVLHQDWLNGKEYKCKVSNKALPAPIEK
E10_HC   FNWYVDGVEVHNAKTKPREEQYNSTYRVVSVLTVLHQDWLNGKEYKCKVSNKALPAPIEK
B7_HC    FNWYVDGVEVHNAKTKPREEQYNSTYRVVSVLTVLHQDWLNGKEYKCKVSNKALPAPIEK
D7_HC    FNWYVDGVEVHNAKTKPREEQYNSTYRVVSVLTVLHQDWLNGKEYKCKVSNKALPAPIEK
C10_HC   FNWYVDGVEVHNAKTKPREEQYNSTYRVVSVLTVLHQDWLNGKEYKCKVSNKALPAPIEK
         ************************************************************

B8_HC    TISKAKGQPREPQVYTLPPSRDELTKNQVSLTCLVKGFYPSDIAVEWESNGQPENNYKTT
A11_HC   TISKAKGQPREPQVYTLPPSRDELTKNQVSLTCLVKGFYPSDIAVEWESNGQPENNYKTT
E10_HC   TISKAKGQPREPQVYTLPPSRDELTKNQVSLTCLVKGFYPSDIAVEWESNGQPENNYKTT
B7_HC    TISKAKGQPREPQVYTLPPSRDELTKNQVSLTCLVKGFYPSDIAVEWESNGQPENNYKTT
D7_HC    TISKAKGQPREPQVYTLPPSRDELTKNQVSLTCLVKGFYPSDIAVEWESNGQPENNYKTT
C10_HC   TISKAKGQPREPQVYTLPPSRDELTKNQVSLTCLVKGFYPSDIAVEWESNGQPENNYKTT
         ************************************************************

B8_HC    PPVLDSDGSFFLYSKLTVDKSRWQQGNVFSCSVMHEALHNHYTQKSLSLSPGK
A11_HC   PPVLDSDGSFFLYSKLTVDKSRWQQGNVFSCSVMHEALHNHYTQKSLSLSPGK
E10_HC   PPVLDSDGSFFLYSKLTVDKSRWQQGNVFSCSVMHEALHNHYTQKSLSLSPGK
B7_HC    PPVLDSDGSFFLYSKLTVDKSRWQQGNVFSCSVMHEALHNHYTQKSLSLSPGK
D7_HC    PPVLDSDGSFFLYSKLTVDKSRWQQGNVFSCSVMHEALHNHYTQKSLSLSPGK
C10_HC   PPVLDSDGSFFLYSKLTVDKSRWQQGNVFSCSVMHEALHNHYTQKSLSLSPGK
         ****************************************************
```

Figure 5A

```
                         Signal Sequence
A11_LC(Lambda)    MGWSCIILFLVATATGVHSETVLTQEPSLTVSPGGTVTLTCASSTGAVTSGYYPNWFQQK
B8_LC(Lambda)     MGWSCIILFLVATATGVHSESALTQPASVSGSPGQSITISCTGTSSDVGGYNYVSWYQQH
C10_LC (Lambda)   MGWSCIILFLVATATGVHSEAVVTQPPSASGTPGQGVTISCSGSSSNIG-SNFVYWYQQL
E10_LC (Lambda)   MGWSCIILFLVATATGVHSESVLTQPPSISAAPGQRVTIPCSGSSSDIG-NHYVSWYQQL
B7_LC(Lambda)     MGWSCIILFLVATATGVHSESVLTQPPSVSAAPGQKVTISCSGSSSNIG-NNYVSWYQQL
D7_LC(Lambda)     MGWSCIILFLVATATGVHSESVLTQPPSVSAAPGQKVTMSCSGSTSNIG-SNSVSWYQHL
                  ******************:.:**  * : :**  :*: *:.::. :      *:*:

A11_LC(Lambda)    PGQAPRALIYSTSNKHSWTPARFSGSLLGGKAALTLSGVQPEDEAEYYCLLYYGG--AWV
B8_LC(Lambda)     PGKAPKLMIYDVSNRPSGVSNRFSGSKSGNTASLTISGLQAEDEADYYCSSYTSS-STLV
C10_LC (Lambda)   PGTAPKLLIYRNNQRPSGVPDRFSGSKSATSASLAISGLRSEDEADYYCATWDDSLSGYV
E10_LC (Lambda)   PGAAPKLLIYEDNKRPSGIPDRFSGSKSGTSASLGITGLQTGDEADYYCGTWDNSLRSGF
B7_LC(Lambda)     PGTAPKLLIYENNKRPSGIPDRFSGSKSGTSATLGITGLQTGDEAGYYCGTWDSSLSAVV
D7_LC(Lambda)     PGTAPKLLLFDNAKRPSGIPDRFSGSKSGTSATLGITGLQTGDEADYYCGTWDSGLSVMV
                  ** **: ::.     ::  *      *****  . .*:* ::*::   *** ***  :  .    .

A11_LC(Lambda)    FGGGTKLTVLGQPKAAPSVTLFPPSSEELQANKATLVCLISDFYPGAVTVAWKADSSPVK
B8_LC(Lambda)     FGGGTKLTVLGQPKAAPSVTLFPPSSEELQANKATLVCLISDFYPGAVTVAWKADSSPVK
C10_LC (Lambda)   FGTGTKLTVLGQPKAAPSVTLFPPSSEELQANKATLVCLISDFYPGAVTVAWKADSSPVK
E10_LC (Lambda)   FGGGTKVTVLGQPKAAPSVTLFPPSSEELQANKATLVCLISDFYPGAVTVAWKADSSPVK
B7_LC(Lambda)     FGGGTKLTVLGQPKAAPSVTLFPPSSEELQANKATLVCLISDFYPGAVTVAWKADSSPVK
D7_LC (Lambda)    FGGGTKLTVLGQPKAAPSVTLFPPSSEELQANKATLVCLISDFYPGAVTVAWKADSSPVK
                  ** ***.:****************************************************

A11_LC(Lambda)    AGVETTTPSKQSNNKYAASSYLSLTPEQWKSHRSYSCQVTHEGSTVEKTVAPTECS-
B8_LC(Lambda)     AGVETTTPSKQSNNKYAASSYLSLTPEQWKSHRSYSCQVTHEGSTVEKTVAPTECS*
C10_LC(Lambda)    AGVETTTPSKQSNNKYAASSYLSLTPEQWKSHRSYSCQVTHEGSTVEKTVAPTECS-
E10_LC(Lambda)    AGVETTTPSKQSNNKYAASSYLSLTPEQWKSHRSYSCQVTHEGSTVEKTVAPTECS-
B7_LC(Lambda)     AGVETTTPSKQSNNKYAASSYLSLTPEQWKSHRSYSCQVTHEGSTVEKTVAPTECS-
D7_LC(Lambda)     AGVETTTPSKQSNNKYAASSYLSLTPEQWKSHRSYSCQVTHEGSTVEKTVAPTECS-
                  ********************************************************
```

Figure 5B

Signal:     VWD1 A, Wavelength = 280 nm

| RT [min] | Height | Width [min] | Area | Area% |
|---|---|---|---|---|
| 10.516 | 0.3282 | 1.1675 | 22.9863 | 0.5422 |
| 12.131 | 158.0809 | 0.4434 | 4205.4116 | 99.1935 |
| 14.486 | 0.1659 | 1.1256 | 11.2070 | 0.2643 |
| | | Sum | 4239.6049 | |

Signal:      VWD1 A, Wavelength = 280 nm

| RT [min] | Height | Width [min] | Area | Area% |
|---|---|---|---|---|
| 10.123 | 0.9797 | 0.7960 | 46.7904 | 1.6633 |
| 12.209 | 103.9368 | 0.4432 | 2763.7512 | 98.2453 |
| 14.536 | 0.0712 | 0.6017 | 2.5710 | 0.0914 |
| | | Sum | 2813.1126 | |

ANTIBODY TO EPSTEIN BARR VIRUS AND USES THEREOF

RELATED APPLICATIONS

This application is the U.S. National Stage of International Application No. PCT/AU2018/050851, filed on Aug. 10, 2018, which designates the U.S., published in English, and claims priority under 35 U.S.C. § 119 or 365(c) to Australian Application No. 2017903197, filed on Aug. 10, 2017. The entire teachings of the above applications are incorporated herein by reference.

INCORPORATION BY REFERENCE OF MATERIAL IN ASCII TEXT FILE

This application incorporates by reference the Sequence Listing contained in the following ASCII text file being submitted concurrently herewith:

a) File name: 57851000-001_SL.txt; created Sep. 10, 2025; 126,153 bytes in size.

TECHNICAL FIELD

THIS INVENTION relates to Epstein-Barr virus (EBV). More particularly, this invention relates to an antibody that at least partly blocks gp350-mediated entry of EBV into human cells.

BACKGROUND

Epstein-Barr virus (EBV) or Human Herpesvirus 4 (HHV-4) is a double stranded DNA virus that belongs to the □-herpesvirus subfamily. It is a common human pathogen that predominantly infects hosts through epithelial cells and B cells, where it can then establish long-term latency in the human host. Primary infection of EBV causes over 90% of cases of infectious mononucleosis (IM) worldwide, infecting mainly children and young adults through the dramatic expansion of EBV infected B cells (Coghill and Hildesheim 2014). EBV has been associated with several cancers, including Burkitt and Hodgkins lymphomas, gastric and nasopharyngeal carcinomas, lymphomas in HIV-infected individuals and post-transplant lymphoproliferative disorder (PTLD). Recently, EBV has also been found to be implicated in autoimmune diseases, particularly multiple sclerosis (MS) (Coghill and Hildesheim 2014).

Epstein-Barr virus encoded gp350 is one of the major targets for anti-viral humoral immunity as it mediates attachment to B cells via complement receptor 2. Gp350 is the primary glycoprotein that elicits anti-viral neutralising antibody responses after natural EBV infection. Currently, there is no commercially available prophylactic or therapeutic treatment that can prevent or cure acute EBV infection. Clinical trials utilising vaccinia-vectored gp350 demonstrated potential immunogenicity and efficacy in young children (Gu, Huang et al. 1995). Subsequent studies by GlaxoSmithKline Biologicals based on a recombinant gp350/aluminium hydroxide and 3-O-desacyl-4'-monophosphoryl lipid A (AS04) candidate vaccine showed demonstrable efficacy (mean efficacy rate, 78.0% [95% confidence interval, 1.0%-96.0%]) in preventing the development of infectious mononucleosis induced by EBV infection, but it had no efficacy in preventing asymptomatic EBV infection (Moutschen, Leonard et al. 2007). Furthermore, Haque and colleagues have also assessed potential clinical application of a murine monoclonal antibody against gp350 (72A1) both in vivo and in vitro (Haque, Johannessen et al. 2006).

SUMMARY

The present invention is broadly directed to an anti-gp350 antibody that at least partly prevents or inhibits the binding of EBV gp350 to human cells. A particular form of the invention provides a human or humanized, recombinant anti-gp350 antibody.

In a first aspect the invention provides a recombinant, human or humanized antibody or antibody fragment that is capable of at least partly preventing or inhibiting Epstein Barr Virus (EBV) gp350 binding to a human cell.

In a particular embodiment, the human or humanized antibody or antibody fragment comprises, consists essentially of or consists of an amino acid sequence set forth in any one of SEQ ID NOS: 1-156, FIG. 5 and/or Tables 1-12, or an amino acid sequence at least 70% identical thereto.

In a particular embodiment, the human or humanized antibody or antibody fragment comprises, consists essentially of or consists of heavy chain and/or light chain complementarity-determining region (CDR) regions that respectively comprise an amino acid sequence set forth in any one of SEQ ID NOS: 1-156, FIG. 5 and/or Tables 1-12.

Preferred CDR amino acid sequences are set forth in SEQ ID NOS: 1-144 and Tables 1-12, or an amino acid sequence at least 70% identical thereto.

In a particular embodiment, the human or humanized antibody or antibody fragment comprises, consists essentially of or consists of an amino acid sequence set forth in any one of SEQ ID NOS: 145-156 and/or FIG. 5, or an amino acid sequence at least 70% identical thereto.

In a second aspect, the invention provides an antibody or antibody fragment that comprises, consists essentially of or consists of at least one complementarity-determining region (CDR) amino acid sequence according to any one of SEQ ID NOS: 1-156, FIG. 5 and/or Tables 1-12, or an amino acid sequence at least 70% identical thereto.

In a particular embodiment, the antibody or antibody fragment comprises, consists essentially of or consists of heavy chain and/or light chain CDR regions that respectively comprise an amino acid sequence set forth in any one of SEQ ID NOS: 1-156, FIG. 5 and/or Tables 1-12, or an amino acid sequence at least 70% identical thereto.

Preferred CDR amino acid sequences are set forth in SEQ ID NOS: 1-144 and Tables 1-12, or an amino acid sequence at least 70% identical thereto.

In a particular embodiment, the antibody or antibody fragment is a humanized antibody or antibody fragment that comprises, consists essentially of or consists of an amino acid sequence set forth in any one of SEQ ID NOS: 145-156 and/or FIG. 5.

Suitably, the antibody or antibody fragment of the second aspect is capable of at least partly preventing or inhibiting Epstein Barr virus (EBV) gp350 binding to a human cell.

Preferably, the antibody or antibody fragment of the first and second aspects is a neutralizing antibody.

In one embodiment, the antibody or antibody fragment of the first and/or second aspects is produced by phage display, wherein the phage comprise one or more nucleotide sequences of human or non-human origin encoding one or more amino acid sequences of the antibody or antibody fragment. The one or more amino acid sequences may be $V_H$, $V_L$, and/or CDR amino acid sequences of human origin such as set forth in SEQ ID NOS: 1-156, FIG. 5 and/or Tables 1-12.

In a third aspect, the invention provides an isolated nucleic acid encoding the antibody or antibody fragment of the first or second aspects.

This aspect also includes genetic constructs comprising the isolated nucleic acid and/or host cells comprising the isolated nucleic acid and/or genetic construct.

In a fourth aspect, the invention provides a composition comprising the antibody or antibody fragment of the first aspect, the second aspect and/or the isolated nucleic acid of the third aspect and a pharmaceutically acceptable carrier, diluent or excipient In a fifth aspect, the invention provides a method of treating or preventing an EBV infection in a human, said method including the step of administering the antibody of the first aspect, the second aspect and/or the composition of the fourth aspect to the human to thereby treat or prevent an EBV infection in the human.

In a sixth aspect, the invention provides a method of passively immunizing a human against an EBV infection, said method including the step of administering the antibody of the first aspect, the second aspect and/or the composition of the fourth aspect to the human to thereby passively immunize the human against an EBV infection.

In a seventh aspect, the invention provides a method of at least partly inhibiting or preventing EBV gp350 binding to a human cell, said method including the step of administering the antibody of the first aspect, the second aspect and/or the composition of the fourth aspect to the human to thereby at least partly inhibit or prevent EBV gp350 binding to a human cell.

In an eighth aspect, the invention provides a method or system for determining the efficacy of an anti-EBV antibody or antibody fragment, said method or system comprising infecting a mouse with EBV, the mouse comprising human B lymphocytes, and determining the efficacy of a candidate anti-EBV antibody or antibody fragment in the mouse.

Suitably, efficacy relates to or includes the ability of the candidate anti-EBV antibody or antibody fragment to prevent EBV gp350 binding to one or more of the B lymphocytes.

Suitably, the human B lymphocytes have been derived from human hematopoietic stem cells administered to the mouse. Preferably, the human hematopoietic stem cells are CD34+.

In a ninth aspect, the invention provides a method of detecting EBVgp350 or a cell expressing EBVgp350, said method including the step of forming a complex between the antibody or antibody fragment of the first and/or second aspects and EBV gp350 to thereby detect EBVgp350 or the cell expressing EBVgp350.

Throughout this specification, unless the context requires otherwise, the words "comprise", "comprises" and "comprising" will be understood to imply the inclusion of a stated integer or group of integers but not the exclusion of any other integer or group of integers.

By "consists essentially of" in the context of an amino acid sequence means that the recited amino acid sequences includes an additional 1, 2, 3, 4, or 5 amino acids at an N- and/or C-terminus thereof.

As used herein, the indefinite articles 'a' and 'an' are used here to refer to or encompass singular or plural elements or features and should not be taken as meaning or defining "one" or a "single" element or feature.

4

FIG. 2: A) Assessment of neutralizing capacity of gp350-specific murine monoclonal antibodies (RG1.E11.D11b, RG1.E11.C11, RF1.H3b.E3.B8 and RF1.H3b.E3.D7b). Serum from a seronegative donor (referred to as EBV−) and a seropositive donor (referred to as EBV+) were used as negative and positive controls respectively. B) Representative photomicrographs of outgrowth of EBV transformed B cells in the presence of seropositive (upper panel) and seronegative serum.

Figure 3:
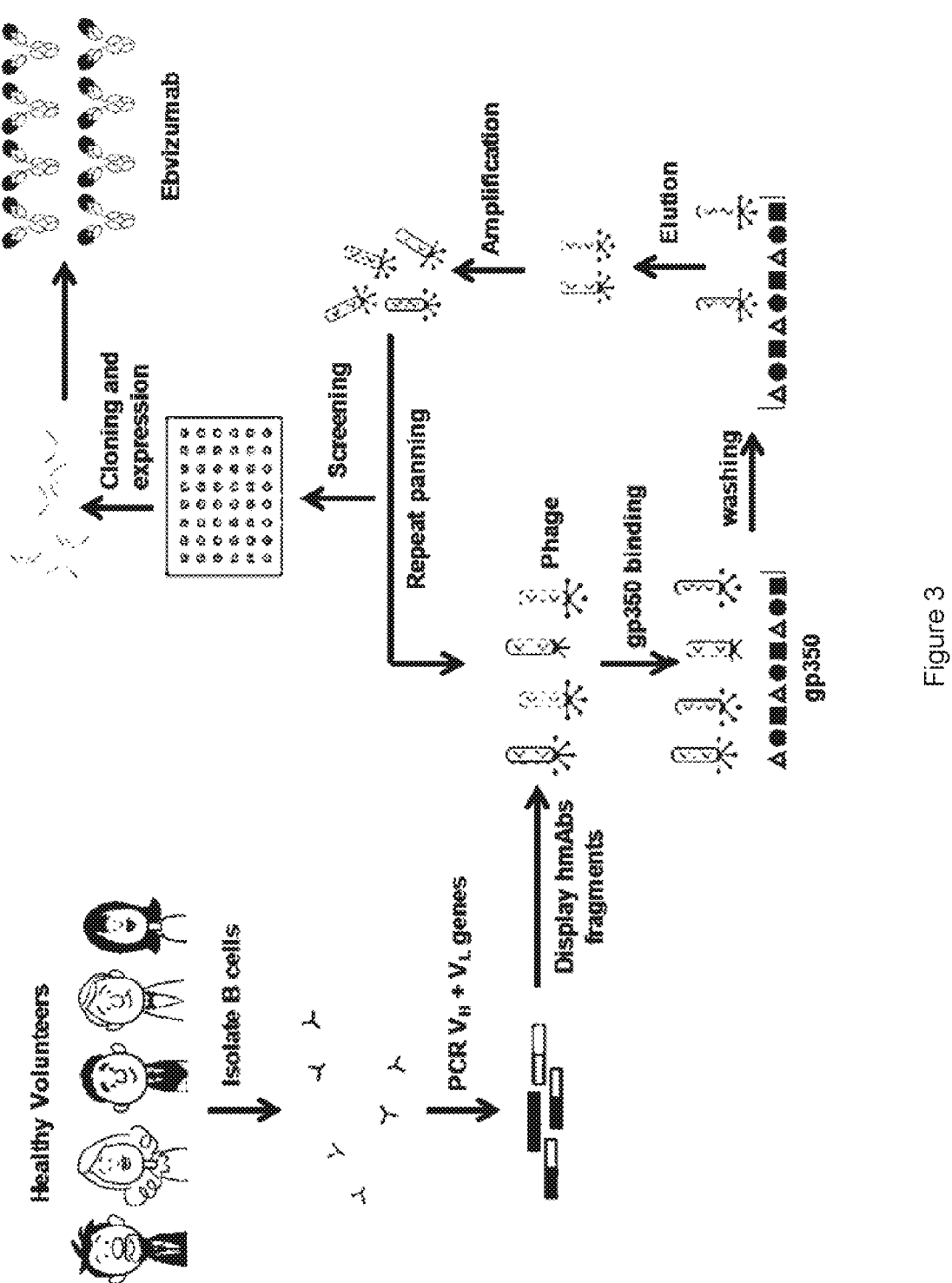

FIG. 3: Schematic overview of antibody library production and selections using phage display. The phage antibody library repertoire is derived from the B cells of immune donors. Bio-panning represents selection of phage coated antibody binders.

Figure 4:
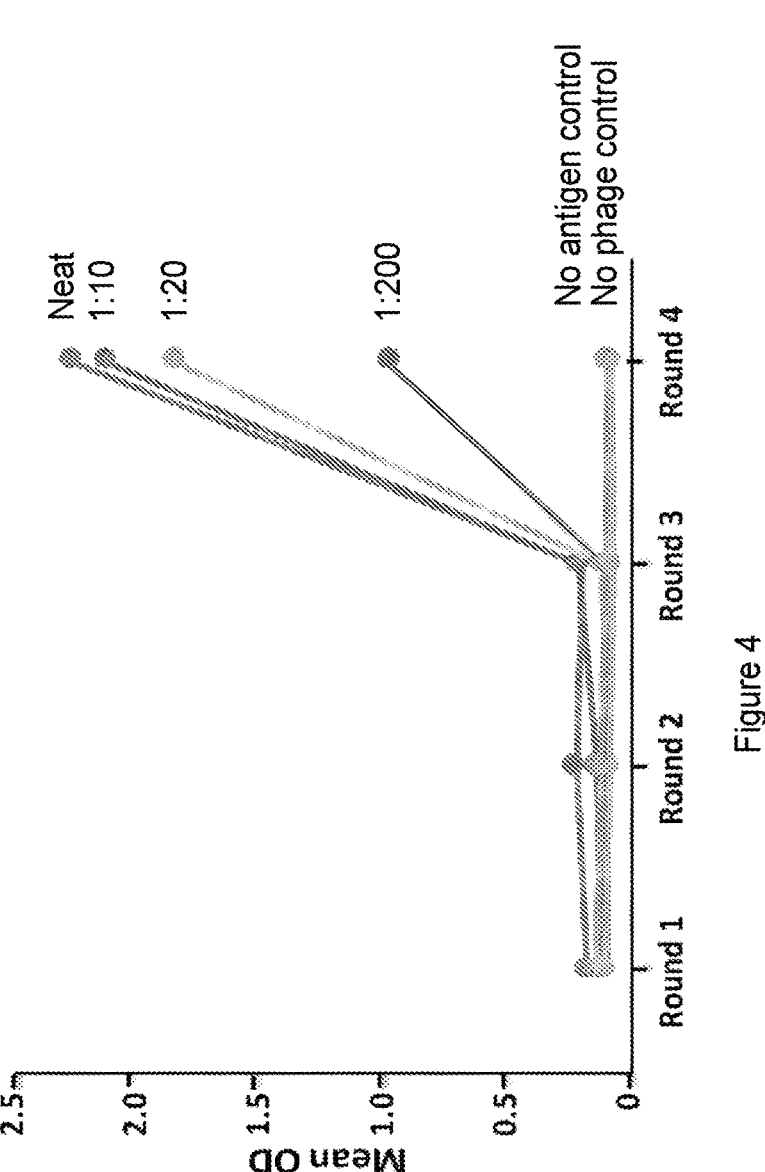

FIG. 4: Polyclonal ELISA to identify enriched binders specific to gp350. Round 4 of bio-panning shows significant enrichment for binders to gp350.

FIG. 5: Alignment of reformatted IgG1 heavy chain (HC; Panel A) and light chain (LC; Panel B) amino acid sequences of six gp350-specific clones. Amino acid changes in the original CDR regions are shown in bold text. Signal sequence for extracellular secretion of immunoglobulin is underlined. Clone B8 HC=SEQ ID NO: 145; Clone A11 HC=SEQ ID NO: 146; Clone E10 HC=SEQ ID NO: 147; Clone B7 HC=SEQ ID NO: 148; Clone D7 HC=SEQ ID NO: 149; Clone C10 HC=SEQ ID NO: 150; Clone B8 LC=SEQ ID NO: 151; Clone A11 LC=SEQ ID NO: 152; Clone E10 LC=SEQ ID NO: 153; Clone B7 LC=SEQ ID NO: 154; Clone D7 LC=SEQ ID NO: 155; Clone C10 LC-SEQ ID NO: 156.

Figure 6A:
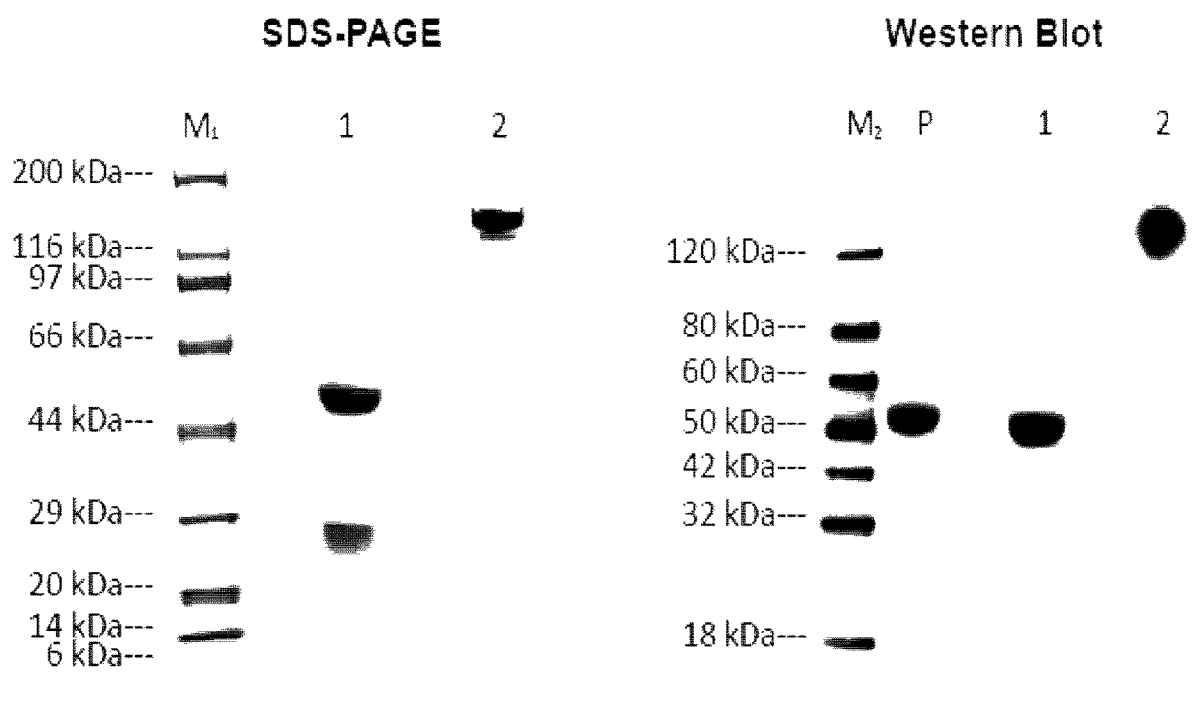
Figure 6B:
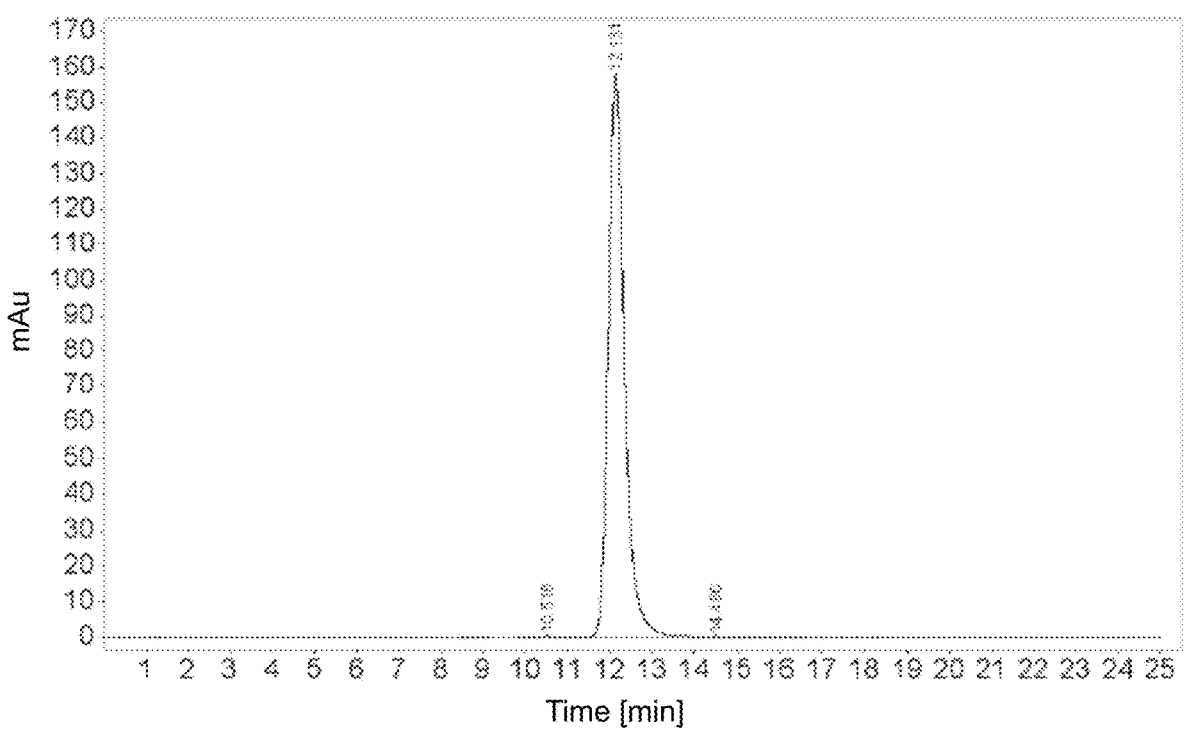

FIG. 6: SDS-PAGE and Western blot analysis (A) of gp350-specific clone B8 recombinant human antibody expressed in Expi293F cells grown in serum-free Expi293FTM expression medium. The recombinant plasmids encoding B8 heavy and light chain were transiently co-transfected into suspension Expi293F cell cultures. The cell culture supernatants collected on day 6 were used for purification. Lane M1: Protein Marker, Lane M2: Protein Marker, Lane 1: Reducing conditions, Lane 2: Non-reducing conditions, Lane P: Human IgG$_1$, Kappa (as positive control). The purified protein was also analyzed by SEC-HPLC analysis (B) for molecular weight and purity measurements.

Figure 7A:
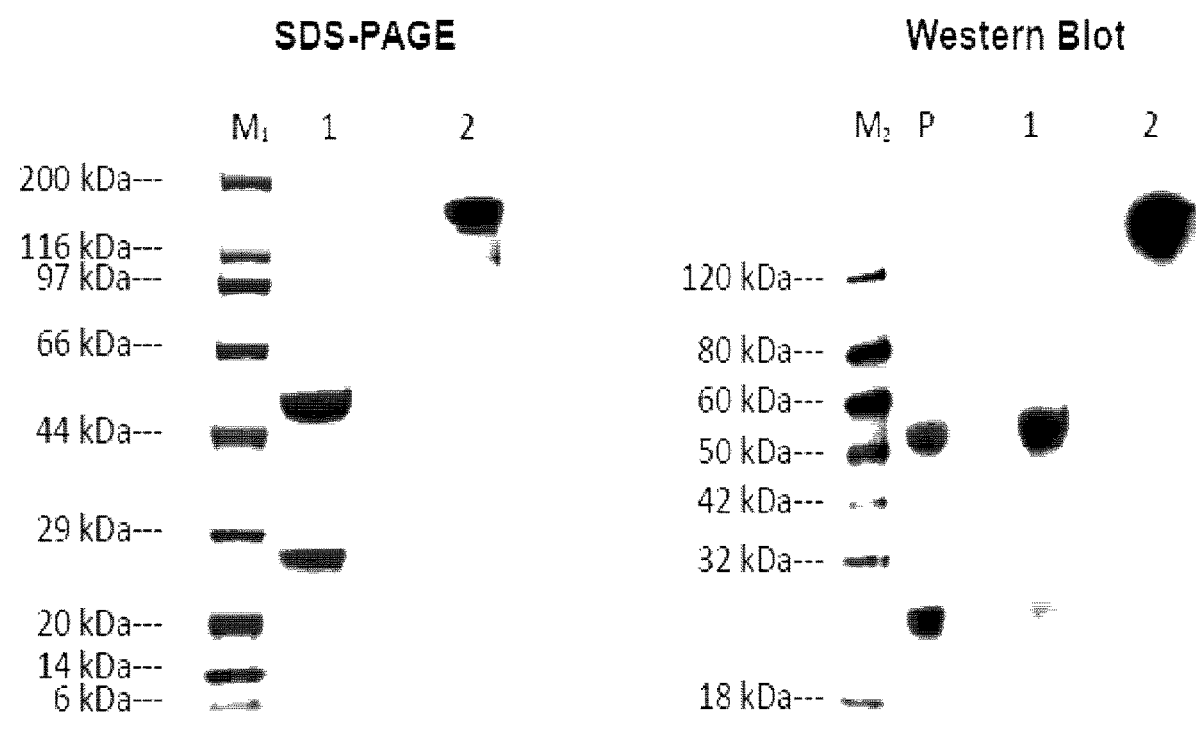

FIG. 7(A): SDS-PAGE and Western blot analysis of gp350-specific clone B7 recombinant human antibody expressed in Expi293F cells grown in serum-free Expi293FTM expression medium. The recombinant plasmids encoding B8 heavy and light chain were transiently co-transfected into suspension Expi293F cell cultures. The cell culture supernatants collected on day 6 were used for purification. Lane M1: Protein Marker, Lane M2: Protein Marker, Lane 1: Reducing conditions, Lane 2: Non-reducing conditions, Lane P: Human IgG$_1$, Kappa (as positive control). The purified protein was also analyzed by SEC-HPLC analysis (B) for molecular weight and purity measurements.

Figure 8:
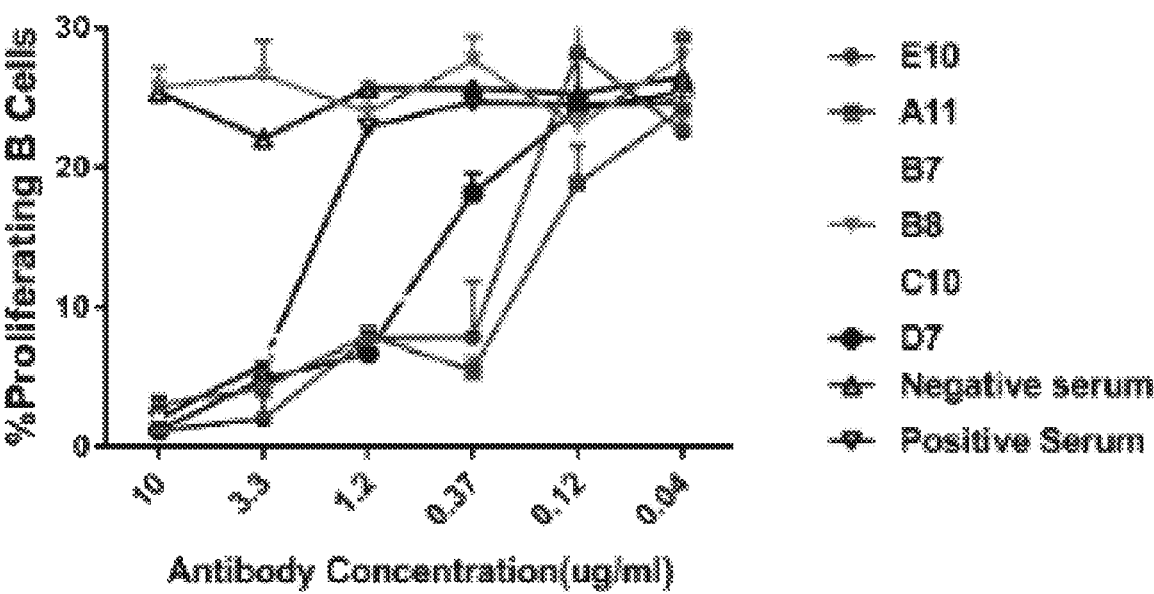

FIG. 8: Assessment of EBV neutralizing capacity of human monoclonal antibody clones. Purified EBV was initially incubated with serially diluted purified human monoclonal antibodies specific for gp350 or human serum from seronegative or seropositive donors for 1 h. Following pre-treatment with these antibodies, EBV was exposed to human PBMC pre-labelled with CTV. After 7 days these cells were assessed for EBV-driven proliferation.

Figure 9:
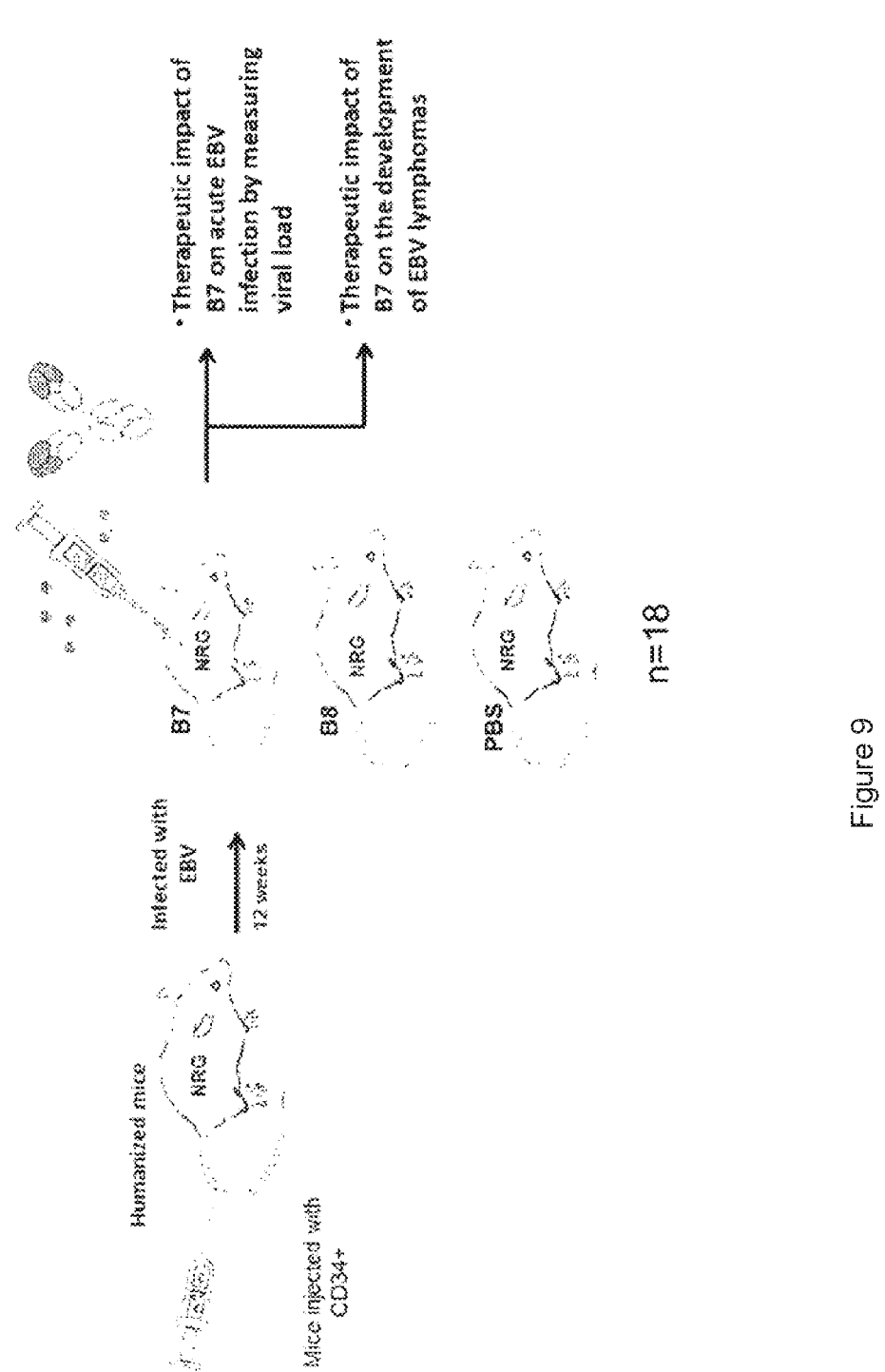

FIG. 9: Therapeutic assessment approach of humanized mice infected with EBV. Mice were given 100 µg antibody treatment or PBS in each group after 5 and 10 days post EBV injections, n=18.

Figure 10:
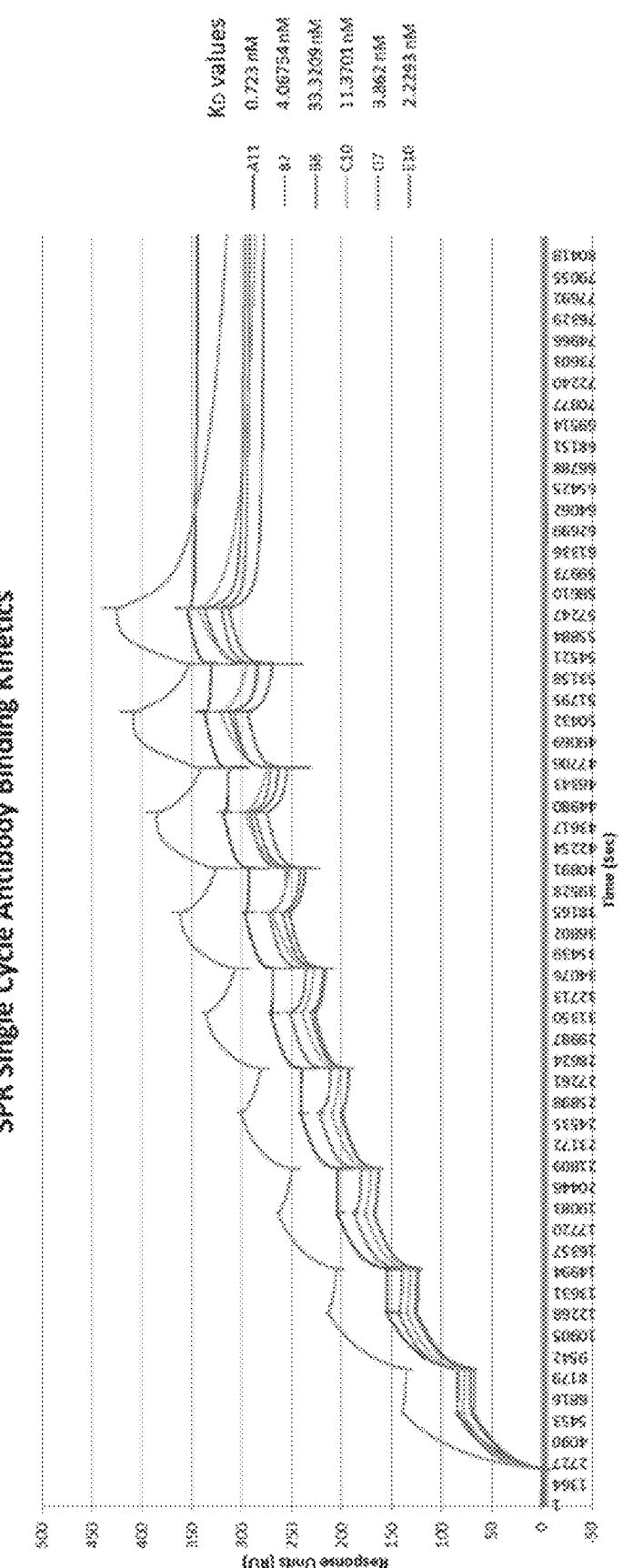

FIG. 10: Interactions of gp350 (immobilised on CM5 sensor chip) with increasing concentrations of humanized monoclonal antibodies A11, B7, B8, C10, D7 and E10 via single cycle kinetics titrations.

Figure 11:
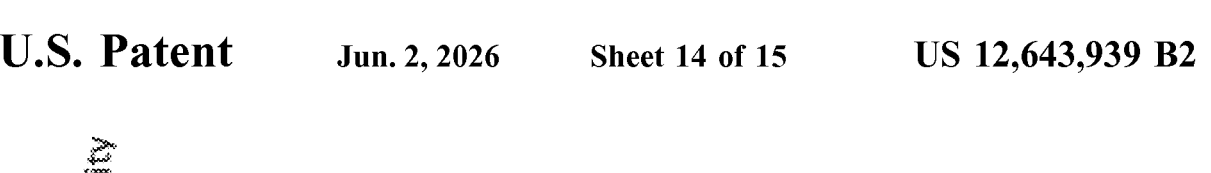

FIG. 11: Affinity steady-state plot of humanized monoclonal antibodies against gp350, fitted using 1:1 Langmuir model of interaction.

Figure 12:
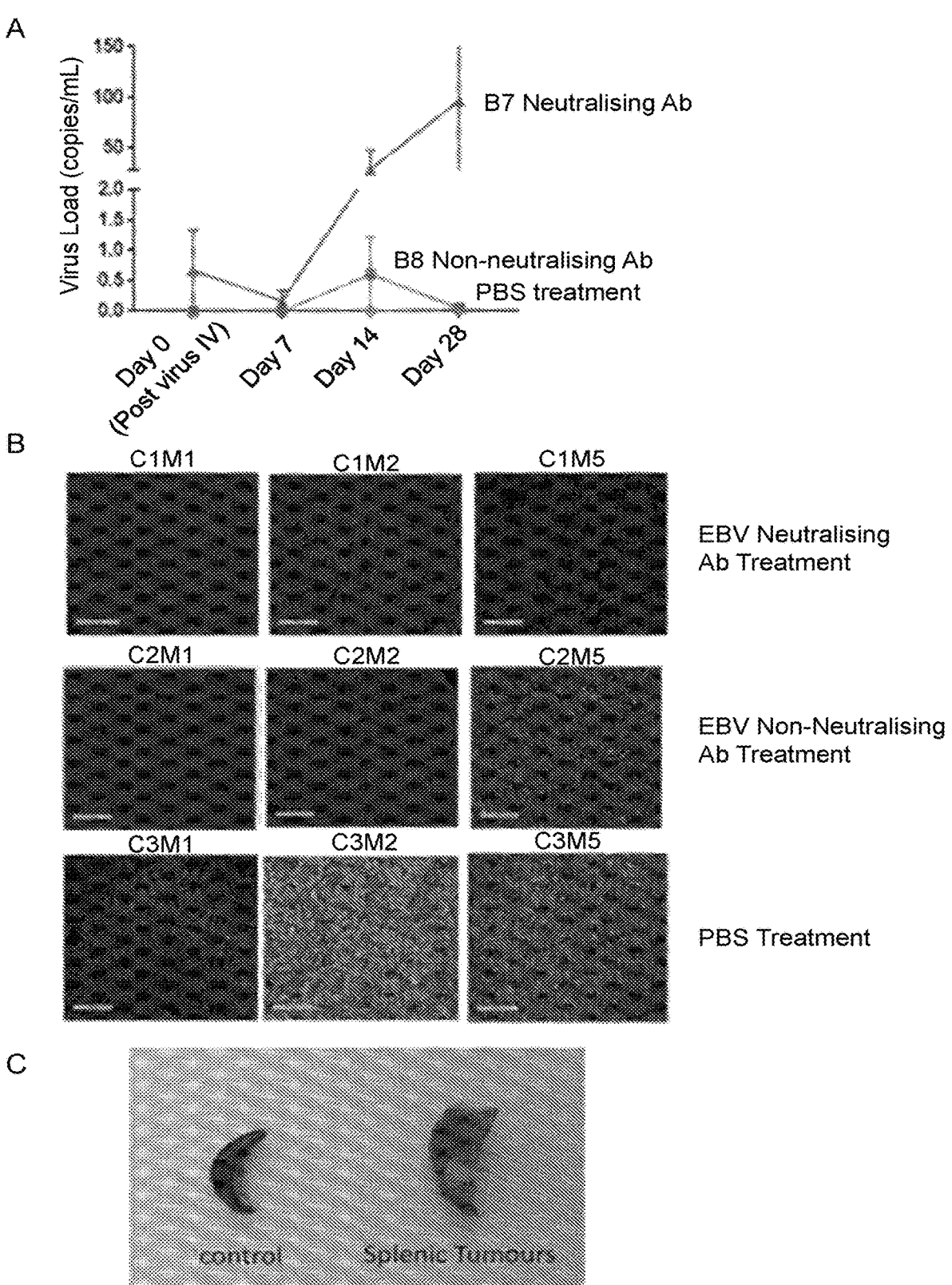

FIG. 12: (A) Viral loads of B7, B8 and PBS treatment groups in humanized mice over the course of 28 days post virus injection. B7 and B8 show significant differences in viral loads 28 days post EBV injection ($p < 0.001$). (B) Histochemical stain analysis of spleen tissue of humanized mice for each treatment group, B7, B8 and PBS. Green represents the presence of EBER in spleen tissues and blue represents normal spleen tissue. (C) Representation of normal spleen seen in B7 treatment group (pictured left) compared to splenomegaly with the presence of tumours (pictured right) which is representative of PBS treatment group.

BRIEF DESCRIPTION OF THE SEQUENCES

SEQ ID NO:1 CloneB8 Heavy Chain CDR1
SEQ ID NO:2 CloneB8 Heavy Chain CDR2
SEQ ID NO:3 CloneB8 Heavy Chain CDR3
SEQ ID NO:4 CloneA11 Heavy Chain CDR1
SEQ ID NO:5 CloneA11 Heavy Chain CDR2
SEQ ID NO:6 CloneA11 Heavy Chain CDR3
SEQ ID NO:7 CloneE10 Heavy Chain CDR1
SEQ ID NO:8 CloneE10 Heavy Chain CDR2
SEQ ID NO:9 CloneE10 Heavy Chain CDR3
SEQ ID NO:10 CloneB7 Heavy Chain CDR1
SEQ ID NO:11 CloneB7 Heavy Chain CDR2
SEQ ID NO:12 CloneB7 Heavy Chain CDR3
SEQ ID NO:13 CloneD7 Heavy Chain CDR1
SEQ ID NO:14 CloneD7 Heavy Chain CDR2
SEQ ID NO:15 CloneD7 Heavy Chain CDR3
SEQ ID NO:16 CloneC10 Heavy Chain CDR1
SEQ ID NO:17 CloneC10 Heavy Chain CDR2
SEQ ID NO:18 CloneC10 Heavy Chain CDR3
SEQ ID NO:19 CloneB8 Light Chain CDR1
SEQ ID NO:20 CloneB8 Light Chain CDR2
SEQ ID NO:21 CloneB8 Light Chain CDR3
SEQ ID NO:22 CloneA11 Light Chain CDR1
SEQ ID NO:23 CloneA11 Light Chain CDR2
SEQ ID NO:24 CloneA11 Light Chain CDR3
SEQ ID NO:25 CloneE10 Light Chain CDR1
SEQ ID NO:26 CloneE10 Light Chain CDR2
SEQ ID NO:27 CloneE10 Light Chain CDR3
SEQ ID NO:28 CloneB7 Light Chain CDR1
SEQ ID NO:29 CloneB7 Light Chain CDR2
SEQ ID NO:30 CloneB7 Light Chain CDR3
SEQ ID NO:31 CloneD7 Light Chain CDR1
SEQ ID NO:32 CloneD7 Light Chain CDR2
SEQ ID NO:33 CloneD7 Light Chain CDR3
SEQ ID NO:34 CloneC10 Light Chain CDR1
SEQ ID NO:35 CloneC10 Light Chain CDR2
SEQ ID NO:36 CloneC10 Light Chain CDR3
SEQ ID NO:37 CloneB8 Heavy Chain CDR1
SEQ ID NO:38 CloneB8 Heavy Chain CDR2
SEQ ID NO:39 CloneB8 Heavy Chain CDR3
SEQ ID NO:40 CloneA11 Heavy Chain CDR1
SEQ ID NO:41 CloneA11 Heavy Chain CDR2
SEQ ID NO:42 CloneA11 Heavy Chain CDR3
SEQ ID NO:43 CloneE10 Heavy Chain CDR1
SEQ ID NO:44 CloneE10 Heavy Chain CDR2
SEQ ID NO:45 CloneE10 Heavy Chain CDR3
SEQ ID NO:46 CloneB7 Heavy Chain CDR1

SEQ ID NO:47 CloneB7 Heavy Chain CDR2
SEQ ID NO:48 CloneB7 Heavy Chain CDR3
SEQ ID NO:49 CloneD7 Heavy Chain CDR1
SEQ ID NO:50 CloneD7 Heavy Chain CDR2
SEQ ID NO:51 CloneD7 Heavy Chain CDR3
SEQ ID NO:52 CloneC10 Heavy Chain CDR1
SEQ ID NO:53 CloneC10 Heavy Chain CDR2
SEQ ID NO:54 CloneC10 Heavy Chain CDR3
SEQ ID NO:55 CloneB8 Light Chain CDR1
SEQ ID NO:56 CloneB8 Light Chain CDR2
SEQ ID NO:57 CloneB8 Light Chain CDR3
SEQ ID NO:58 CloneA11 Light Chain CDR1
SEQ ID NO:59 CloneA11 Light Chain CDR2
SEQ ID NO:60 CloneA11 Light Chain CDR3
SEQ ID NO:61 CloneE10 Light Chain CDR1
SEQ ID NO:62 CloneE10 Light Chain CDR2
SEQ ID NO:63 CloneE10 Light Chain CDR3
SEQ ID NO:64 CloneB7 Light Chain CDR1
SEQ ID NO:65 CloneB7 Light Chain CDR2
SEQ ID NO:66 CloneB7 Light Chain CDR3
SEQ ID NO:67 CloneD7 Light Chain CDR1
SEQ ID NO:68 CloneD7 Light Chain CDR2
SEQ ID NO:69 CloneD7 Light Chain CDR3
SEQ ID NO:70 CloneC10 Light Chain CDR1
SEQ ID NO:71 CloneC10 Light Chain CDR2
SEQ ID NO:72 CloneC10 Light Chain CDR3
SEQ ID NO:73 CloneB8 Heavy Chain CDR1
SEQ ID NO:74 CloneB8 Heavy Chain CDR2
SEQ ID NO:75 CloneB8 Heavy Chain CDR3
SEQ ID NO:76 CloneA11 Heavy Chain CDR1
SEQ ID NO:77 CloneA11 Heavy Chain CDR2
SEQ ID NO:78 CloneA11 Heavy Chain CDR3
SEQ ID NO:79 CloneE10 Heavy Chain CDR1
SEQ ID NO:80 CloneE10 Heavy Chain CDR2
SEQ ID NO:81 CloneE10 Heavy Chain CDR3
SEQ ID NO:82 CloneB7 Heavy Chain CDR1
SEQ ID NO:83 CloneB7 Heavy Chain CDR2
SEQ ID NO:84 CloneB7 Heavy Chain CDR3
SEQ ID NO:85 CloneD7 Heavy Chain CDR1
SEQ ID NO:86 CloneD7 Heavy Chain CDR2
SEQ ID NO:87 CloneD7 Heavy Chain CDR3
SEQ ID NO:88 CloneC10 Heavy Chain CDR1
SEQ ID NO:89 CloneC10 Heavy Chain CDR2
SEQ ID NO:90 CloneC10 Heavy Chain CDR3
SEQ ID NO:91 CloneB8 Light Chain CDR1
SEQ ID NO:92 CloneB8 Light Chain CDR2
SEQ ID NO:93 CloneB8 Light Chain CDR3
SEQ ID NO:94 CloneA11 Light Chain CDR1
SEQ ID NO:95 CloneA11 Light Chain CDR2
SEQ ID NO:96 CloneA11 Light Chain CDR3
SEQ ID NO:97 CloneE10 Light Chain CDR1
SEQ ID NO:98 CloneE10 Light Chain CDR2
SEQ ID NO:99 CloneE10 Light Chain CDR3
SEQ ID NO:100 CloneB7 Light Chain CDR1
SEQ ID NO:101 CloneB7 Light Chain CDR2
SEQ ID NO:102 CloneB7 Light Chain CDR3
SEQ ID NO:103 CloneD7 Light Chain CDR1
SEQ ID NO:104 CloneD7 Light Chain CDR2
SEQ ID NO:105 CloneD7 Light Chain CDR3
SEQ ID NO:106 CloneC10 Light Chain CDR1
SEQ ID NO:107 CloneC10 Light Chain CDR2
SEQ ID NO:108 CloneC10 Light Chain CDR3
SEQ ID NO:109 CloneB8 Heavy Chain CDR1
SEQ ID NO:110 CloneB8 Heavy Chain CDR2
SEQ ID NO:111 CloneB8 Heavy Chain CDR3
SEQ ID NO:112 CloneA11 Heavy Chain CDR1
SEQ ID NO:113 CloneA11 Heavy Chain CDR2

SEQ ID NO:114 CloneA11 Heavy Chain CDR3
SEQ ID NO:115 CloneE10 Heavy Chain CDR1
SEQ ID NO:116 CloneE10 Heavy Chain CDR2
SEQ ID NO:117 CloneE10 Heavy Chain CDR3
SEQ ID NO:118 CloneB7 Heavy Chain CDR1
SEQ ID NO:119 CloneB7 Heavy Chain CDR2
SEQ ID NO:120 CloneB7 Heavy Chain CDR3
SEQ ID NO:121 CloneD7 Heavy Chain CDR1
SEQ ID NO:122 CloneD7 Heavy Chain CDR2
SEQ ID NO:123 CloneD7 Heavy Chain CDR3
SEQ ID NO:124 CloneC10 Heavy Chain CDR1
SEQ ID NO:125 CloneC10 Heavy Chain CDR2
SEQ ID NO:126 CloneC10 Heavy Chain CDR3
SEQ ID NO:127 CloneB8 Light Chain CDR1
SEQ ID NO:128 CloneB8 Light Chain CDR2
SEQ ID NO:129 CloneB8 Light Chain CDR3
SEQ ID NO:130 CloneA11 Light Chain CDR1
SEQ ID NO:131 CloneA11 Light Chain CDR2
SEQ ID NO:132 CloneA11 Light Chain CDR3
SEQ ID NO:133 CloneE10 Light Chain CDR1
SEQ ID NO:134 CloneE10 Light Chain CDR2
SEQ ID NO:135 CloneE10 Light Chain CDR3
SEQ ID NO:136 CloneB7 Light Chain CDR1
SEQ ID NO:137 CloneB7 Light Chain CDR2
SEQ ID NO:138 CloneB7 Light Chain CDR3
SEQ ID NO:139 CloneD7 Light Chain CDR1
SEQ ID NO:140 CloneD7 Light Chain CDR2
SEQ ID NO:141 CloneD7 Light Chain CDR3
SEQ ID NO:142 CloneC10 Light Chain CDR1
SEQ ID NO:143 CloneC10 Light Chain CDR2
SEQ ID NO:144 CloneC10 Light Chain CDR3
SEQ ID NO:145 Clone B8 Heavy Chain IgG$_1$ reformatted antibody fragment
SEQ ID NO:146 CloneA11 Heavy Chain IgG$_1$ reformatted antibody fragment
SEQ ID NO: 147 CloneE10 Heavy Chain IgG$_1$ reformatted antibody fragment
SEQ ID NO: 148 CloneB7 Heavy Chain IgG$_1$ reformatted antibody fragment
SEQ ID NO: 149 CloneD7 Heavy Chain IgG$_1$ reformatted antibody fragment
SEQ ID NO:150 CloneC10 Heavy Chain IgG$_1$ reformatted antibody fragment
SEQ ID NO:151 Clone B8 Light Chain IgG$_1$ reformatted antibody fragment
SEQ ID NO:152 CloneA11 Light Chain IgG$_1$ reformatted antibody fragment
SEQ ID NO:153 CloneE10 Light Chain IgG$_1$ reformatted antibody fragment
SEQ ID NO:154 CloneB7 Light Chain IgG$_1$ reformatted antibody fragment
SEQ ID NO:155 CloneD7 Light Chain IgG$_1$ reformatted antibody fragment
SEQ ID NO:156 CloneC10 Light Chain IgG$_1$ reformatted antibody fragment
SEQ ID NO: 157 Human IgG$_1$ constant region amino acid sequence
SEQ ID NO:158 Clone B8 Heavy Chain PCR product
SEQ ID NO:159 CloneA11 Heavy Chain PCR product
SEQ ID NO:160 CloneE10 Heavy Chain PCR product
SEQ ID NO:161 CloneB7 Heavy Chain PCR product
SEQ ID NO:162 CloneD7 Heavy Chain PCR product
SEQ ID NO:163 CloneC10 Heavy Chain PCR product
SEQ ID NO:164 Clone B8 Light Chain PCR product
SEQ ID NO:165 CloneA11 Light Chain PCR product
SEQ ID NO:166 CloneE10 Light Chain PCR product
SEQ ID NO:167 CloneB7 Light Chain PCR product SEQ ID NO:168 CloneD7 Light Chain PCR product
SEQ ID NO: 169 CloneC10 Light Chain PCR product
SEQ ID NO:170 CloneB8 Heavy Chain HFR1
SEQ ID NO:171 CloneB8 Heavy Chain HFR2
SEQ ID NO:172 CloneB8 Heavy Chain HFR3
SEQ ID NO:173 CloneB8 Heavy Chain HFR4
SEQ ID NO:174 CloneA11 Heavy Chain HFR1
SEQ ID NO:175 CloneA11 Heavy Chain HFR2
SEQ ID NO:176 CloneA11 Heavy Chain HFR3
SEQ ID NO:177 CloneA11 Heavy Chain HFR4
SEQ ID NO:178 CloneE10 Heavy Chain HFR1
SEQ ID NO:179 CloneE10 Heavy Chain HFR2
SEQ ID NO:180 CloneE10 Heavy Chain HFR3
SEQ ID NO:181 CloneE10 Heavy Chain HFR4
SEQ ID NO:182 CloneB7 Heavy Chain HFR1
SEQ ID NO:183 CloneB7 Heavy Chain HFR2
SEQ ID NO:184 CloneB7 Heavy Chain HFR3
SEQ ID NO:185 CloneB7 Heavy Chain HFR4
SEQ ID NO:186 CloneD7 Heavy Chain HFR1
SEQ ID NO:187 CloneD7 Heavy Chain HFR2
SEQ ID NO:188 CloneD7 Heavy Chain HFR3
SEQ ID NO:189 CloneD7 Heavy Chain HFR4
SEQ ID NO:190 CloneC10 Heavy Chain HFR1
SEQ ID NO:191 CloneC10 Heavy Chain HFR2
SEQ ID NO:192 CloneC10 Heavy Chain HFR3
SEQ ID NO: 193 CloneC10 Heavy Chain HFR4
SEQ ID NO: 194 CloneB8 Light Chain LFR1
SEQ ID NO:195 CloneB8 Light Chain LFR2
SEQ ID NO:196 CloneB8 Light Chain LFR3
SEQ ID NO:197 CloneB8 Light Chain LFR4
SEQ ID NO:198 CloneA11 Light Chain LFR1
SEQ ID NO:199 CloneA11 Light Chain LFR2
SEQ ID NO:200 CloneA11 Light Chain LFR3
SEQ ID NO:201 CloneA11 Light Chain LFR4
SEQ ID NO:202 CloneE10 Light Chain LFR1
SEQ ID NO:203 CloneE10 Light Chain LFR2
SEQ ID NO:204 CloneE10 Light Chain LFR3
SEQ ID NO:205 CloneE10 Light Chain LFR4
SEQ ID NO:206 CloneB7 Light Chain LFR1
SEQ ID NO:207 CloneB7 Light Chain LFR2
SEQ ID NO:208 CloneB7 Light Chain LFR3
SEQ ID NO:209 CloneB7 Light Chain LFR4
SEQ ID NO:210 CloneD7 Light Chain LFR1
SEQ ID NO:211 CloneD7 Light Chain LFR2
SEQ ID NO:212 CloneD7 Light Chain LFR3
SEQ ID NO:213 CloneD7 Light Chain LFR4
SEQ ID NO:214 CloneC10 Light Chain LFR1
SEQ ID NO:215 CloneC10 Light Chain LFR2
SEQ ID NO:216 CloneC10 Light Chain LFR3
SEQ ID NO:217 CloneC10 Light Chain LFR4
SEQ ID NO:218 CloneB8 Heavy Chain HFR1
SEQ ID NO:219 CloneB8 Heavy Chain HFR2
SEQ ID NO:220 CloneB8 Heavy Chain HFR3
SEQ ID NO:221 CloneB8 Heavy Chain HFR4
SEQ ID NO:222 CloneA11 Heavy Chain HFR1
SEQ ID NO:223 CloneA11 Heavy Chain HFR2
SEQ ID NO:224 CloneA11 Heavy Chain HFR3
SEQ ID NO:225 CloneA11 Heavy Chain HFR4
SEQ ID NO:226 CloneE10 Heavy Chain HFR1
SEQ ID NO:227 CloneE10 Heavy Chain HFR2
SEQ ID NO:228 CloneE10 Heavy Chain HFR3
SEQ ID NO:229 CloneE10 Heavy Chain HFR4
SEQ ID NO:230 CloneB7 Heavy Chain HFR1
SEQ ID NO:231 CloneB7 Heavy Chain HFR2
SEQ ID NO:232 CloneB7 Heavy Chain HFR3
SEQ ID NO:233 CloneB7 Heavy Chain HFR4
SEQ ID NO:234 CloneD7 Heavy Chain HFR1

SEQ ID NO:235 CloneD7 Heavy Chain HFR2
SEQ ID NO:236 CloneD7 Heavy Chain HFR3
SEQ ID NO:237 CloneD7 Heavy Chain HFR4
SEQ ID NO:238 CloneC10 Heavy Chain HFR1
SEQ ID NO:239 CloneC10 Heavy Chain HFR2
SEQ ID NO:240 CloneC10 Heavy Chain HFR3
SEQ ID NO:241 CloneC10 Heavy Chain HFR4
SEQ ID NO:242 CloneB8 Light Chain LFR1
SEQ ID NO:243 CloneB8 Light Chain LFR2
SEQ ID NO:244 CloneB8 Light Chain LFR3
SEQ ID NO:245 CloneB8 Light Chain LFR4
SEQ ID NO:246 CloneA11 Light Chain LFR1
SEQ ID NO:247 CloneA11 Light Chain LFR2
SEQ ID NO:248 CloneA11 Light Chain LFR3
SEQ ID NO:249 CloneA11 Light Chain LFR4
SEQ ID NO:250 CloneE10 Light Chain LFR1
SEQ ID NO:251 CloneE10 Light Chain LFR2
SEQ ID NO:252 CloneE10 Light Chain LFR3
SEQ ID NO:253 CloneE10 Light Chain LFR4
SEQ ID NO:254 CloneB7 Light Chain LFR1
SEQ ID NO:255 CloneB7 Light Chain LFR2
SEQ ID NO:256 CloneB7 Light Chain LFR3
SEQ ID NO:257 CloneB7 Light Chain LFR4
SEQ ID NO:258 CloneD7 Light Chain LFR1
SEQ ID NO:259 CloneD7 Light Chain LFR2
SEQ ID NO:260 CloneD7 Light Chain LFR3
SEQ ID NO:261 CloneD7 Light Chain LFR4
SEQ ID NO:262 CloneC10 Light Chain LFR1
SEQ ID NO:263 CloneC10 Light Chain LFR2
SEQ ID NO:264 CloneC10 Light Chain LFR3
SEQ ID NO:265 CloneC10 Light Chain LFR4
SEQ ID NO:266 CloneB8 Heavy Chain HFR1
SEQ ID NO:267 CloneB8 Heavy Chain HFR2
SEQ ID NO:268 CloneB8 Heavy Chain HFR3
SEQ ID NO:269 CloneB8 Heavy Chain HFR4
SEQ ID NO:270 CloneA11 Heavy Chain HFR1
SEQ ID NO:271 CloneA11 Heavy Chain HFR2
SEQ ID NO:272 CloneA11 Heavy Chain HFR3
SEQ ID NO:273 CloneA11 Heavy Chain HFR4
SEQ ID NO:274 CloneE10 Heavy Chain HFR1
SEQ ID NO:275 CloneE10 Heavy Chain HFR2
SEQ ID NO:276 CloneE10 Heavy Chain HFR3
SEQ ID NO:277 CloneE10 Heavy Chain HFR4
SEQ ID NO:278 CloneB7 Heavy Chain HFR1
SEQ ID NO:279 CloneB7 Heavy Chain HFR2
SEQ ID NO:280 CloneB7 Heavy Chain HFR3
SEQ ID NO:281 CloneB7 Heavy Chain HFR4
SEQ ID NO:282 CloneD7 Heavy Chain HFR1
SEQ ID NO:283 CloneD7 Heavy Chain HFR2
SEQ ID NO:284 CloneD7 Heavy Chain HFR3
SEQ ID NO:285 CloneD7 Heavy Chain HFR4
SEQ ID NO:286 CloneC10 Heavy Chain HFR1
SEQ ID NO:287 CloneC10 Heavy Chain HFR2
SEQ ID NO:288 CloneC10 Heavy Chain HFR3
SEQ ID NO:289 CloneC10 Heavy Chain HFR4
SEQ ID NO:290 CloneB8 Light Chain LFR1
SEQ ID NO:291 CloneB8 Light Chain LFR2
SEQ ID NO:292 CloneB8 Light Chain LFR3
SEQ ID NO:293 CloneB8 Light Chain LFR4
SEQ ID NO:294 CloneA11 Light Chain LFR1
SEQ ID NO:295 CloneA11 Light Chain LFR2
SEQ ID NO:296 CloneA11 Light Chain LFR3
SEQ ID NO:297 CloneA11 Light Chain LFR4
SEQ ID NO:298 CloneE10 Light Chain LFR1
SEQ ID NO:299 CloneE10 Light Chain LFR2
SEQ ID NO:300 CloneE10 Light Chain LFR3
SEQ ID NO:301 CloneE10 Light Chain LFR4

SEQ ID NO:302 CloneB7 Light Chain LFR1
SEQ ID NO:303 CloneB7 Light Chain LFR2
SEQ ID NO:304 CloneB7 Light Chain LFR3
SEQ ID NO:305 CloneB7 Light Chain LFR4
SEQ ID NO:306 CloneD7 Light Chain LFR1
SEQ ID NO:307 CloneD7 Light Chain LFR2
SEQ ID NO:308 CloneD7 Light Chain LFR3
SEQ ID NO:309 CloneD7 Light Chain LFR4
SEQ ID NO:310 CloneC10 Light Chain LFR1
SEQ ID NO:311 CloneC10 Light Chain LFR2
SEQ ID NO:312 CloneC10 Light Chain LFR3
SEQ ID NO:313 CloneC10 Light Chain LFR4
SEQ ID NO:314 CloneB8 Heavy Chain HFR1
SEQ ID NO:315 CloneB8 Heavy Chain HFR2
SEQ ID NO:316 CloneB8 Heavy Chain HFR3
SEQ ID NO:317 CloneB8 Heavy Chain HFR4
SEQ ID NO:318 CloneA11 Heavy Chain HFR1
SEQ ID NO:319 CloneA11 Heavy Chain HFR2
SEQ ID NO:320 CloneA11 Heavy Chain HFR3
SEQ ID NO:321 CloneA11 Heavy Chain HFR4
SEQ ID NO:322 CloneE10 Heavy Chain HFR1
SEQ ID NO:323 CloneE10 Heavy Chain HFR2
SEQ ID NO:324 CloneE10 Heavy Chain HFR3
SEQ ID NO:325 CloneE10 Heavy Chain HFR4
SEQ ID NO:326 CloneB7 Heavy Chain HFR1
SEQ ID NO:327 CloneB7 Heavy Chain HFR2
SEQ ID NO:328 CloneB7 Heavy Chain HFR3
SEQ ID NO:329 CloneB7 Heavy Chain HFR4
SEQ ID NO:330 CloneD7 Heavy Chain HFR1
SEQ ID NO:331 CloneD7 Heavy Chain HFR2
SEQ ID NO:332 CloneD7 Heavy Chain HFR3
SEQ ID NO:333 CloneD7 Heavy Chain HFR4
SEQ ID NO:334 CloneC10 Heavy Chain HFR1
SEQ ID NO:335 CloneC10 Heavy Chain HFR2
SEQ ID NO:336 CloneC10 Heavy Chain HFR3
SEQ ID NO:337 CloneC10 Heavy Chain HFR4
SEQ ID NO:338 CloneB8 Light Chain LFR1
SEQ ID NO:339 CloneB8 Light Chain LFR2
SEQ ID NO:340 CloneB8 Light Chain LFR3
SEQ ID NO:341 CloneB8 Light Chain LFR4
SEQ ID NO:342 CloneA11 Light Chain LFR1
SEQ ID NO:343 CloneA11 Light Chain LFR2
SEQ ID NO:344 CloneA11 Light Chain LFR3
SEQ ID NO:345 CloneA11 Light Chain LFR4
SEQ ID NO:346 CloneE10 Light Chain LFR1
SEQ ID NO:347 CloneE10 Light Chain LFR2
SEQ ID NO:348 CloneE10 Light Chain LFR3
SEQ ID NO:349 CloneE10 Light Chain LFR4
SEQ ID NO:350 CloneB7 Light Chain LFR1
SEQ ID NO:351 CloneB7 Light Chain LFR2
SEQ ID NO:352 CloneB7 Light Chain LFR3
SEQ ID NO:353 CloneB7 Light Chain LFR4
SEQ ID NO:354 CloneD7 Light Chain LFR1
SEQ ID NO:355 CloneD7 Light Chain LFR2
SEQ ID NO:356 CloneD7 Light Chain LFR3
SEQ ID NO:357 CloneD7 Light Chain LFR4
SEQ ID NO:358 CloneC10 Light Chain LFR1
SEQ ID NO:359 CloneC10 Light Chain LFR2
SEQ ID NO:360 CloneC10 Light Chain LFR3
SEQ ID NO:361 CloneC10 Light Chain LFR4

DETAILED DESCRIPTION

The present invention is at least partly based on the creation of a humanized, recombinant antibodies directed to EBV anti-gp350 that at least partly prevent or inhibit the binding of EBV gp350 to thereby block EBV entry into human cells. This humanized, recombinant antibody may be particularly suitable for administration to humans to passively immunize against EBV infection.

In a particular aspect, the invention provides a recombinant, human or humanized antibody or antibody fragment that is capable of at least partly preventing or inhibiting Epstein Barr Virus (EBV) gp350 binding to a human cell, to thereby block EBV entry into the human cell.

In another particular aspect, the invention provides an antibody or antibody fragment comprising at least one CDR amino acid sequence according to any one of SEQ ID NOS: 1-144 or present in any one of SEQ ID NOS: 145-156, that is preferably capable of at least partly preventing or inhibiting Epstein Barr Virus (EBV) gp350 binding to a human cell, to thereby block EBV entry into the human cell.

Preferably, the antibody or antibody fragment of these particular aspects is a neutralizing antibody.

In one embodiment, the antibody or antibody fragment of these aspects is produced by phage display.

As used herein, by "isolated" is meant material that has been removed from its natural state or otherwise been subjected to human manipulation. Isolated material may be substantially or essentially free from components that normally accompany it in its natural state, or may be manipulated so as to be in an artificial state together with components that normally accompany it in its natural state. Isolated material may be in recombinant, chemical synthetic, enriched, purified or partially purified form.

As used herein a "protein" is an amino acid polymer, wherein the amino acids may include D-amino acids, L-amino acids, natural and/or non-natural amino acids. As typically used herein, a "peptide" is a protein comprising no more than sixty (60) contiguous amino acids. As typically used herein, a "polypeptide" is a protein comprising more than sixty (60) contiguous amino acids. The term "protein" should also be understood to encompass protein-containing molecules such as glycoproteins and lipoproteins, although without limitation thereto.

As used herein, an "antibody" is or comprises an immunoglobulin protein. The term "immunoglobulin" includes any antigen-binding protein product of a mammalian immunoglobulin gene complex, including immunoglobulin isotypes IgA, IgD, IgM, IgG and IgE and antigen-binding fragments thereof. Included in the term "immunoglobulin" are immunoglobulins that are recombinant, chimeric or humanized or otherwise comprise altered or variant amino acid residues, sequences and/or glycosylation, whether naturally occurring or produced by human intervention (e.g. by recombinant DNA technology).

Generally, antibodies and antibody fragments may be polyclonal or monoclonal. It will also be appreciated that antibodies may be produced as recombinant synthetic antibodies or antibody fragments by expressing a nucleic acid encoding the antibody or antibody fragment in an appropriate host cell. Non-limiting examples of recombinant antibody expression and selection techniques, inclusive of phage display methods, are provided in Chapter 17 of Coligan et al., CURRENT PROTOCOLS IN IMMUNOLOGY and Zuberbuhler et al., 2009, Protein Engineering, Design & Selection 22 169. A non-limiting example of a phage display system for selecting anti-gp350 antibodies is provided hereinafter in the Examples.

Typically, an antibody comprises: respective light chain ($V_L$) and heavy chain ($V_H$) variable regions that each comprise complementarity determining region (CDR) 1, 2 and 3 amino acid sequences; and respective light chain ($C_L$) and heavy chain ($CH_1$, $CH_2$, $CH_3$) constant regions. CDR identification and numbering may be according to any known CDR numbering system inclusive of Kabat, Chothia, AbM and Contact. Non-limiting examples of CDR amino acid sequences are set forth in SEQ ID NOS: 1-144 and shown in Tables 1-12. CDR identification and numbering was performed using abYsis version 2.7.3 and IMGT/V-QUEST. SEQ ID NOS: 1-36 use Chothia numbering; SEQ ID NOS: 37-72 use AbM numbering; SEQ ID NOS: 73-108 use Kabat numbering; and SEQ ID NOS: 109-144 use Contact numbering. Antibodies according to the invention may comprise 1, 2 or 3 $V_L$ CDR amino acid sequences (e.g CDR1, CDR2 and/or CDR3) and/or 1, 2, or 3 $V_H$ CDR amino acid sequences (e.g CDR1, CDR2 and/or CDR3), such as preferably set forth in SEQ ID NOS: 1-144.

Antibody fragments include Fab and Fab'2 fragments, diabodies, triabodies, bi-specific antibodies and single chain antibody fragments (e.g. ScFvs), although without limitation thereto. In some embodiments, an antibody fragment may comprise at least a portion of a CDR1, 2 and/or 3 amino acid sequence, such as set forth in SEQ ID NOS: 1-36. A preferred antibody fragment comprises at least one entire light chain variable region CDR and/or at least one entire heavy chain variable region CDR.

As broadly used herein, "humanized" antibodies may include antibodies entirely or at least partly of human origin, inclusive of modified antibodies or antibody fragments obtained from a non-human "foreign" species. In some embodiments, antibodies and antibody fragments may be modified so as to be administrable to one species having being produced in, or originating from, the same or another "foreign" species without eliciting a deleterious immune response to the "foreign" antibody. Human or non-human antibody fragments such as comprising complementarity determining regions (CDRs) or variable regions (i.e $V_H$ and $V_L$ domains) may be "grafted" onto a human antibody scaffold or backbone to produce a "humanized" antibody or antibody fragment. In a particular embodiment, human or non-human CDRs or $V_L$ and $V_L$ domains are recombinantly grafted with a human antibody constant region, preferably a human $IgG_1$ constant region.

As disclosed herein in more detail in the Examples, human antibody $V_H$ and $V_L$ fragment-encoding nucleotide sequences were isolated by phage display and recombinantly grafted onto a human $IgG_1$ constant region "backbone".

A non-limiting example of a human $IgG_1$ constant region comprises the amino acid sequence TVSSASTKGPSVFP (SEQ ID NO:157), as originally described in Jones et al., 2010, J. Immunol. Methods 354 85.

Preferably, the antibody or antibody fragment is a neutralizing antibody or antibody fragment. By this is meant an antibody or antibody fragment that at least partly blocks, inhibits or reduces one or more infective or pathogenic properties of EBV. In a particular embodiment, the antibody or antibody fragment at least partly blocks, inhibits or reduces gp350-mediated entry of EBV into a human cell.

Suitably, the antibody or antibody fragment binds an epitope of an EBV gp350 protein. As generally used herein, an "epitope" is an antigenic protein fragment that comprises a continuous or discontinuous sequence of amino acids of a protein, wherein the epitope can be recognized or bound by an element of the immune system, such as an antibody or other antigen receptor.

The invention also includes variants of the antibody or antibody fragment disclosed herein, such as a CDR variant.

Suitably, an antibody or antibody fragment comprising at least one variant is capable of preventing Epstein Barr Virus (EBV) gp350 binding to a human cell.

In particular embodiments, a variant has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity with the amino acid sequence set forth in any one of SEQ ID NOS: 1-156. The protein "variant" disclosed herein may have one or more amino acids deleted or substituted by different amino acids. It is well understood in the art that some amino acids may be substituted or deleted without changing biological activity of the peptide (conservative substitutions).

In one embodiment, the variant is an antibody or antibody fragment comprising an amino acid sequence at least 70% identical to any one of SEQ ID NOS: 1-144, referred to herein as a CDR "variant". By way of example, CDR amino acid sequences may be altered to improve recognition and/or binding to EBV gp350.

In some embodiments, variants may be produced by recombinant mutagenesis techniques.

Terms used generally herein to describe sequence relationships between respective proteins and nucleic acids include "comparison window", "sequence identity", "percentage of sequence identity" and "substantial identity". Because respective nucleic acids/proteins may each comprise (1) only one or more portions of a complete nucleic acid/protein sequence that are shared by the nucleic acids/proteins, and (2) one or more portions which are divergent between the nucleic acids/proteins, sequence comparisons are typically performed by comparing sequences over a "comparison window" to identify and compare local regions of sequence similarity. A "comparison window" refers to a conceptual segment of typically 6, 9 or 12 contiguous residues that is compared to a reference sequence. The comparison window may comprise additions or deletions (i.e., gaps) of about 20% or less as compared to the reference sequence for optimal alignment of the respective sequences. Optimal alignment of sequences for aligning a comparison window may be conducted by computerised implementations of algorithms (Geneworks program by Intelligenetics; GAP, BESTFIT, FASTA, and TFASTA in the Wisconsin Genetics Software Package Release 7.0, Genetics Computer Group, 575 Science Drive Madison, WI, USA, incorporated herein by reference) or by inspection and the best alignment (i.e. resulting in the highest percentage homology over the comparison window) generated by any of the various methods selected. Reference also may be made to the BLAST family of programs as for example disclosed by Altschul et al., 1997, Nucl. Acids Res. 25 3389, which is incorporated herein by reference. A detailed discussion of sequence analysis can be found in Unit 19.3 of CURRENT PROTO-COLS IN MOLECULAR BIOLOGY Eds. Ausubel et al. (John Wiley & Sons Inc NY, 1995-2015).

The term "sequence identity" is used herein in its broadest sense to include the number of exact nucleotide or amino acid matches having regard to an appropriate alignment using a standard algorithm, having regard to the extent that sequences are identical over a window of comparison. Thus, a "percentage of sequence identity" is calculated by comparing two optimally aligned sequences over the window of comparison, determining the number of positions at which the identical nucleic acid base (e.g., A, T, C, G, I) occurs in both sequences to yield the number of matched positions, dividing the number of matched positions by the total number of positions in the window of comparison (i.e., the window size), and multiplying the result by 100 to yield the percentage of sequence identity. For example, "sequence identity" may be understood to mean the "match percentage" calculated by the DNASIS computer program (Version 2.5 for windows; available from Hitachi Software engineering Co., Ltd., South San Francisco, California, USA).

Derivatives of the antibody, antibody fragments or variants thereof disclosed herein are also provided.

As used herein, "derivative" antibodies, antibody fragments or variants thereof have been altered, for example by conjugation or complexing with other chemical moieties, by post-translational modification (e.g. phosphorylation, ubiquitination, glycosylation), chemical modification (e.g. cross-linking, acetylation, biotinylation, oxidation or reduction and the like), conjugation with labels (e.g. fluorophores, enzymes, radioactive isotopes) and/or inclusion of additional amino acid sequences as would be understood in the art.

In this regard, the skilled person is referred to Chapter 15 of CURRENT PROTOCOLS IN PROTEIN SCIENCE, Eds. Coligan et al. (John Wiley & Sons NY 1995-2015) for more extensive methodology relating to chemical modification of proteins.

Additional amino acid sequences may include fusion partner amino acid sequences which create a fusion protein. By way of example, fusion partner amino acid sequences may assist in detection and/or purification of the isolated fusion protein. Non-limiting examples include metal-binding (e.g. polyhistidine) fusion partners, maltose binding protein (MBP), Protein A, glutathione S-transferase (GST), fluorescent protein sequences (e.g. GFP), epitope tags such as myc, FLAG and haemagglutinin tags.

Another aspect of the invention provides an isolated nucleic acid encoding an antibody, antibody fragment or variant thereof disclosed herein.

As generally used herein a "nucleic acid" designates single- or double-stranded DNA and RNA. DNA includes genomic DNA and cDNA. RNA includes mRNA, RNA, RNAi, siRNA, CRNA and autocatalytic RNA. Nucleic acids may also be DNA-RNA hybrids. A nucleic acid comprises a nucleotide sequence which typically includes nucleotides that comprise an A, G, C, T or U base. However, nucleotide sequences may include other bases such as inosine, methylycytosine, methylinosine, methyladenosine and/or thiouridine, although without limitation thereto.

In a preferred form, the nucleotide sequence may be codon-optimized, by which is meant that the nucleotide sequence is a synthetic or engineered sequence, rather than the original "source" nucleotide sequence, modified for optimal expression in a particular host cell type by taking advantage of codon sequence variations or redundancies that occur across different cell types and/or species.

In some embodiments, the nucleic acid may be in a genetic construct that facilitates delivery and expression of the nucleic acid. Broadly, the genetic construct may be in the form of, or comprise genetic components of, a plasmid, a transposon, a bacteriophage, a virus, a cosmid, a yeast or bacterial artificial chromosome as are well understood in the art. Suitably, the nucleic acid is operably linked or connected to one or more elements of the construct that facilitate propagation, manipulation and/or expression of the genetic construct and/or nucleic acid. The one or more elements may include promoters, enhancers, polyadenylation sequences, splice donor/acceptor sites, multiple cloning sites, bacterial origins of replication, selection markers for bacterial, mammalian or other host cells, translation initiation and stop sequences, as are well known in the art. Promoters may be constitutive or inducible/repressible promoters as are well known in the art.

The choice of said one or more elements may be at least partly dependent on the host cell type used for expression, particularly according to the origin of the host cell (e.g. mammalian or other vertebrates, plant, bacterial, insect or yeast cells such as *E. coli*, CHO, COS, Vero, HeLa, HEK-293, Sf9 and *Pichia pastoris* host cells, although without limitation thereto).

It will be appreciated from the foregoing that an aspect of the invention provides a method of treating or preventing an EBV infection in a human, said method including the step of administering the antibody of the first aspect, the second aspect and/or the composition of the fourth aspect to the human to thereby treat or prevent an EBV infection in the human.

Another aspect of the invention provides a method of passively immunizing a human against an EBV infection, said method including the step of administering the antibody of the first aspect, the second aspect and/or the composition of the fourth aspect to the human to thereby passively immunizing the human against an EBV infection.

As generally used herein the terms "immunize", "vaccinate" and "vaccine" refer to antibodies, antibody fragments, methods and/or compositions that elicit or provide a protective immune response against EBV. Administration of said antibody or antibody fragment to human may be referred to as "passive" immunization which provides the human with at least temporary antibody-mediated immunity to an existing or potential EBV infection.

In certain embodiments the immune response may be suitable for preventing, treating or passively immunizing the human against EBV.

As used herein, "treating", "treat" or "treatment" refers to a therapeutic intervention that at least partly ameliorates, eliminates or reduces a symptom or pathological sign of an EBV infection after it has begun to develop. Treatment need not be absolute to be beneficial to the subject.

As used herein, "preventing", "prevent" or "prevention" refers to a course of action initiated prior to infection by, or exposure to, EBV or molecular components thereof and/or before the onset of a symptom or pathological sign of an EBV infection, so as to at least partly prevent infection and/or reduce the symptom or pathological sign. It is to be understood that such prevention need not be absolute or complete to be beneficial to a subject.

EBV is a common human pathogen and may cause, or be associated with, one or more diseases, disorders or conditions in humans. Thus, certain embodiments of the aforementioned methods relate to passively immunization, preventing and/or treating one or more diseases, disorders or conditions caused by, or associated with, an EBV infection in humans. EBV predominantly infects human hosts through epithelial cells and B lymphocytes where it can then establish long-term latency in the human host. Primary infection of EBV causes over 90% of cases of infectious mononucleosis (IM) worldwide, infecting mainly children and young adults through the expansion of EBV infected B cells. EBV has been associated with several cancers, including Burkitt and Hodgkin's lymphomas, gastric and nasopharyngeal carcinomas, lymphomas in HIV-infected individuals and post-transplant lymphoproliferative disorder (PTLD). EBV has also been found to be implicated in autoimmune diseases, particularly multiple sclerosis.

In this context, another aspect, the invention provides at least partly inhibiting or preventing EBV gp350 binding to a human cell, said method including the step of administering the antibody of the first aspect, the second aspect and/or the composition of the fourth aspect to the human to thereby at least partly inhibit or prevent EBV gp350 binding to a human cell. Suitably the human cell is a B lymphocyte.

In some embodiments, the isolated antibodies, fragments and/or variants, or combinations of these, may be administered to a mammal in the form of a composition comprising a pharmaceutically acceptable carrier, diluent or excipient.

It will be appreciated that pharmaceutically acceptable carriers, diluents and/or excipients may include solid, semi-solid, gel or liquid fillers, diluents or encapsulating substances that may be safely used in systemic administration. Depending upon the particular route of administration, carriers, diluents and/or excipients may be selected from a group including sugars, starches, cellulose and its derivatives, malt, gelatine, talc, calcium sulfate, vegetable oils, synthetic oils, polyols, alginic acid, isotonic saline, pyrogen-free water, wetting or emulsifying agents, bulking agents, glidants, coatings (e.g. enteric coatings), emollients, binders, fillers, disintegrants, lubricants, pH buffering agents (e.g. phosphate buffers) and/or flavouring agents, although without limitation thereto. The composition may be administered to a human in any one or more dosage forms that include tablets, dispersions, suspensions, injectable solutions, syrups, troches, capsules, suppositories, aerosols, transdermal patches and the like.

Administration of the antibody, antibody fragment or variant thereof, or an encoding nucleic acid, or a composition comprising same may be by any known parenteral, topical or enteral route inclusive of intravenous, intramuscular, intraperitoneal, intracranial, transdermal, oral, intranasal, anal and intra-ocular, although without limitation thereto.

The composition may further include one or more additional agents inclusive of adjuvants or other immunostimulants.

By "adjuvant" is meant an agent which assists, augments or otherwise facilitates the elicitation of an immune response. Non-limiting examples of adjuvants include Freund's adjuvant, aluminium hydroxide (alum), aluminium phosphate, squalene, IL-12, CpG-oligonucleotide, Montanide ISA720, imiquimod, SBAS2, SBAS4, MF59, MPL, Quil A, QS21 and ISCOMs.

For the purposes of methods of immunization, prevention and/or treatment of EBV infections, the recipient human may be referred to as a "subject" or "patient", which terms are used interchangeably.

As described herein, a preferred method of producing anti-gp350 antibodies or antibody fragments is by phage display, although other methods of antibody production may be utilized, as are well known in the art.

In one embodiment, "candidate" anti-gp350 antibodies or antibody fragments may subsequently be tested and selected according to their ability to bind gp350 and preferably prevent EBV gp350 binding to one or more of the B lymphocytes and thereby block entry of EBV into the human cell.

Accordingly, a further aspect of the invention provides method or system for determining the efficacy of an anti-EBV gp350 antibody or antibody fragment, said method or system comprising infecting a mouse with EBV, the mouse comprising human B lymphocytes, and determining the efficacy of a candidate anti-EBV agent in the mouse.

Suitably, the efficacy relates to, or includes, the ability of the candidate anti-EBV antibody or antibody fragment to prevent EBV gp350 binding to one or more of the B lymphocytes and thereby block entry of EBV into the human cell.

Suitably, the human B lymphocytes have been derived from human hematopoietic stem cells administered to the mouse. Preferably, the human hematopoietic stem cells are CD34. Typically, the mice are immunocompromised or immunodeficient mice. A non-limiting example is irradiated adult NOD scid gamma (NSG) mice.

Thus, it will be appreciated that the method or system provides a means whereby a mouse which has been engineered to adopt certain characteristics of the human immune system can thereby a model for testing the potential efficacy of an anti-EBV gp350 antibody to block EBV infection in humans.

In a particular embodiment, the method or system includes:

(i) administering CD34 human pluripotential stem cells to an immunocompromised or immunodeficient mouse;

(ii) allowing human B lymphocytes to develop from the CD34 human pluripotential stem cells;

(iii) infecting the mouse with EBV; and (iv) determining the ability of a candidate anti-EBV gp350 antibody or antibody fragment administered to the mouse to block EBV entry into the human B lymphocytes.

The antibodies or antibody fragments may be polyclonal, monoclonal, native or recombinant as hereinbefore described.

In another aspect, the invention provides a method of detecting EBVgp350 or a cell expressing EBVgp350, said method including the step of forming a complex between the antibody or antibody fragment of the first and/or second aspects and EBV gp350 to thereby detect EBVgp350 or the cell expressing EBVgp350.

This aspect relates to detection of gp350, such as by an EBV-infected cell.

It will therefore be understood that an antibody or antibody fragment disclosed herein may be used to assist medical diagnosis of EBV infection. Suitably, the method includes detecting gp350, such as when expressed by EBV-infected cells present in, or obtained from, a biological sample. In certain embodiments, the biological sample may be a pathology sample that comprises one or more fluids, cells, tissues, organs or organ samples obtained from a human. Non-limiting examples include blood, plasma, saliva, serum, lymphocytes, urine, faeces, amniotic fluid, cervical samples, cerebrospinal fluid, tissue biopsies, bone marrow and skin, although without limitation thereto.

In some embodiments, the antibody or antibody fragment is labeled.

The label may be selected from a group including biotin, avidin, digoxigenin, an enzyme (e.g alkaline phosphatase or horseradish peroxidase), a fluorophore (e.g. FITC, Texas Red, Coumarin), a radioisotope (e.g. $^{125}I$, $^{131}I$, $^{67}Ga$, $^{111}In$) and/or a direct visual label (e.g. a gold particle), although without limitation thereto.

Suitably, detection of gp350 includes the step of forming a detectable complex between an antibody or antibody fragment and gp350 or a cell expressing gp350. The complex so formed may be detected by any technique, assay or means known in the art including immunoblotting, immunohistochemistry, immunocytochemistry, immunoprecipitation, ELISA, flow cytometry, magnetic bead separation, biosensor-based detection systems such as surface plasmon resonance and imaging such as PET imaging, although without limitation thereto.

To facilitate detection the antibody may be directly labeled as hereinbefore described or a labeled secondary antibody may be used. The labels may be as hereinbefore described.

In some embodiments, a detection kit may be provided which comprises an antibody or antibody fragment disclosed herein together with one or more detection reagents such as enzymes, enzyme substrates (e.g Luminol, AMPPD, NBT), secondary antibodies and/or magnetic beads although without limitation thereto.

So that preferred embodiments may be described in detail and put into practical effect, reference is made to the following non-limiting Examples.

EXAMPLES

The Generation of EBV-Specific Gp350 Neutralising Monoclonal Antibodies

To explore the ability to produce neutralising anti-gp350 antibodies and determine their effect against gp350, the aim was to first generate a panel of EBV-specific gp350 monoclonal antibodies. Monoclonal antibodies were generated using two different approaches. The first approach generated gp350-specific mouse hybridomas. The second approach generated recombinant anti-gp350 antibodies through a phage display system.

(i) Murine Monoclonal Antibodies Via Hybridomas

To generate gp350-specific mouse hybridomas, mice were immunized with a combination of gp350 antigen and an immune adjuvant (Sigma-Aldrich cat #S6322) and methylated CpG. Serum samples were collected from the immunized mice and reactivity to the antigen was tested by ELISA at a dilution of 1:250 and 1:1250 and compared to a pre-immunization sample. Animals with the highest anti-gp350 antibody titre were selected for the generation of hybridomas.

To generate hybridoma cells the mouse spleen was excised, dissociated into a single cell suspension and fused to SP2/0-Ag14 myeloma cells using polyethylene glycol. ELISA analysis was used to screen nine hybridoma supernatants for their reactivity to gp350. Of the nine that were screened, two clones with the highest absorbance reading F1 (OD 450 nm: 21) and G1 (OD 450 nm: 15.1) were selected for further subcloning rounds to generate murine monoclonal antibodies.

After subsequent subcloning rounds, an ELISA which tested the supernatants of each subclone at 2-fold dilutions revealed four subclones with the highest reactivity against gp350. These subclones were selected and expanded into larger volumes for purification in order to generate monoclonal antibodies.

Figure 1:
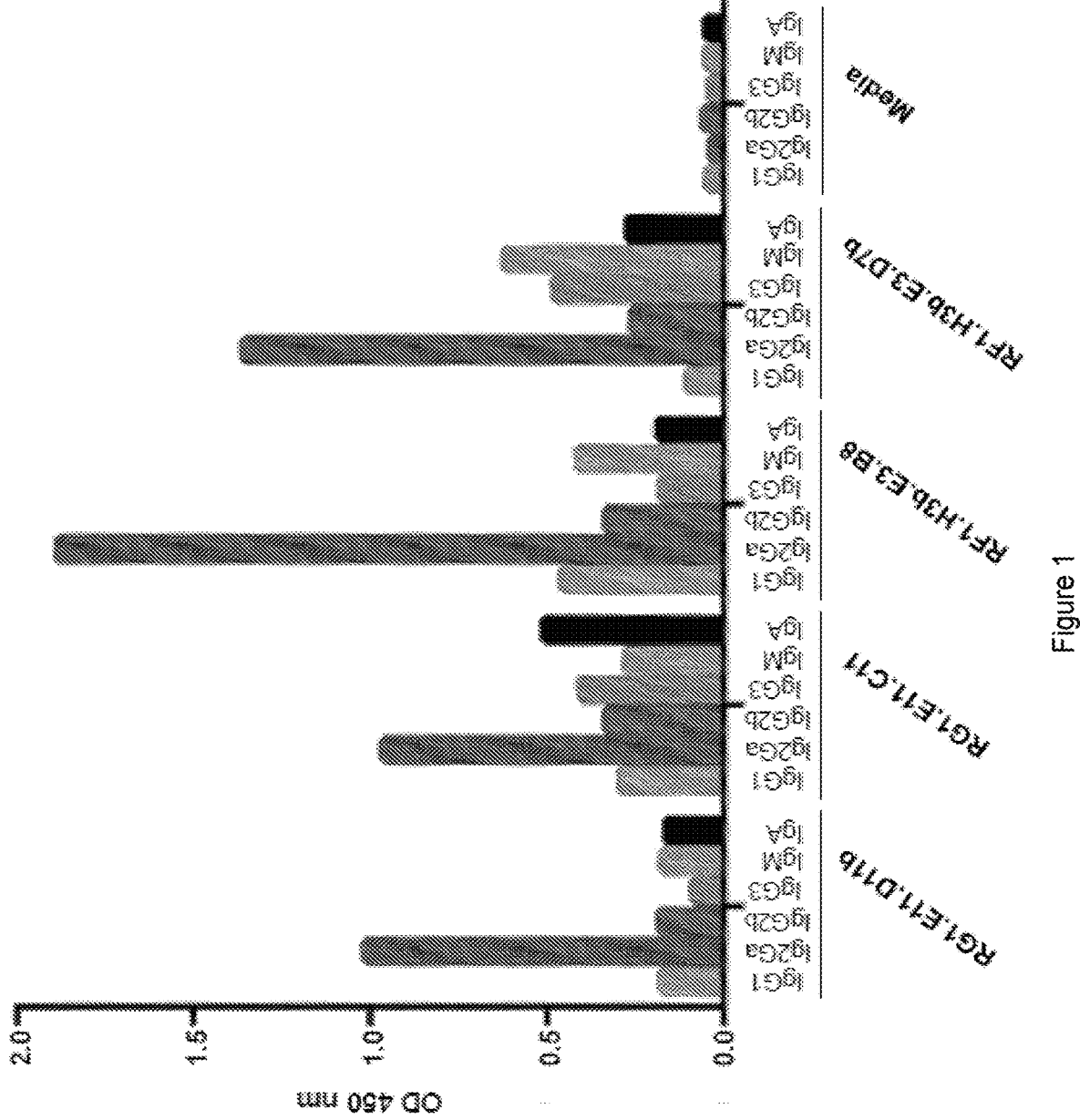
FIG. 1: Immunoglobulin isotype analysis of four murine monoclonal subclones (RG1.E11.D11b, RG1.E11.C11, RF1.H3b.E3.B8 and RF1.H3b.E3.D7b) specific for gp350 antigen.

To generate purified monoclonal antibodies, the isotypes of the four subclones were determined by performing a mouse antibody isotype ELISA where each subclone was tested against six mouse immunoglobulin isotype-specific monoclonal antibodies. Analysis shows that all subclones were positively reactive to IgG2a (FIG. 1), which enabled purification of these subclone supernatants using a protein G column.

A protein G column (Sigma-Aldrich cat #ge17-0405-01) was used for the purification, in which 200 mL of supernatant from each subclone was passed through the column and eluted to generate purified gp350-specific murine monoclonal antibodies. ELISA analysis revealed that subclone RG1.E11.D11b generated 521 μg/mL of purified monoclonal antibody, RG1.E11.C11 eluted 111 μg/mL, RF1.H3b.E3.B8 generated 479 μg/mL and RF1.H3b.E3.D7b contained 374 μg/mL. We then assessed whether both approaches post production of murine and humanized monoclonal antibodies are capable of neutralising EBV infection. A preliminary test of the gp350-specific monoclonal antibodies for their EBV neutralizing ability was performed. Monoclonal antibodies and serum obtained from a seropositive donor were tested at 2-fold dilutions with PBMCs (Peripheral Blood Mononuclear Cells) at $2\times10^5$ cells per well, from a sera-negative donor against B95-8 (infectious mononucleosis-derived isolate of EBV) in a 96-well plate format. The neutralization assay was performed in quadruplicate, and the plate was left to incubate for a duration of 6 weeks. Neutralization was determined by analyzing whether each antibody neutralized B cell transformation by EBV infection. It was found that none of the murine monoclonal antibodies were able to neutralize EBV and thus failed to block transformation of B cells (FIGS. 2A&B).

(ii) Generation of Human Gp350-Specific Antibodies Using Antibody Phage Display (ADP) Platform Technology This second approach was aimed to generate fully functional recombinant human monoclonal antibodies through antibody phage display which is based on genetic engineering of bacteriophages and repeated rounds of antigen-guided selection and phage propagation. In this procedure, a library of purified phage having DNA inserts from peripheral blood B lymphocytes obtained from healthy human donors was exposed to gp350 in order to isolate a pool of phage particles that bind specifically to glycoprotein gp350. Phage particles remaining after washing away non-binders are then harvested and used to infect *E. coli* bacteria for amplification (FIG. 3). This procedure was repeated 4 times to enrich the pool with specific binders to gp350. A polyclonal ELISA was then performed to determine the round with enriched binders specific to gp350 (FIG. 4). The ELISA involves immobilizing gp350 onto microtiter plates, followed by the addition of various dilutions of the phage pool from each round, and then detection of bound phage using an anti-M13 phage HRP antibody.

As the objective was to obtain monoclonal antibodies, individual clones from the fourth round of bio-panning was isolated from cell glycerol stocks. This procedure involved growing single colonies from the cell glycerol stocks onto 4×150 mm 2YT-Ampicillin Glucose (2%) plates overnight, after which single cell colonies were individually plated onto a 96-well plate. Helper phage was added to each well of the 96-well plate to induce the production of phage particles. Phage particles from each clone were then tested via monoclonal phage ELISA for specific binding to gp350. Of the 96 clones, it was found that 44 were positive (absorbance >1) to gp350. The CDR sequences of all 44 positive clones were analyzed and six (6) clones were found to be uniquely positive to gp350.

PCR amplification products encoding $V_H$ and $V_L$ fragments were produced from the original six (6) phage clones. The translated CDR sequences shown in Tables 1-12 (SEQ ID NOS: 1-144) were identified and numbered using abYsis version 2.7.3 and IMGT/V-QUEST. These unique six (6) clones were used to generate fully functional human monoclonal antibodies by antibody reformatting with a human IgG₁ backbone (FIGS. 5A&B; SEQ ID NOS: 145-156). The human IgG constant region comprises the amino acid sequence TVSSASTKGPSVFP (SEQ ID NO:157), as originally described in Jones et al., 2010, J. Immunol. Methods, supra These recombinant human monoclonal antibodies were then expressed using a mammalian expression system. Target DNA sequence encoding each of full-length antibody sequences were optimized, synthesized and sub-cloned into pcDNA3.4 vector. The recombinant plasmids encoding target antibody were transiently co-transfected into suspension Expi293F cell cultures. The cell culture supernatants collected on day 6 were used for purification. Cell culture supernatants were centrifuged and followed by filtration. These filtered cell culture supernatants were loaded onto affinity purification column at an appropriate flowrate. After washing and elution with appropriate buffer, the eluted fractions were pooled and buffer exchanged to final formulation buffer. The purified protein was analyzed by SDS-PAGE, Western blotting and SEC-HPLC analysis for molecular weight and purity measurements.

Figure 7B:
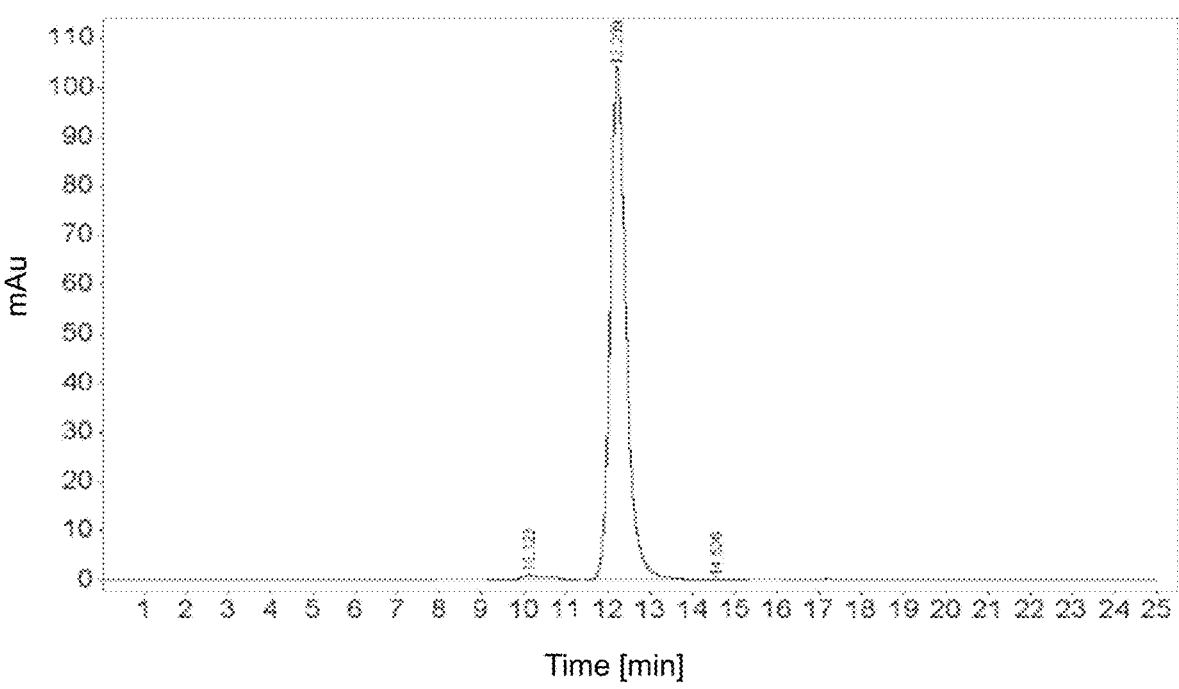

Representative data for Clone B8 and Clone B7 are presented FIGS. 6 and 7. These antibodies were tested for their capacity to neutralise EBV and block proliferation of EBV-infected B cells. Data presented in FIG. 8 shows that all antibody clones E10, A11, B7, D10 and D7 showed strong inhibition of EBV infection while B8 clone showed no neutralization.

Biophysical Analysis of Humanized Monoclonal Antibodies Bound to Gp350 Via Surface Plasmon Resonance Surface Plasmon Resonance (SPR) analysis of gp350 glycoprotein and humanized monoclonal antibodies was performed using the Biacore T100 system (GE Healthcare). CM5 sensor chips were used with 1×PBS as the running buffer, at a flow rate of 30 μL/min. Glycoprotein gp350 was immobilised onto the flow cells of the sensor chip with a capture level of 1243RU with a flow rate of 10 μL/min, a flow cell of the sensor chip was left blank for referencing of the sensograms. Single cycle kinetics was then used to determine the dissociation constant ($K_d$) for each humanized monoclonal antibody against gp350, with concentrations ranging from 25 μg/mL to 1.2 mg/mL with 1:2 dilution series. A flow rate of 40 μL/min was used for the duration of the experiment, with contact time of 120 seconds and 600 seconds for the dissociation time per antibody for each of their concentrations. The regeneration of the surface was achieved using 10 mM glycine buffer pH 2.1 with a 30 second injection at 30 μL/min.

Single cycle kinetic binding curves (FIG. 10) show the dissociation constants of each antibody against gp350. Antibody A11 with the lowest $K_D$ value of 0.723 nM has the best dissociation constant, with the ability to stay bound to gp350 during contact time, it also has the best affinity constant of $3.090E^{-7}$ M (FIG. 11). Antibody B7 had a low dissociation value of 4.06754 nM and an affinity value of $7.683E^{-7}$M, although it is not the lowest dissociation and affinity constant values in comparison to A11, D7 (3.862 nM, $4.651E^{-7}$M) and E10 (2.2293 nM, $6.635E^{-7}$ M), it is important to outline previous data which shows that B7 had the best gp350 neutralising capacity in vitro compared to C10, D7 and E10. B7 is also capable of maintaining low levels of dissociation throughout constant exposure to harsh surface regeneration buffers known to denature antibodies and proteins. Interestingly, antibody B8 which had the highest dissociation constant of 33.3209 nM, as well as a high affinity constant of $8.286E^{-7}$ M did not show any neutralising ability in vitro and can be observed to quickly dissociate once bound to gp350.

Assessing the Therapeutic Efficacy of Humanized Antibodies Against EBV Infected Humanized Mice Referring to the schematic shown in FIG. 9, the therapeutic efficacy of the humanized antibodies against humanized mice infected with EBV was assessed by twice irradiating adult (6-10 weeks) NOD SCID Gamma (NSG) mice and intravenously injecting them with human hematopoietic stem cells (CD34) to reconstitute human immunity. These mice were assessed every 4 weeks for the percentage of lymphocytes present via flow cytometry and maintained for 12 weeks post injection. The humanized mice were then intraperitoneally injected with EBV, where viral loads for each mouse was monitored weekly using quantitative PCR for up to 4 weeks post EBV injection. Three treatment groups were assessed by utilising EBV gp350 specific neutralising antibody (B7), EBV gp350 specific non-neutralising antibody (B8) and a control PBS group. Each group which consisted of 6 mice (n=18) received 100 μg intravenously of the appropriate antibody 5 and 10 days post EBV injection (FIG. 9). Mice were sacrificed 4 weeks post EBV injects and their spleens were harvested for histochemical staining via EBER.

Virus loads for each treatment group was monitored using quantitative PCR, which shows B7 (0.052 copies/mL) and B8 (0.047 copies/mL) with significantly decreased viral loads compared to PBS (97.196 copies/mL) treated mice group on day 28, p<0.0001 (FIG. 12A). This correlates with histochemical stains where spleens were harvested and stained for the presence EBER (EBV-encoded RNA) in tissues (FIG. 12B). Remarkably, mice that were given the B7 EBV neutralising antibody treatment showed almost no signs of EBER in the spleen tissues compared to mice treated with B8 EBV non-neutralising antibody and PBS (FIG. 12B).

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

All computer programs, algorithms, patent and scientific literature referred to herein is incorporated herein by reference.

REFERENCES

Coghill, A. E. and A. Hildesheim (2014). "Epstein-Barr Virus Antibodies and the Risk of Associated Malignancies: Review of the Literature." *American Journal of Epidemiology* 180(7): 687-695.

Gu, S. Y., T. M. Huang, L. Ruan, Y. H. Miao, H. Lu, C. M. Chu, M. Motz and H. Wolf (1995). "First EBV vaccine trial in humans using recombinant vaccinia virus expressing the major membrane antigen." *Dev Biol Stand* 84:171-177.

Haque, T., I. Johannessen, D. Dombagoda, C. Sengupta, D. M. Burns, P. Bird, G. Hale, G. Mieli-Vergani and D. H. Crawford (2006). "A mouse monoclonal antibody against Epstein-Barr virus envelope glycoprotein 350 prevents infection both in vitro and in vivo." *J Infect Dis* 194(5): 584-587.

Moutschen, M., P. Leonard, E. M. Sokal, F. Smets, M. Haumont, P. Mazzu, A. Bollen, F. Denamur, P. Peeters, G. Dubin and M. Denis (2007). "Phase I/II studies to evaluate safety and immunogenicity of a recombinant gp350 Epstein-Barr virus vaccine in healthy adults." *Vaccine* 25(24): 4697-4705.

Sashihara, J., Y. Hoshino, J. J. Bowman, T. Krogmann, P. D. Burbelo, V. M. Coffield, K. Kamrud and J. I. Cohen (2011). "Soluble rhesus lymphocryptovirus gp350 protects against infection and reduces viral loads in animals that become infected with virus after challenge." *PLOS Pathog* 7(10): e1002308.

Szakonyi, G., M. G. Klein, J. P. Hannan, K. A. Young, R. Z. Ma, R. Asokan, V. M. Holers and X. S. Chen (2006). "Structure of the Epstein-Barr virus major envelope glycoprotein." *Nat Struct Mol Biol* 13(11): 996-1001.

TABLE 1

| | | CloneB8 Heavy Chain CDR1, 2 and 3 amino acid sequences. | | |
|---|---|---|---|---|
| Region | Definition | Sequence Fragment | Residues | SEQ ID NO: |
| HFR1 | Chothia | EVQLVESAGEVQKPGESLRISCKAS----- | 1-25 | 170 |
| | AbM | EVQLVESAGEVQKPGESLRISCKAS----- | 1-25 | 218 |
| | Kabat | EVQLVESAGEVQKPGESLRISCKASGYTFS | 1-30 | 266 |
| | Contact | EVQLVESAGEVQKPGESLRISCKASGYTF- | 1-29 | 314 |
| CDR-H1 | Chothia | GYTFSHY--- | 26-32 | 1 |
| | AbM | GYTFSHYWIG | 26-35 | 37 |
| | Kabat | -----HYWIG | 31-35 | 73 |
| | Contact | ----SHYWIG | 30-35 | 109 |
| HFR2 | Chothia | WIGWVRQLPGKGLEWMGII | 33-51 | 171 |
| | AbM | ---WVRQLPGKGLEWMG-- | 36-49 | 219 |
| | Kabat | ---WVRQLPGKGLEWMG-- | 36-49 | 267 |
| | Contact | ---WVRQLPGKGLE----- | 36-46 | 315 |
| CDR-H2 | Chothia | -----YPDDSD--------- | 52-57 | 2 |
| | AbM | ---IIYPDDSDSR------- | 50-59 | 38 |
| | Kabat | ---IIYPDDSDSRYSPSFQG | 50-66 | 74 |
| | Contact | WMGIIYPDDSDSR------- | 47-59 | 110 |
| HFR3 | Chothia | SRYSPSFQGQVTMSVDKSINTAYLQWNSLKVSDTATYYCVR | 58-98 | 172 |
| | AbM | --YSPSFQGQVTMSVDKSINTAYLQWNSLKVSDTATYYCVR | 60-98 | 220 |
| | Kabat | --------QVTMSVDKSINTAYLQWNSLKVSDTATYYCVR | 67-98 | 268 |
| | Contact | --YSPSFQGQVTMSVDKSINTAYLQWNSLKVSDTATYYC-- | 60-96 | 316 |
| CDR-H3 | Chothia | --HWLKRGSNFGFGFDP | 99-113 | 3 |
| | AbM | --HWLKRGSNFGFGFDP | 99-113 | 39 |
| | Kabat | --HWLKRGSNFGFGFDP | 99-113 | 75 |
| | Contact | VRHWLKRGSNFGFGFD- | 97-112 | 111 |

TABLE 1-continued

CloneB8 Heavy Chain CDR1, 2 and 3 amino acid sequences.

| Region | Definition | Sequence Fragment | Residues | SEQ ID NO: |
|--------|-----------|-------------------|----------|------------|
| HFR4 | Chothia | -WGQGTTLTVSS | 114-124 | 173 |
| | AbM | -WGQGTTLTVSS | 114-124 | 221 |
| | Kabat | -WGQGTTLTVSS | 114-124 | 269 |
| | Contact | PWGQGTTLTVSS | 113-124 | 317 |

TABLE 2

CloneB8 Light Chain CDR1, 2 and 3 amino acid sequences

| Region | Definition | Sequence Fragment | Residues | SEQ ID NO: |
|--------|-----------|-------------------|----------|------------|
| LFR1 | Chothia | ESALTQPASVSGSPGQSITISC------ | 1-22 | 194 |
| | AbM | ESALTQPASVSGSPGQSITISC------ | 1-22 | 242 |
| | Kabat | ESALTQPASVSGSPGQSITISC----- | 1-22 | 290 |
| | Contact | ESALTQPASVSGSPGQSITISCTGTSSD | 1-28 | 338 |
| CDR-L1 | Chothia | TGTSSDVGGYNYVS-- | 23-36 | 19 |
| | AbM | TGTSSDVGGYNYVS-- | 23-36 | 55 |
| | Kabat | TGTSSDVGGYNYVS-- | 23-36 | 91 |
| | Contact | ------VGGYNYVSWY | 29-38 | 127 |
| LFR2 | Chothia | WYQQHPGKAPKLMIY | 37-51 | 195 |
| | AbM | WYQQHPGKAPKLMIY | 37-51 | 243 |
| | Kabat | WYQQHPGKAPKLMIY | 37-51 | 291 |
| | Contact | --QQHPGKAPK---- | 39-47 | 339 |
| CDR-L2 | Chothia | ----DVSNRPS | 52-58 | 20 |
| | AbM | ----DVSNRPS | 52-58 | 56 |
| | Kabat | ----DVSNRPS | 52-58 | 92 |
| | Contact | LMIYDVSNRP- | 48-57 | 128 |
| LFR3 | Chothia | -GVSNRFSGSKSGNTASLTISGLQAEDEADYYC | 59-90 | 196 |
| | AbM | -GVSNRFSGSKSGNTASLTISGLQAEDEADYYC | 59-90 | 244 |
| | Kabat | -GVSNRFSGSKSGNTASLTISGLQAEDEADYYC | 59-90 | 292 |
| | Contact | SGVSNRFSGSKSGNTASLTISGLQAEDEADYYC | 58-90 | 340 |
| CDR-L3 | Chothia | SSYTSSSTLV | 91-100 | 21 |
| | AbM | SSYTSSSTLV | 91-100 | 57 |
| | Kabat | SSYTSSSTLV | 91-100 | 93 |
| | Contact | SSYTSSSTL- | 91-99 | 129 |
| LFR4 | Chothia | -FGGGTKLTVLG | 101-111 | 197 |
| | AbM | -FGGGTKLTVLG | 101-111 | 245 |
| | Kabat | -FGGGTKLTVLG | 101-111 | 293 |
| | Contact | VFGGGTKLTVLG | 100-111 | 341 |

TABLE 3

CloneA11 Heavy Chain CDR1, 2 and 3 amino acid sequences.

| Region | Definition | Sequence Fragment | Residues | SEQ ID NO: |
|--------|-----------|-------------------|----------|------------|
| HFR1 | Chothia | MQLVQSGAEVKKPGASVKVSCKTS----- | 1-24 | 174 |
| | AbM | MQLVQSGAEVKKPGASVKVSCKTS----- | 1-24 | 222 |
| | Kabat | MQLVQSGAEVKKPGASVKVSCKTSGYNFN | 1-29 | 270 |
| | Contact | MQLVQSGAEVKKPGASVKVSCKTSGYNF- | 1-28 | 318 |
| CDR-H1 | Chothia | GYNFNHQ--- | 25-31 | 4 |
| | AbM | GYNFNHQGIS | 25-34 | 40 |
| | Kabat | -----HQGIS | 30-34 | 76 |
| | Contact | ----NHQGIS | 29-34 | 112 |

TABLE 3-continued

| | CloneA11 Heavy Chain CDR1, 2 and 3 amino acid sequences. | | | |
|---|---|---|---|---|
| Region | Definition | Sequence Fragment | Residues | SEQ ID NO: |
| HFR2 | Chothia | GISWLRQAPGQGLEWMGWI | 32-50 | 175 |
| | AbM | ---WLRQAPGQGLEWMG-- | 35-48 | 223 |
| | Kabat | ---WLRQAPGQGLEWMG-- | 35-48 | 271 |
| | Contact | ---WLRQAPGQGLE----- | 35-45 | 319 |
| CDR-H2 | Chothia | -----SGFNGK--------- | 51-56 | 5 |
| | AbM | ---WISGFNGKTN------- | 49-58 | 41 |
| | Kabat | ---WISGFNGKTNYAQKFQG | 49-65 | 77 |
| | Contact | WMGWISGFNGKTN------- | 46-58 | 113 |
| HFR3 | Chothia | TNYAQKFQGRVTMTADRSTTTAYMELRSLRSDDTAVYYCAS | 57-97 | 176 |
| | AbM | --YAQKFQGRVTMTADRSTTTAYMELRSLRSDDTAVYYCAS | 59-97 | 224 |
| | Kabat | ---------RVTMTADRSTTTAYMELRSLRSDDTAVYYCAS | 66-97 | 272 |
| | Contact | --YAQKFQGRVTMTADRSTTTAYMELRSLRSDDTAVYYC-- | 59-95 | 320 |
| CDR-H3 | Chothia | --GGEQWLVQNFVH | 98-109 | 6 |
| | AbM | --GGEQWLVQNFVH | 98-109 | 42 |
| | Kabat | --GGEQWLVQNFVH | 98-109 | 78 |
| | Contact | ASGGEQWLVQNFV- | 96-108 | 114 |
| HFR4 | Chothia | -WGQGTLLTVSS | 110-120 | 177 |
| | AbM | -WGQGTLLTVSS | 110-120 | 225 |
| | Kabat | -WGQGTLLTVSS | 110-120 | 273 |
| | Contact | HWGQGTLLTVSS | 109-120 | 321 |

TABLE 4

| | CloneA11 Light Chain CDR1, 2 and 3 amino acid sequences | | | |
|---|---|---|---|---|
| Region | Definition | Sequence Fragment | Residues | SEQ ID NO: |
| LFR1 | Chothia | VLTQEPSLTVSPGGTVTLTC------ | 1-20 | 198 |
| | AbM | VLTQEPSLTVSPGGTVTLTC------ | 1-20 | 246 |
| | Kabat | VLTQEPSLTVSPGGTVTLTC------ | 1-20 | 294 |
| | Contact | VLTQEPSLTVSPGGTVTLTCASSTGA | 1-26 | 342 |
| CDR-L1 | Chothia | ASSTGAVTSGYYPN-- | 21-34 | 22 |
| | AbM | ASSTGAVTSGYYPN-- | 21-34 | 58 |
| | Kabat | ASSTGAVTSGYYPN-- | 21-34 | 94 |
| | Contact | ------VTSGYYPNWF | 27-36 | 130 |
| LFR2 | Chothia | WFQQKPGQAPRALIY | 35-49 | 199 |
| | AbM | WFQQKPGQAPRALIY | 35-49 | 247 |
| | Kabat | WFQQKPGQAPRALIY | 35-49 | 295 |
| | Contact | --QQKPGQAPR---- | 37-45 | 343 |
| CDR-L2 | Chothia | ----STSNKHS | 50-56 | 23 |
| | AbM | ----STSNKHS | 50-56 | 59 |
| | Kabat | ----STSNKHS | 50-56 | 95 |
| | Contact | ALIYSTSNKH- | 46-55 | 131 |
| LFR3 | Chothia | -WTPARFSGSLLGGKAALTLSGVQPEDEAEYYC | 57-88 | 200 |
| | AbM | -WTPARFSGSLLGGKAALTLSGVQPEDEAEYYC | 57-88 | 248 |
| | Kabat | -WTPARFSGSLLGGKAALTLSGVQPEDEAEYYC | 57-88 | 296 |
| | Contact | SWTPARFSGSLLGGKAALTLSGVQPEDEAEYYC | 56-88 | 344 |
| CDR-L3 | Chothia | LLYYGGAWV | 89-97 | 24 |
| | AbM | LLYYGGAWV | 89-97 | 60 |
| | Kabat | LLYYGGAWV | 89-97 | 96 |
| | Contact | LLYYGGAW- | 89-96 | 132 |
| LFR4 | Chothia | -FGGGTKLTVL | 98-107 | 201 |
| | AbM | -FGGGTKLTVL | 98-107 | 249 |
| | Kabat | -FGGGTKLTVL | 98-107 | 297 |
| | Contact | VFGGGTKLTVL | 97-107 | 345 |

TABLE 5

| | | CloneE10 Heavy Chain CDR1, 2 and 3 amino acid sequences | | |
|---|---|---|---|---|
| Region | Definition | Sequence Fragment | Residues | SEQ ID NO: |
| HFR1 | Chothia | EVQLVQSGAEVKKPGASVEVSCKAS----- | 1-25 | 178 |
| | AbM | EVQLVQSGAEVKKPGASVEVSCKAS----- | 1-25 | 226 |
| | Kabat | EVQLVQSGAEVKKPGASVEVSCKASGYTFN | 1-30 | 274 |
| | Contact | EVQLVQSGAEVKKPGASVEVSCKASGYTF- | 1-29 | 322 |
| CDR-H1 | Chothia | GYTFNAY--- | 26-32 | 7 |
| | AbM | GYTFNAYYIH | 26-35 | 43 |
| | Kabat | -----AYYIH | 31-35 | 79 |
| | Contact | ----NAYYIH | 30-35 | 115 |
| HFR2 | Chothia | YIHWVRQAPGQGLDWMGWI | 33-51 | 179 |
| | AbM | ---WVRQAPGQGLDWMG-- | 36-49 | 227 |
| | Kabat | ---WVRQAPGQGLDWMG-- | 36-49 | 275 |
| | Contact | ---WVRQAPGQGLD----- | 36-46 | 323 |
| CDR-H2 | Chothia | -----NPNSGG--------- | 52-57 | 8 |
| | AbM | ---WINPNSGGTN------- | 50-59 | 44 |
| | Kabat | ---WINPNSGGTNYAQNFKG | 50-66 | 80 |
| | Contact | WMGWINPNSGGTN------- | 47-59 | 116 |
| HFR3 | Chothia | TNYAQNFKGRVTMTRDTSISTAYLELRSLTSDDTAVYFCAT | 58-98 | 180 |
| | AbM | --YAQNFKGRVTMTRDTSISTAYLELRSLTSDDTAVYFCAT | 60-98 | 228 |
| | Kabat | ---------RVTMTRDTSISTAYLELRSLTSDDTAVYFCAT | 67-98 | 276 |
| | Contact | --YAQNFKGRVTMTRDTS1STAYLELRSLTSDDTAVYFC-- | 60-96 | 324 |
| CDR-H3 | Chothia | --ERGYTSSFRRDAFDK | 99-113 | 9 |
| | AbM | --ERGYTSSFRRDAFDK | 99-113 | 45 |
| | Kabat | --ERGYTSSFRRDAFDK | 99-113 | 81 |
| | Contact | ATERGYTSSFRRDAFD- | 97-112 | 117 |
| HFR4 | Chothia | -WGQGTLLTVSS | 114-124 | 181 |
| | AbM | -WGQGTLLTVSS | 114-124 | 229 |
| | Kabat | -WGQGTLLTVSS | 114-124 | 277 |
| | Contact | KWGQGTLLTVSS | 113-124 | 325 |

35

TABLE 6

| | | CloneE10 Light Chain CDR1, 2 and 3 amino acid sequences. | | |
|---|---|---|---|---|
| Region | Definition | Sequence Fragment | Residues | SEQ ID NO: |
| LFR1 | Chothia | ESVLTQPPSISAAPGQRVTIPC------ | 1-22 | 202 |
| | AbM | ESVLTQPPSISAAPGQRVTIPC------ | 1-22 | 250 |
| | Kabat | ESVLTQPPSISAAPGQRVTIPC------ | 1-22 | 298 |
| | Contact | ESVLTQPPSISAAPGQRVTIPCSGSSSD | 1-28 | 346 |
| CDR-L1 | Chothia | SGSSSDIGNHYVS-- | 23-35 | 25 |
| | AbM | SGSSSDIGNHYVS-- | 23-35 | 61 |
| | Kabat | SGSSSDIGNHYVS-- | 23-35 | 97 |
| | Contact | ------IGNHYVSWY | 29-37 | 133 |
| LFR2 | Chothia | WYQQLPGAAPKLLIY | 36-50 | 203 |
| | AbM | WYQQLPGAAPKLLIY | 36-50 | 251 |
| | Kabat | WYQQLPGAAPKLLIY | 36-50 | 299 |
| | Contact | --QQLPGAAPK---- | 38-46 | 347 |
| CDR-L2 | Chothia | ----EDNKRPS | 51-57 | 26 |
| | AbM | ----EDNKRPS | 51-57 | 62 |
| | Kabat | ----EDNKRPS | 51-57 | 98 |
| | Contact | LLIYEDNKRP- | 47-56 | 134 |
| LFR3 | Chothia | -GIPDRFSGSKSGTSASLGITGLQTGDEADYYC | 58-89 | 204 |
| | AbM | -GIPDRFSGSKSGTSASLGITGLQTGDEADYYC | 58-89 | 252 |
| | Kabat | -GIPDRFSGSKSGTSASLGITGLQTGDEADYYC | 58-89 | 300 |
| | Contact | SGIPDRFSGSKSGTSASLGITGLQTGDEADYYC | 57-89 | 348 |
| CDR-L3 | Chothia | GTWDNSLRSGF | 90-100 | 27 |
| | AbM | GTWDNSLRSGF | 90-100 | 63 |
| | Kabat | GTWDNSLRSGF | 90-100 | 99 |
| | Contact | GTWDNSLRSG- | 90-99 | 135 |

TABLE 6-continued

| Region | Definition | Sequence Fragment | Residues | SEQ ID NO: |
|--------|-----------|-------------------|----------|------------|
| | CloneE10 Light Chain CDR1, 2 and 3 amino acid sequences. | | | |
| LFR4 | Chothia | -FGGGTKVTVLG | 101-111 | 205 |
| | AbM | -FGGGTKVTVLG | 101-111 | 253 |
| | Kabat | -FGGGTKVTVLG | 101-111 | 301 |
| | Contact | FFGGGTKVTVLG | 100-111 | 349 |

TABLE 7

| Region | Definition | Sequence Fragment | Residues | SEQ ID NO: |
|--------|-----------|-------------------|----------|------------|
| | CloneB7 Heavy Chain CDR1, 2 and 3 amino acid sequences. | | | |
| HFR1 | Chothia | EVQLVQSGAEVKKPGASVEVSCKAS----- | 1-25 | 182 |
| | AbM | EVQLVQSGAEVKKPGASVEVSCKAS----- | 1-25 | 230 |
| | Kabat | EVQLVQSGAEVKKPGASVEVSCKASGYTFN | 1-30 | 278 |
| | Contact | EVQLVQSGAEVKKPGASVEVSCKASGYTF- | 1-29 | 326 |
| CDR-H1 | Chothia | GYTFNAY--- | 26-32 | 10 |
| | AbM | GYTFNAYYIH | 26-35 | 46 |
| | Kabat | -----AYYIH | 31-35 | 82 |
| | Contact | ----NAYYIH | 30-35 | 118 |
| HFR2 | Chothia | YIHWVRQAPGQGLDWMGWI | 33-51 | 183 |
| | AbM | ---WVRQAPGQGLDWMG-- | 36-49 | 231 |
| | Kabat | ---WVRQAPGQGLDWMG-- | 36-49 | 279 |
| | Contact | ---WVRQAPGQGLD----- | 36-46 | 327 |
| CDR-H2 | Chothia | -----NPNSGG--------- | 52-57 | 11 |
| | AbM | ---WINPNSGGTN------- | 50-59 | 47 |
| | Kabat | ---WINPNSGGTNYAQNFKG | 50-66 | 83 |
| | Contact | WMGWINPNSGGTN------- | 47-59 | 119 |
| HFR3 | Chothia | TNYAQNFKGRVTMTRDTSISTAYLELRSLTSDDTAVYFCAT | 58-98 | 184 |
| | AbM | --YAQNFKGRVTMTRDTSISTAYLELRSLTSDDTAVYFCAT | 60-98 | 232 |
| | Kabat | ---------RVTMTRDTSISTAYLELRSLTSDDTAVYFCAT | 67-98 | 280 |
| | Contact | --YAQNFKGRVTMTRDTSISTAYLELRSLTSDDTAVYFC-- | 60-96 | 328 |
| CDR-H3 | Chothia | --ERGYTSSFRRDAFDK | 99-113 | 12 |
| | AbM | --ERGYTSSFRRDAFDK | 99-113 | 48 |
| | Kabat | --ERGYTSSFRRDAFDK | 99-113 | 84 |
| | Contact | ATERGYTSSFRRDAFD- | 97-112 | 120 |
| HFR4 | Chothia | -WGQGTMLTVSS | 114-124 | 185 |
| | AbM | -WGQGTMLTVSS | 114-124 | 233 |
| | Kabat | -WGQGTMLTVSS | 114-124 | 281 |
| | Contact | KWGQGTMLTVSS | 113-124 | 329 |

TABLE 8

| Region | Definition | Sequence Fragment | Residues | SEQ ID NO: |
|--------|-----------|-------------------|----------|------------|
| | CloneB7 Light Chain CDR1, 2 and 3 amino acid sequences | | | |
| LFR1 | Chothia | ESVLTQPPSVSAAPGQKVTISC------ | 1-22 | 206 |
| | AbM | ESVLTQPPSVSAAPGQKVTISC------ | 1-22 | 254 |
| | Kabat | ESVLTQPPSVSAAPGQKVTISC------ | 1-22 | 302 |
| | Contact | ESVLTQPPSVSAAPGQKVTISCSGSSSN | 1-28 | 350 |
| CDR-L1 | Chothia | SGSSSNIGNNYVS-- | 23-35 | 28 |
| | AbM | SGSSSNIGNNYVS-- | 23-35 | 64 |
| | Kabat | SGSSSNIGNNYVS-- | 23-35 | 100 |
| | Contact | ------IGNNYVSWY | 29-37 | 136 |

TABLE 8-continued

| Region | Definition | Sequence Fragment | Residues | SEQ ID NO: |
|--------|-----------|-------------------|----------|------------|

CloneB7 Light Chain CDR1, 2 and 3 amino acid sequences

| Region | Definition | Sequence Fragment | Residues | SEQ ID NO: |
|--------|-----------|-------------------|----------|------------|
| LFR2 | Chothia | WYQQLPGTAPKLLIY | 36-50 | 207 |
| | AbM | WYQQLPGTAPKLLIY | 36-50 | 255 |
| | Kabat | WYQQLPGTAPKLLIY | 36-50 | 303 |
| | Contact | --QQLPGTAPK---- | 38-46 | 351 |
| CDR-L2 | Chothia | ----ENNKRPS | 51-57 | 29 |
| | AbM | ----ENNKRPS | 51-57 | 65 |
| | Kabat | ----ENNKRPS | 51-57 | 101 |
| | Contact | LLIYENNKRP- | 47-56 | 137 |
| LFR3 | Chothia | -GIPDRFSGSKSGTSATLGITGLQTGDEAGYYC | 58-89 | 208 |
| | AbM | -GIPDRFSGSKSGTSATLGITGLQTGDEAGYYC | 58-89 | 256 |
| | Kabat | -GIPDRFSGSKSGTSATLGITGLQTGDEAGYYC | 58-89 | 304 |
| | Contact | SGIPDRFSGSKSGTSATLGITGLQTGDEAGYYC | 57-89 | 352 |
| CDR-L3 | Chothia | GTWDSSLSAVV | 90-100 | 30 |
| | AbM | GTWDSSLSAVV | 90-100 | 66 |
| | Kabat | GTWDSSLSAVV | 90-100 | 102 |
| | Contact | GTWDSSLSAV- | 90-99 | 138 |
| LFR4 | Chothia | -FGGGTKLTVLG | 101-111 | 209 |
| | AbM | -FGGGTKLTVLG | 101-111 | 257 |
| | Kabat | -FGGGTKLTVLG | 101-111 | 305 |
| | Contact | VFGGGTKLTVLG | 100-111 | 353 |

TABLE 9

CloneD7 Heavy Chain CDR1, 2 and 3 amino acid sequences.

| Region | Definition | Sequence Fragment | Residues | SEQ ID NO: |
|--------|-----------|-------------------|----------|------------|
| HFR1 | Chothia | EVQLVQSGAEVKKPGASVEVSCKAS----- | 1-25 | 186 |
| | AbM | EVQLVQSGAEVKKPGASVEVSCKAS----- | 1-25 | 234 |
| | Kabat | EVQLVQSGAEVKKPGASVEVSCKASGYTFN | 1-30 | 282 |
| | Contact | EVQLVQSGAEVKKPGASVEVSCKASGYTF- | 1-29 | 330 |
| CDR-H1 | Chothia | GYTFNAY--- | 26-32 | 13 |
| | AbM | GYTFNAYYIH | 26-35 | 49 |
| | Kabat | -----AYYIH | 31-35 | 85 |
| | Contact | ----NAYYIH | 30-35 | 121 |
| HFR2 | Chothia | YIHWVRQAPGQGLDWMGWI | 33-51 | 187 |
| | AbM | ---WVRQAPGQGLDWMG-- | 36-49 | 235 |
| | Kabat | ---WVRQAPGQGLDWMG-- | 36-49 | 283 |
| | Contact | ---WVRQAPGQGLD----- | 36-46 | 331 |
| CDR-H2 | Chothia | -----NPNSGG--------- | 52-57 | 14 |
| | AbM | ---WINPNSGGTN------- | 50-59 | 50 |
| | Kabat | ---WINPNSGGTNYAQNFKG | 50-66 | 85 |
| | Contact | WMGWINPNSGGTN------- | 47-59 | 122 |
| HFR3 | Chothia | TNYAQNFKGRVTMTRDTSISTAYLELRSLTSDDTAVYFCAT | 58-98 | 188 |
| | AbM | --YAQNFKGRVTMTRDTSISTAYLELRSLTSDDTAVYFCAT | 60-98 | 236 |
| | Kabat | ---------RVTMTRDTSISTAYLELRSLTSDDTAVYFCAT | 67-98 | 284 |
| | Contact | --YAQNFKGRVTMTRDTSISTAYLELRSLTSDDTAVYFC-- | 60-96 | 332 |
| CDR-H3 | Chothia | --ERGYTSSFRRDAFDK | 99-113 | 15 |
| | AbM | --ERGYTSSFRRDAFDK | 99-113 | 51 |
| | Kabat | --ERGYTSSFRRDAFDK | 99-113 | 87 |
| | Contact | ATERGYTSSFRRDAFD- | 97-112 | 123 |
| HFR4 | Chothia | -WGQGTMLTVSS | 114-124 | 189 |
| | AbM | -WGQGTMLTVSS | 114-124 | 237 |
| | Kabat | -WGQGTMLTVSS | 114-124 | 285 |
| | Contact | KWGQGTMLTVSS | 113-124 | 333 |

TABLE 10

| | CloneD7 Light Chain CDR1, 2 and 3 amino acid sequences. | | | |
|---|---|---|---|---|
| Region | Definition | Sequence Fragment | Residues | SEQ ID NO: |
| LFR1 | Chothia | ESVLTQPPSVSAAPGQKVTMSC------ | 1-22 | 210 |
| | AbM | ESVLTQPPSVSAAPGQKVTMSC------ | 1-22 | 258 |
| | Kabat | ESVLTQPPSVSAAPGQKVTMSC------ | 1-22 | 306 |
| | Contact | ESVLTQPPSVSAAPGQKVTMSCSGSTSN | 1-28 | 354 |
| CDR-L1 | Chothia | SGSTSNIGSNSVS-- | 23-35 | 31 |
| | AbM | SGSTSNIGSNSVS-- | 23-35 | 67 |
| | Kabat | SGSTSNIGSNSVS-- | 23-35 | 103 |
| | Contact | ------IGSNSVSWY | 29-37 | 139 |
| LFR2 | Chothia | WYQHLPGTAPKLLLF | 36-50 | 211 |
| | AbM | WYQHLPGTAPKLLLF | 36-50 | 259 |
| | Kabat | WYQHLPGTAPKLLLF | 36-50 | 307 |
| | Contact | --QHLPGTAPK---- | 38-46 | 355 |
| CDR-L2 | Chothia | ----DNAKRPS | 51-57 | 32 |
| | AbM | ----DNAKRPS | 51-57 | 68 |
| | Kabat | ----DNAKRPS | 51-57 | 104 |
| | Contact | LLLFDNAKRP- | 47-56 | 140 |
| LFR3 | Chothia | -GIPDRFSGSKSGTSATLGITGLQTGDEADYYC | 58-89 | 212 |
| | AbM | -GIPDRFSGSKSGTSATLGITGLQTGDEADYYC | 58-89 | 260 |
| | Kabat | -GIPDRFSGSKSGTSATLGITGLQTGDEADYYC | 58-89 | 308 |
| | Contact | SGIPDRFSGSKSGTSATLGITGLQTGDEADYYC | 57-89 | 356 |
| CDR-L3 | Chothia | GTWDSGLSVMV | 90-100 | 33 |
| | AbM | GTWDSGLSVMV | 90-100 | 69 |
| | Kabat | GTWDSGLSVMV | 90-100 | 105 |
| | Contact | GTWDSGLSVM- | 90-99 | 141 |
| LFR4 | Chothia | -FGGGTKLTVLG | 101-111 | 213 |
| | AbM | -FGGGTKLTVLG | 101-111 | 261 |
| | Kabat | -FGGGTKLTVLG | 101-111 | 309 |
| | Contact | VFGGGTKLTVLG | 100-111 | 357 |

35

TABLE 11

| | CloneC10 Heavy Chain CDR1, 2 and 3 amino acid sequences. | | | |
|---|---|---|---|---|
| Region | Definition | Sequence Fragment | Residues | SEQ ID NO: |
| HFR1 | Chothia | EVQLVQSGAEVKKPGASVKVSCKAS----- | 1-25 | 190 |
| | AbM | EVQLVQSGAEVKKPGASVKVSCKAS----- | 1-25 | 238 |
| | Kabat | EVQLVQSGAEVKKPGASVKVSCKASGYTFN | 1-30 | 286 |
| | Contact | EVQLVQSGAEVKKPGASVKVSCKASGYTF- | 1-29 | 334 |
| CDR-H1 | Chothia | GYTFNAY--- | 26-32 | 16 |
| | AbM | GYTFNAYYIH | 26-35 | 52 |
| | Kabat | -----AYYIH | 31-35 | 88 |
| | Contact | ----NAYYIH | 30-35 | 124 |
| HFR2 | Chothia | YIHWVRQAPGQGLDWMGWI | 33-51 | 191 |
| | AbM | ---WVRQAPGQGLDWMG-- | 36-49 | 239 |
| | Kabat | ---WVRQAPGQGLDWMG-- | 36-49 | 287 |
| | Contact | ---WVRQAPGQGLD----- | 36-46 | 335 |
| CDR-H2 | Chothia | -----NPNSGG--------- | 52-57 | 17 |
| | AbM | ---WINPNSGGTN------- | 50-59 | 53 |
| | Kabat | ---WINPNSGGTNYAQNFKG | 50-66 | 89 |
| | Contact | WMGWINPNSGGTN------- | 47-59 | 125 |
| HFR3 | Chothia | TNYAQNFKGRVTMTRDTSISTAYLELRSLTSDDTAVYFCAT | 58-98 | 192 |
| | AbM | --YAQNFKGRVTMTRDTSISTAYLELRSLTSDDTAVYFCAT | 60-98 | 240 |
| | Kabat | ---------RVTMTRDTSISTAYLELRSLTSDDTAVYFCAT | 67-98 | 288 |
| | Contact | --YAQNFKGRVTMTRDTSISTAYLELRSLTSDDTAVYFC-- | 60-96 | 336 |
| CDR-H3 | Chothia | --ERGYTSSFRRDAFDK | 99-113 | 18 |
| | AbM | --ERGYTSSFRRDAFDK | 99-113 | 54 |
| | Kabat | --ERGYTSSFRRDAFDK | 99-113 | 90 |
| | Contact | ATERGYTSSFRRDAFD- | 97-112 | 126 |

TABLE 11-continued

| | | CloneC10 Heavy Chain CDR1, 2 and 3 amino acid sequences. | | |
|---|---|---|---|---|
| Region | Definition | Sequence Fragment | Residues | SEQ ID NO: |
| HFR4 | Chothia | -WGQGTMLTVSS | 114-124 | 193 |
| | AbM | -WGQGTMLTVSS | 114-124 | 241 |
| | Kabat | -WGQGTMLTVSS | 114-124 | 289 |
| | Contact | KWGQGTMLTVSS | 113-124 | 337 |

TABLE 12

| | | CloneC10 Light Chain CDR1, 2 and 3 amino acid sequences. | | |
|---|---|---|---|---|
| Region | Definition | Sequence Fragment | Residues | SEQ ID NO: |
| LFR1 | Chothia | EAVVTQPPSASGTPGQGVTISC------ | 1-22 | 214 |
| | AbM | EAVVTQPPSASGTPGQGVTISC------ | 1-22 | 262 |
| | Kabat | EAVVTQPPSASGTPGQGVTISC------ | 1-22 | 310 |
| | Contact | EAVVTQPPSASGTPGQGVTISCSGSSSN | 1-28 | 358 |
| CDR-L1 | Chothia | SGSSSNIGSNFVY-- | 23-35 | 34 |
| | AbM | SGSSSNIGSNFVY-- | 23-35 | 70 |
| | Kabat | SGSSSNIGSNFVY-- | 23-35 | 106 |
| | Contact | ------IGSNFVYWY | 29-37 | 142 |
| LFR2 | Chothia | WYQQLPGTAPKLLIY | 36-50 | 215 |
| | AbM | WYQQLPGTAPKLLIY | 36-50 | 263 |
| | Kabat | WYQQLPGTAPKLLIY | 36-50 | 311 |
| | Contact | --QQLPGTAPK---- | 38-46 | 359 |
| CDR-L2 | Chothia | ----RNNQRPS | 51-57 | 35 |
| | AbM | ----RNNQRPS | 51-57 | 71 |
| | Kabat | ----RNNQRPS | 51-57 | 107 |
| | Contact | LLIYRNNQRP- | 47-56 | 143 |
| LFR3 | Chothia | -GVPDRFSGSKSATSASLAISGLRSEDEADYYC | 58-89 | 216 |
| | AbM | -GVPDRFSGSKSATSASLAISGLRSEDEADYYC | 58-89 | 264 |
| | Kabat | -GVPDRFSGSKSATSASLAISGLRSEDEADYYC | 58-89 | 312 |
| | Contact | SGVPDRFSGSKSATSASLAISGLRSEDEADYYC | 57-89 | 360 |
| CDR-L3 | Chothia | ATWDDSLSGYV | 90-100 | 36 |
| | AbM | ATWDDSLSGYV | 90-100 | 72 |
| | Kabat | ATWDDSLSGYV | 90-100 | 108 |
| | Contact | ATWDDSLSGY- | 90-99 | 144 |
| LFR4 | Chothia | -FGTGTKLTVLG | 101-111 | 217 |
| | AbM | -FGTGTKLTVLG | 101-111 | 265 |
| | Kabat | -FGTGTKLTVLG | 101-111 | 313 |
| | Contact | VFGTGTKLTVLG | 100-111 | 361 |

The invention claimed is:

1. A recombinant, human or humanized antibody or antibody fragment that is capable of at least partly reducing or inhibiting Epstein Barr Virus (EBV) gp350 binding to a human cell, which comprises six complementarity determining regions (CDR)s comprising a HCDR1, HCDR2, HCDR3, LCDR1, LCDR2, and LCDR3 selected from:

| Clone | CDR | SEQ ID NO: |
|---|---|---|
| B8 | HCDR1 | 1 (Chothia), 37 (AbM), 73 (Kabat), 109 |
| | HCDR2 | 2 (Chothia), 38 (AbM), 74 (Kabat), 110 |
| | HCDR3 | 3 (Chothia), 39 (AbM), 75 (Kabat), 111 |
| | LCDR1 | 19 (Chothia), 55 (AbM), 91 (Kabat), 127 |
| | LCDR2 | 20 (Chothia), 56 (AbM), 92 (Kabat), 128 |
| | LCDR3 | 21 (Chothia), 57 (AbM), 93 (Kabat), 129; or |
| A11 | HCDR1 | 4 (Chothia), 40 (AbM), 76 (Kabat), 112 |
| | HCDR2 | 5 (Chothia), 41 (AbM), 77 (Kabat), 113 |
| | HCDR3 | 6 (Chothia), 42 (AbM), 78 (Kabat), 114 |
| | LCDR1 | 22 (Chothia), 58 (AbM), 94 (Kabat), 130 |
| | LCDR2 | 23 (Chothia), 59 (AbM), 95 (Kabat), 131 |
| | LCDR3 | 24 (Chothia), 60 (AbM), 96 (Kabat), 132 (Contact) |
| E10 | HCDR1 | 7 (Chothia), 43 (AbM), 79 (Kabat), 115 (Contact) |
| | HCDR2 | 8 (Chothia), 44 (AbM), 80 (Kabat), 116 (Contact) |
| | HCDR3 | 9 (Chothia), 45 (AbM), 81 (Kabat), 117 (Contact) |
| | LCDR1 | 25 (Chothia), 61 (AbM), 97 (Kabat), 133 (Contact) |
| | LCDR2 | 26 (Chothia), 62 (AbM), 98 (Kabat), 134 (Contact) |
| | LCDR3 | 27 (Chothia), 63 (AbM), 99 (Kabat), 135 (Contact) |
| B7 | HCDR1 | 10 (Chothia), 46 (AbM), 82 (Kabat), 118 (Contact) |
| | HCDR2 | 11 (Chothia), 47 (AbM), 83 (Kabat), 119 (Contact) |
| | HCDR3 | 12 (Chothia), 48 (AbM), 84 (Kabat), 120 (Contact) |
| | LCDR1 | 28 (Chothia), 64 (AbM), 100 (Kabat), 136 (Contact) |
| | LCDR2 | 29 (Chothia), 65 (AbM), 101 (Kabat), 137 (Contact) |
| | LCDR3 | 30 (Chothia), 66 (AbM), 102 (Kabat), 138 (Contact) |
| D7 | HCDR1 | 13 (Chothia), 49 (AbM), 85 (Kabat), 121 (Contact) |
| | HCDR2 | 14 (Chothia), 50 (AbM), 86 (Kabat), 122 (Contact) |
| | HCDR3 | 15 (Chothia), 51 (AbM), 87 (Kabat), 123 (Contact) |
| | LCDR1 | 31 (Chothia), 67 (AbM), 103 (Kabat), 139 (Contact) |
| | LCDR2 | 32 (Chothia), 68 (AbM), 104 (Kabat), 140 (Contact) |
| | LCDR3 | 33 (Chothia), 69 (AbM), 105 (Kabat), 141 (Contact) |
| C10 | HCDR1 | 16 (Chothia), 52 (AbM), 88 (Kabat), 124 (Contact) |
| | HCDR2 | 17 (Chothia), 53 (AbM), 89 (Kabat), 125 (Contact) |
| | HCDR3 | 18 (Chothia), 54 (AbM), 90 (Kabat), 126 (Contact) |
| | LCDR1 | 34 (Chothia), 70 (AbM), 106 (Kabat), 142 (Contact) |

-continued

| Clone | CDR | SEQ ID NO: |
|---|---|---|
| | LCDR2 | 35 (Chothia), 71 (AbM), 107 (Kabat), 143 (Contact) |
| | LCDR3 | 36 (Chothia), 72 (AbM), 108, 144 (Contact). |

2. The recombinant human or humanized antibody or antibody fragment of claim 1, produced by phage display wherein the phage comprise one or more nucleotide sequences of human origin encoding one or more amino acid sequence of the human or humanized antibody or antibody fragment.

3. The recombinant human or humanized antibody or antibody fragment of claim 1, which comprises, consists essentially of or consists of an amino acid sequence set forth in any one of SEQ ID NOS: 145-156, or an amino acid sequence at least 90% identical thereto.

4. The recombinant, human or humanized antibody or antibody fragment of claim 1, further comprising a human IgG1 constant region amino acid sequence.

5. An antibody or antibody fragment comprising a heavy chain (VH) variable region sequence and a light chain (VL) variable region sequence selected from:

| Clone | Chain | SEQ ID NO: |
|---|---|---|
| B8 | VH | 145 |
| | VL | 151 |
| A11 | VH | 146 |
| | VL | 152 |
| E10 | VH | 147 |
| | VL | 153 |
| B7 | VH | 148 |
| | VL | 154 |
| D7 | VH | 149 |
| | VL | 155 |
| C10 | VH | 150 |
| | VL | 156 | wherein the VH variable region sequence according to any one of SEQ ID NOs: 145-150 has an amino acid sequence at least 90% identical thereto, and wherein the light chain (VL) variable region sequence according to any one of SEQ ID NOS: 151-156 or an amino acid sequence at least 90% identical thereto; wherein the HCDR1, HCDR2, HCDR3, LCDR1, LCDR2, and LCDR3 animo acid sequences are selected from:

| Clone | CDR | SEQ ID NO: |
|---|---|---|
| B8 | HCDR1 | 1 (Chothia), 37 (AbM), 73 (Kabat), 109 |
| | HCDR2 | 2 (Chothia), 38 (AbM), 74 (Kabat), 110 |
| | HCDR3 | 3 (Chothia), 39 (AbM), 75 (Kabat), 111 |
| | LCDR1 | 19 (Chothia), 55 (AbM), 91 (Kabat), 127 |
| | LCDR2 | 20 (Chothia), 56 (AbM), 92 (Kabat), 128 |
| | LCDR3 | 21 (Chothia), 57 (AbM), 93 (Kabat), 129; or |
| A11 | HCDR1 | 4 (Chothia), 40 (AbM), 76 (Kabat), 112 |
| | HCDR2 | 5 (Chothia), 41 (AbM), 77 (Kabat), 113 |
| | HCDR3 | 6 (Chothia), 42 (AbM), 78 (Kabat), 114 |

-continued

| Clone | CDR | SEQ ID NO: |
|---|---|---|
| | LCDR1 | 22 (Chothia), 58 (AbM), 94 (Kabat), 130 |
| | LCDR2 | 23 (Chothia), 59 (AbM), 95 (Kabat), 131 |
| | LCDR3 | 24 (Chothia), 60 (AbM), 96 (Kabat), 132 (Contact) |
| E10 | HCDR1 | 7 (Chothia), 43 (AbM), 79 (Kabat), 115 (Contact) |
| | HCDR2 | 8 (Chothia), 44 (AbM), 80 (Kabat), 116 (Contact) |
| | HCDR3 | 9 (Chothia), 45 (AbM), 81 (Kabat), 117 (Contact) |
| | LCDR1 | 25 (Chothia), 61 (AbM), 97 (Kabat), 133 (Contact) |
| | LCDR2 | 26 (Chothia), 62 (AbM), 98 (Kabat), 134 (Contact) |
| | LCDR3 | 27 (Chothia), 63 (AbM), 99 (Kabat), 135 (Contact) |
| B7 | HCDR1 | 10 (Chothia), 46 (AbM), 82 (Kabat), 118 (Contact) |
| | HCDR2 | 11 (Chothia), 47 (AbM), 83 (Kabat), 119 (Contact) |
| | HCDR3 | 12 (Chothia), 48 (AbM), 84 (Kabat), 120 (Contact) |
| | LCDR1 | 28 (Chothia), 64 (AbM), 100 (Kabat), 136 (Contact) |
| | LCDR2 | 29 (Chothia), 65 (AbM), 101 (Kabat), 137 (Contact) |
| | LCDR3 | 30 (Chothia), 66 (AbM), 102 (Kabat), 138 (Contact) |
| D7 | HCDR1 | 13 (Chothia), 49 (AbM), 85 (Kabat), 121 (Contact) |
| | HCDR2 | 14 (Chothia), 50 (AbM), 86 (Kabat), 122 (Contact) |
| | HCDR3 | 15 (Chothia), 51 (AbM), 87 (Kabat), 123 (Contact) |
| | LCDR1 | 31 (Chothia), 67 (AbM), 103 (Kabat), 139 (Contact) |
| | LCDR2 | 32 (Chothia), 68 (AbM), 104 (Kabat), 140 (Contact) |
| | LCDR3 | 33 (Chothia), 69 (AbM), 105 (Kabat), 141 (Contact) |
| C10 | HCDR1 | 16 (Chothia), 52 (AbM), 88 (Kabat), 124 (Contact) |
| | HCDR2 | 17 (Chothia), 53 (AbM), 89 (Kabat), 125 (Contact) |
| | HCDR3 | 18 (Chothia), 54 (AbM), 90 (Kabat), 126 (Contact) |
| | LCDR1 | 34 (Chothia), 70 (AbM), 106 (Kabat), 142 (Contact) |
| | LCDR2 | 35 (Chothia), 71 (AbM), 107 (Kabat), 143 (Contact) |

-continued

| Clone | CDR | SEQ ID NO: |
|---|---|---|
| | LCDR3 | 36 (Chothia), 72 (AbM), 108, 144 (Contact). |

6. The antibody or antibody fragment of claim 5, wherein the VH sequence consists essentially of or consists of an amino acid sequence set forth in any one of SEQ ID NOS: 145-150, and the VL sequence consists essentially of or consists of an amino acid sequence set forth in any one of SEQ ID NOS: 151-156.

7. The antibody or antibody fragment of claim 5, produced by phage display wherein the phage comprise one or more nucleotide sequences of human origin encoding one or more amino acid sequences of the human or humanized antibody or antibody fragment.

8. The antibody or antibody fragment according to claim 5, which is capable of at least partly preventing or inhibiting EBV gp350 binding to a human cell.

9. An isolated nucleic acid encoding a recombinant, human or humanized antibody or antibody fragment according to claim 1.

10. A genetic construct comprising the isolated nucleic acid of claim 9.

11. A host cell comprising the genetic construct of claim 10.

12. A composition comprising a recombinant, human or humanized antibody or antibody fragment according to claim 1, and a pharmaceutically acceptable carrier diluent or excipient.

13. A method of treating an EBV infection in a human, said method including the step of administering a composition comprising a recombinant, human or humanized antibody or antibody fragment according to claim 1 to the human to thereby treat an EBV infection in the human.

14. A method of at least partly inhibiting EBV gp350 binding to a human cell, said method including the step of administering a recombinant, human humanized antibody or antibody fragment according to claim 1 to the human to thereby at least partly inhibit EBV gp350 binding to a human cell.

15. A method of detecting EBVgp350 or a cell expressing EBVgp350, said method including the step of forming a complex between a recombinant, human or humanized antibody or antibody fragment according to claim 1 and EBV gp350 to thereby detect EBVgp350 or the cell expressing EBVgp350, wherein the antibody or antibody fragment is labeled.

\* \* \* \* \*

SEQUENCE LISTING

<160> NUMBER OF SEQ ID NOS: 361

<210> SEQ ID NO 1
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 1

Gly Tyr Thr Phe Ser His Tyr
1               5

<210> SEQ ID NO 2

```
<211> LENGTH: 6
<212> TYPE: PRT
<213> ORGANISM: Artificial sequence
<220> FEATURE:
<223> OTHER INFORMATION: Antibody CDR fragment

<400> SEQUENCE: 2

Tyr Pro Asp Asp Ser Asp
1               5

<210> SEQ ID NO 3
<211> LENGTH: 15
<212> TYPE: PRT
<213> ORGANISM: Artificial sequence
<220> FEATURE:
<223> OTHER INFORMATION: Antibody CDR fragment

<400> SEQUENCE: 3

His Trp Leu Lys Arg Gly Ser Asn Phe Gly Phe Gly Phe Asp Pro
1               5                   10                  15

<210> SEQ ID NO 4
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 4

Gly Tyr Asn Phe Asn His Gln
1               5

<210> SEQ ID NO 5
<211> LENGTH: 6
<212> TYPE: PRT
<213> ORGANISM: Artificial sequence
<220> FEATURE:
<223> OTHER INFORMATION: Antibody CDR fragment

<400> SEQUENCE: 5

Ser Gly Phe Asn Gly Lys
1               5

<210> SEQ ID NO 6
<211> LENGTH: 12
<212> TYPE: PRT
<213> ORGANISM: Artificial sequence
<220> FEATURE:
<223> OTHER INFORMATION: Antibody CDR fragment

<400> SEQUENCE: 6

Gly Gly Glu Gln Trp Leu Val Gln Asn Phe Val His
1               5                   10

<210> SEQ ID NO 7
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 7

Gly Tyr Thr Phe Asn Ala Tyr
1               5

<210> SEQ ID NO 8
<211> LENGTH: 6
```

```
<212> TYPE: PRT
<213> ORGANISM: Artificial sequence
<220> FEATURE:
<223> OTHER INFORMATION: Antibody CDR fragment

<400> SEQUENCE: 8

Asn Pro Asn Ser Gly Gly
1               5

<210> SEQ ID NO 9
<211> LENGTH: 15
<212> TYPE: PRT
<213> ORGANISM: Artificial sequence
<220> FEATURE:
<223> OTHER INFORMATION: Antibody CDR fragment

<400> SEQUENCE: 9

Glu Arg Gly Tyr Thr Ser Ser Phe Arg Arg Asp Ala Phe Asp Lys
1               5                   10                  15

<210> SEQ ID NO 10
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 10

Gly Tyr Thr Phe Asn Ala Tyr
1               5

<210> SEQ ID NO 11
<211> LENGTH: 6
<212> TYPE: PRT
<213> ORGANISM: Artificial sequence
<220> FEATURE:
<223> OTHER INFORMATION: Antibody CDR fragment

<400> SEQUENCE: 11

Asn Pro Asn Ser Gly Gly
1               5

<210> SEQ ID NO 12
<211> LENGTH: 15
<212> TYPE: PRT
<213> ORGANISM: Artificial sequence
<220> FEATURE:
<223> OTHER INFORMATION: Antibody CDR fragment

<400> SEQUENCE: 12

Glu Arg Gly Tyr Thr Ser Ser Phe Arg Arg Asp Ala Phe Asp Lys
1               5                   10                  15

<210> SEQ ID NO 13
<211> LENGTH: 7
<212> TYPE: PRT
<213> ORGANISM: Artificial sequence
<220> FEATURE:
<223> OTHER INFORMATION: Artificial sequence

<400> SEQUENCE: 13

Gly Tyr Thr Phe Asn Ala Tyr
1               5

<210> SEQ ID NO 14
<211> LENGTH: 6
<212> TYPE: PRT
```

-continued

```
<213> ORGANISM: Artificial sequence
<220> FEATURE:
<223> OTHER INFORMATION: Antibody CDR fragment

<400> SEQUENCE: 14

Asn Pro Asn Ser Gly Gly
1               5

<210> SEQ ID NO 15
<211> LENGTH: 15
<212> TYPE: PRT
<213> ORGANISM: Artificial sequence
<220> FEATURE:
<223> OTHER INFORMATION: Antibody CDR fragment

<400> SEQUENCE: 15

Glu Arg Gly Tyr Thr Ser Ser Phe Arg Arg Asp Ala Phe Asp Lys
1               5                   10                  15

<210> SEQ ID NO 16
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 16

Gly Tyr Thr Phe Asn Ala Tyr
1               5

<210> SEQ ID NO 17
<211> LENGTH: 6
<212> TYPE: PRT
<213> ORGANISM: Artificial sequence
<220> FEATURE:
<223> OTHER INFORMATION: Antibody CDR fragment

<400> SEQUENCE: 17

Asn Pro Asn Ser Gly Gly
1               5

<210> SEQ ID NO 18
<211> LENGTH: 15
<212> TYPE: PRT
<213> ORGANISM: Artificial sequence
<220> FEATURE:
<223> OTHER INFORMATION: Antibody CDR fragment

<400> SEQUENCE: 18

Glu Arg Gly Tyr Thr Ser Ser Phe Arg Arg Asp Ala Phe Asp Lys
1               5                   10                  15

<210> SEQ ID NO 19
<211> LENGTH: 14
<212> TYPE: PRT
<213> ORGANISM: Artificial sequence
<220> FEATURE:
<223> OTHER INFORMATION: Antibody CDR fragment

<400> SEQUENCE: 19

Thr Gly Thr Ser Ser Asp Val Gly Gly Tyr Asn Tyr Val Ser
1               5                   10

<210> SEQ ID NO 20
<211> LENGTH: 7
<212> TYPE: PRT
<213> ORGANISM: Artificial sequence
```

```
<220> FEATURE:
<223> OTHER INFORMATION: Antibody CDR fragment

<400> SEQUENCE: 20

Asp Val Ser Asn Arg Pro Ser
1               5

<210> SEQ ID NO 21
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 21

Ser Ser Tyr Thr Ser Ser Ser Thr Leu Val
1               5                   10

<210> SEQ ID NO 22
<211> LENGTH: 14
<212> TYPE: PRT
<213> ORGANISM: Artificial sequence
<220> FEATURE:
<223> OTHER INFORMATION: Antibody CDR fragment

<400> SEQUENCE: 22

Ala Ser Ser Thr Gly Ala Val Thr Ser Gly Tyr Tyr Pro Asn
1               5                   10

<210> SEQ ID NO 23
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 23

Ser Thr Ser Asn Lys His Ser
1               5

<210> SEQ ID NO 24
<211> LENGTH: 9
<212> TYPE: PRT
<213> ORGANISM: Artificial sequence
<220> FEATURE:
<223> OTHER INFORMATION: Antibody CDR fragment

<400> SEQUENCE: 24

Leu Leu Tyr Tyr Gly Gly Ala Trp Val
1               5

<210> SEQ ID NO 25
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 25

Ser Gly Ser Ser Ser Asp Ile Gly Asn His Tyr Val Ser
1               5                   10

<210> SEQ ID NO 26
<211> LENGTH: 7
<212> TYPE: PRT
<213> ORGANISM: Artificial sequence
<220> FEATURE:
```

-continued

<223> OTHER INFORMATION: Antibody CDR fragment

<400> SEQUENCE: 26

```
Glu Asp Asn Lys Arg Pro Ser
1               5
```

<210> SEQ ID NO 27
<211> LENGTH: 11
<212> TYPE: PRT
<213> ORGANISM: Artificial sequence
<220> FEATURE:
<223> OTHER INFORMATION: Antibody CDR fragment

<400> SEQUENCE: 27

```
Gly Thr Trp Asp Asn Ser Leu Arg Ser Gly Phe
1               5                   10
```

<210> SEQ ID NO 28
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 28

```
Ser Gly Ser Ser Ser Asn Ile Gly Asn Asn Tyr Val Ser
1               5                   10
```

<210> SEQ ID NO 29
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 29

```
Glu Asn Asn Lys Arg Pro Ser
1               5
```

<210> SEQ ID NO 30
<211> LENGTH: 11
<212> TYPE: PRT
<213> ORGANISM: Artificial sequence
<220> FEATURE:
<223> OTHER INFORMATION: Antibody CDR fragment

<400> SEQUENCE: 30

```
Gly Thr Trp Asp Ser Ser Leu Ser Ala Val Val
1               5                   10
```

<210> SEQ ID NO 31
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 31

```
Ser Gly Ser Thr Ser Asn Ile Gly Ser Asn Ser Val Ser
1               5                   10
```

<210> SEQ ID NO 32
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 32

Asp Asn Ala Lys Arg Pro Ser
1               5

<210> SEQ ID NO 33
<211> LENGTH: 11
<212> TYPE: PRT
<213> ORGANISM: Artificial sequence
<220> FEATURE:
<223> OTHER INFORMATION: Antibody CDR fragment

<400> SEQUENCE: 33

Gly Thr Trp Asp Ser Gly Leu Ser Val Met Val
1               5                   10

<210> SEQ ID NO 34
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 34

Ser Gly Ser Ser Ser Asn Ile Gly Ser Asn Phe Val Tyr
1               5                   10

<210> SEQ ID NO 35
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 35

Arg Asn Asn Gln Arg Pro Ser
1               5

<210> SEQ ID NO 36
<211> LENGTH: 11
<212> TYPE: PRT
<213> ORGANISM: Artificial sequence
<220> FEATURE:
<223> OTHER INFORMATION: Antibody CDR fragment

<400> SEQUENCE: 36

Ala Thr Trp Asp Asp Ser Leu Ser Gly Tyr Val
1               5                   10

<210> SEQ ID NO 37
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 37

Gly Tyr Thr Phe Ser His Tyr Trp Ile Gly
1               5                   10

<210> SEQ ID NO 38
<211> LENGTH: 10
<212> TYPE: PRT
<213> ORGANISM: Artificial sequence
<220> FEATURE:
<223> OTHER INFORMATION: Antibody CDR fragment

```
<400> SEQUENCE: 38

Ile Ile Tyr Pro Asp Asp Ser Asp Ser Arg
1               5                   10

<210> SEQ ID NO 39
<211> LENGTH: 15
<212> TYPE: PRT
<213> ORGANISM: Artificial sequence
<220> FEATURE:
<223> OTHER INFORMATION: Antibody CDR fragment

<400> SEQUENCE: 39

His Trp Leu Lys Arg Gly Ser Asn Phe Gly Phe Gly Phe Asp Pro
1               5                   10                  15

<210> SEQ ID NO 40
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 40

Gly Tyr Asn Phe Asn His Gln Gly Ile Ser
1               5                   10

<210> SEQ ID NO 41
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 41

Trp Ile Ser Gly Phe Asn Gly Lys Thr Asn
1               5                   10

<210> SEQ ID NO 42
<211> LENGTH: 12
<212> TYPE: PRT
<213> ORGANISM: Artificial sequence
<220> FEATURE:
<223> OTHER INFORMATION: Antibody CDR fragment

<400> SEQUENCE: 42

Gly Gly Glu Gln Trp Leu Val Gln Asn Phe Val His
1               5                   10

<210> SEQ ID NO 43
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 43

Gly Tyr Thr Phe Asn Ala Tyr Tyr Ile His
1               5                   10

<210> SEQ ID NO 44
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 44
```

```
Trp Ile Asn Pro Asn Ser Gly Gly Thr Asn
1               5                   10

<210> SEQ ID NO 45
<211> LENGTH: 15
<212> TYPE: PRT
<213> ORGANISM: Artificial sequence
<220> FEATURE:
<223> OTHER INFORMATION: Antibody CDR region

<400> SEQUENCE: 45

Glu Arg Gly Tyr Thr Ser Ser Phe Arg Arg Asp Ala Phe Asp Lys
1               5                   10                  15

<210> SEQ ID NO 46
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 46

Gly Tyr Thr Phe Asn Ala Tyr Tyr Ile His
1               5                   10

<210> SEQ ID NO 47
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 47

Trp Ile Asn Pro Asn Ser Gly Gly Thr Asn
1               5                   10

<210> SEQ ID NO 48
<211> LENGTH: 15
<212> TYPE: PRT
<213> ORGANISM: Artificial sequence
<220> FEATURE:
<223> OTHER INFORMATION: Antibody CDR fragment

<400> SEQUENCE: 48

Glu Arg Gly Tyr Thr Ser Ser Phe Arg Arg Asp Ala Phe Asp Lys
1               5                   10                  15

<210> SEQ ID NO 49
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 49

Gly Tyr Thr Phe Asn Ala Tyr Tyr Ile His
1               5                   10

<210> SEQ ID NO 50
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 50
```

Trp Ile Asn Pro Asn Ser Gly Gly Thr Asn
1               5                   10

<210> SEQ ID NO 51
<211> LENGTH: 15
<212> TYPE: PRT
<213> ORGANISM: Artificial sequence
<220> FEATURE:
<223> OTHER INFORMATION: Antibody CDR fragment

<400> SEQUENCE: 51

Glu Arg Gly Tyr Thr Ser Ser Phe Arg Arg Asp Ala Phe Asp Lys
1               5                   10                  15

<210> SEQ ID NO 52
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 52

Gly Tyr Thr Phe Asn Ala Tyr Tyr Ile His
1               5                   10

<210> SEQ ID NO 53
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 53

Trp Ile Asn Pro Asn Ser Gly Gly Thr Asn
1               5                   10

<210> SEQ ID NO 54
<211> LENGTH: 15
<212> TYPE: PRT
<213> ORGANISM: Artificial sequence
<220> FEATURE:
<223> OTHER INFORMATION: Antibody CDR fragment

<400> SEQUENCE: 54

Glu Arg Gly Tyr Thr Ser Ser Phe Arg Arg Asp Ala Phe Asp Lys
1               5                   10                  15

<210> SEQ ID NO 55
<211> LENGTH: 14
<212> TYPE: PRT
<213> ORGANISM: Artificial sequence
<220> FEATURE:
<223> OTHER INFORMATION: Antibody CDR fragment

<400> SEQUENCE: 55

Thr Gly Thr Ser Ser Asp Val Gly Gly Tyr Asn Tyr Val Ser
1               5                   10

<210> SEQ ID NO 56
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 56

Asp Val Ser Asn Arg Pro Ser

```
1               5

<210> SEQ ID NO 57
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 57

Ser Ser Tyr Thr Ser Ser Ser Thr Leu Val
1               5                   10

<210> SEQ ID NO 58
<211> LENGTH: 14
<212> TYPE: PRT
<213> ORGANISM: Artificial sequence
<220> FEATURE:
<223> OTHER INFORMATION: Antibody CDR fragment

<400> SEQUENCE: 58

Ala Ser Ser Thr Gly Ala Val Thr Ser Gly Tyr Tyr Pro Asn
1               5                   10

<210> SEQ ID NO 59
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 59

Ser Thr Ser Asn Lys His Ser
1               5

<210> SEQ ID NO 60
<211> LENGTH: 9
<212> TYPE: PRT
<213> ORGANISM: Artificial sequence
<220> FEATURE:
<223> OTHER INFORMATION: Antibody CDR fragment

<400> SEQUENCE: 60

Leu Leu Tyr Tyr Gly Gly Ala Trp Val
1               5

<210> SEQ ID NO 61
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 61

Ser Gly Ser Ser Ser Asp Ile Gly Asn His Tyr Val Ser
1               5                   10

<210> SEQ ID NO 62
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 62

Glu Asp Asn Lys Arg Pro Ser
1               5
```

-continued

```
<210> SEQ ID NO 63
<211> LENGTH: 11
<212> TYPE: PRT
<213> ORGANISM: Artificial sequence
<220> FEATURE:
<223> OTHER INFORMATION: Antibody CDR fragment

<400> SEQUENCE: 63

Gly Thr Trp Asp Asn Ser Leu Arg Ser Gly Phe
1               5                   10

<210> SEQ ID NO 64
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 64

Ser Gly Ser Ser Ser Asn Ile Gly Asn Asn Tyr Val Ser
1               5                   10

<210> SEQ ID NO 65
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 65

Glu Asn Asn Lys Arg Pro Ser
1               5

<210> SEQ ID NO 66
<211> LENGTH: 11
<212> TYPE: PRT
<213> ORGANISM: Artificial sequence
<220> FEATURE:
<223> OTHER INFORMATION: Antibody CDR fragment

<400> SEQUENCE: 66

Gly Thr Trp Asp Ser Ser Leu Ser Ala Val Val
1               5                   10

<210> SEQ ID NO 67
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 67

Ser Gly Ser Thr Ser Asn Ile Gly Ser Asn Ser Val Ser
1               5                   10

<210> SEQ ID NO 68
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 68

Asp Asn Ala Lys Arg Pro Ser
1               5
```

-continued

```
<210> SEQ ID NO 69
<211> LENGTH: 11
<212> TYPE: PRT
<213> ORGANISM: Artificial sequence
<220> FEATURE:
<223> OTHER INFORMATION: Antibody CDR fragment

<400> SEQUENCE: 69

Gly Thr Trp Asp Ser Gly Leu Ser Val Met Val
1               5                   10

<210> SEQ ID NO 70
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 70

Ser Gly Ser Ser Ser Asn Ile Gly Ser Asn Phe Val Tyr
1               5                   10

<210> SEQ ID NO 71
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 71

Arg Asn Asn Gln Arg Pro Ser
1               5

<210> SEQ ID NO 72
<211> LENGTH: 11
<212> TYPE: PRT
<213> ORGANISM: Artificial sequence
<220> FEATURE:
<223> OTHER INFORMATION: Antibody CDR fragment

<400> SEQUENCE: 72

Ala Thr Trp Asp Asp Ser Leu Ser Gly Tyr Val
1               5                   10

<210> SEQ ID NO 73
<211> LENGTH: 5
<212> TYPE: PRT
<213> ORGANISM: Artificial sequence
<220> FEATURE:
<223> OTHER INFORMATION: Antibody CDR fragment

<400> SEQUENCE: 73

His Tyr Trp Ile Gly
1               5

<210> SEQ ID NO 74
<211> LENGTH: 17
<212> TYPE: PRT
<213> ORGANISM: Artificial sequence
<220> FEATURE:
<223> OTHER INFORMATION: Antibody CDR fragment

<400> SEQUENCE: 74

Ile Ile Tyr Pro Asp Asp Ser Asp Ser Arg Tyr Ser Pro Ser Phe Gln
1               5                   10                  15

Gly
```

```
<210> SEQ ID NO 75
<211> LENGTH: 15
<212> TYPE: PRT
<213> ORGANISM: Artificial sequence
<220> FEATURE:
<223> OTHER INFORMATION: Antibody CDR fragment

<400> SEQUENCE: 75

His Trp Leu Lys Arg Gly Ser Asn Phe Gly Phe Gly Phe Asp Pro
1               5                   10                  15

<210> SEQ ID NO 76
<211> LENGTH: 5
<212> TYPE: PRT
<213> ORGANISM: Artificial sequence
<220> FEATURE:
<223> OTHER INFORMATION: Antibody CDR fragment

<400> SEQUENCE: 76

His Gln Gly Ile Ser
1               5

<210> SEQ ID NO 77
<211> LENGTH: 17
<212> TYPE: PRT
<213> ORGANISM: Artificial sequence
<220> FEATURE:
<223> OTHER INFORMATION: Antibody CDR fragment

<400> SEQUENCE: 77

Trp Ile Ser Gly Phe Asn Gly Lys Thr Asn Tyr Ala Gln Lys Phe Gln
1               5                   10                  15

Gly

<210> SEQ ID NO 78
<211> LENGTH: 12
<212> TYPE: PRT
<213> ORGANISM: Artificial sequence
<220> FEATURE:
<223> OTHER INFORMATION: Antibody CDR fragment

<400> SEQUENCE: 78

Gly Gly Glu Gln Trp Leu Val Gln Asn Phe Val His
1               5                   10

<210> SEQ ID NO 79
<211> LENGTH: 5
<212> TYPE: PRT
<213> ORGANISM: Artificial sequence
<220> FEATURE:
<223> OTHER INFORMATION: Antibody CDR fragment

<400> SEQUENCE: 79

Ala Tyr Tyr Ile His
1               5

<210> SEQ ID NO 80
<211> LENGTH: 17
<212> TYPE: PRT
<213> ORGANISM: Artificial sequence
<220> FEATURE:
<223> OTHER INFORMATION: Antibody CDR fragment

<400> SEQUENCE: 80

Trp Ile Asn Pro Asn Ser Gly Gly Thr Asn Tyr Ala Gln Asn Phe Lys
```

-continued

```
1               5               10              15

Gly

<210> SEQ ID NO 81
<211> LENGTH: 15
<212> TYPE: PRT
<213> ORGANISM: Artificial sequence
<220> FEATURE:
<223> OTHER INFORMATION: Antibody CDR fragment

<400> SEQUENCE: 81

Glu Arg Gly Tyr Thr Ser Ser Phe Arg Arg Asp Ala Phe Asp Lys
1               5               10              15

<210> SEQ ID NO 82
<211> LENGTH: 5
<212> TYPE: PRT
<213> ORGANISM: Artificial sequence
<220> FEATURE:
<223> OTHER INFORMATION: Antibody CDR fragment

<400> SEQUENCE: 82

Ala Tyr Tyr Ile His
1               5

<210> SEQ ID NO 83
<211> LENGTH: 17
<212> TYPE: PRT
<213> ORGANISM: Artificial sequence
<220> FEATURE:
<223> OTHER INFORMATION: Antibody CDR fragment

<400> SEQUENCE: 83

Trp Ile Asn Pro Asn Ser Gly Gly Thr Asn Tyr Ala Gln Asn Phe Lys
1               5               10              15

Gly

<210> SEQ ID NO 84
<211> LENGTH: 15
<212> TYPE: PRT
<213> ORGANISM: Artificial sequence
<220> FEATURE:
<223> OTHER INFORMATION: Antibody CDR fragment

<400> SEQUENCE: 84

Glu Arg Gly Tyr Thr Ser Ser Phe Arg Arg Asp Ala Phe Asp Lys
1               5               10              15

<210> SEQ ID NO 85
<211> LENGTH: 5
<212> TYPE: PRT
<213> ORGANISM: Artificial sequence
<220> FEATURE:
<223> OTHER INFORMATION: Antibody CDR fragment

<400> SEQUENCE: 85

Ala Tyr Tyr Ile His
1               5

<210> SEQ ID NO 86
<211> LENGTH: 17
<212> TYPE: PRT
<213> ORGANISM: Artificial sequence
<220> FEATURE:
<223> OTHER INFORMATION: Antibody CDR fragment
```

-continued

```
<400> SEQUENCE: 86

Trp Ile Asn Pro Asn Ser Gly Gly Thr Asn Tyr Ala Gln Asn Phe Lys
1               5                   10                  15

Gly

<210> SEQ ID NO 87
<211> LENGTH: 15
<212> TYPE: PRT
<213> ORGANISM: Artificial sequence
<220> FEATURE:
<223> OTHER INFORMATION: Antibody CDR fragment

<400> SEQUENCE: 87

Glu Arg Gly Tyr Thr Ser Ser Phe Arg Arg Asp Ala Phe Asp Lys
1               5                   10                  15

<210> SEQ ID NO 88
<211> LENGTH: 5
<212> TYPE: PRT
<213> ORGANISM: Artificial sequence
<220> FEATURE:
<223> OTHER INFORMATION: Antibody CDR fragment

<400> SEQUENCE: 88

Ala Tyr Tyr Ile His
1               5

<210> SEQ ID NO 89
<211> LENGTH: 17
<212> TYPE: PRT
<213> ORGANISM: Artificial sequence
<220> FEATURE:
<223> OTHER INFORMATION: Antibody CDR fragment

<400> SEQUENCE: 89

Trp Ile Asn Pro Asn Ser Gly Gly Thr Asn Tyr Ala Gln Asn Phe Lys
1               5                   10                  15

Gly

<210> SEQ ID NO 90
<211> LENGTH: 15
<212> TYPE: PRT
<213> ORGANISM: Artificial sequence
<220> FEATURE:
<223> OTHER INFORMATION: Antibody CDR fragment

<400> SEQUENCE: 90

Glu Arg Gly Tyr Thr Ser Ser Phe Arg Arg Asp Ala Phe Asp Lys
1               5                   10                  15

<210> SEQ ID NO 91
<211> LENGTH: 14
<212> TYPE: PRT
<213> ORGANISM: Artificial sequence
<220> FEATURE:
<223> OTHER INFORMATION: Antibody CDR fragment

<400> SEQUENCE: 91

Thr Gly Thr Ser Ser Asp Val Gly Gly Tyr Asn Tyr Val Ser
1               5                   10

<210> SEQ ID NO 92
<211> LENGTH: 7
<212> TYPE: PRT
<213> ORGANISM: Artificial sequence
```

```
<220> FEATURE:
<223> OTHER INFORMATION: Antibody CDR fragment

<400> SEQUENCE: 92

Asp Val Ser Asn Arg Pro Ser
1               5

<210> SEQ ID NO 93
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 93

Ser Ser Tyr Thr Ser Ser Ser Thr Leu Val
1               5               10

<210> SEQ ID NO 94
<211> LENGTH: 14
<212> TYPE: PRT
<213> ORGANISM: Artificial sequence
<220> FEATURE:
<223> OTHER INFORMATION: Antibody CDR fragment

<400> SEQUENCE: 94

Ala Ser Ser Thr Gly Ala Val Thr Ser Gly Tyr Tyr Pro Asn
1               5               10

<210> SEQ ID NO 95
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 95

Ser Thr Ser Asn Lys His Ser
1               5

<210> SEQ ID NO 96
<211> LENGTH: 9
<212> TYPE: PRT
<213> ORGANISM: Artificial sequence
<220> FEATURE:
<223> OTHER INFORMATION: Antibody CDR fragment

<400> SEQUENCE: 96

Leu Leu Tyr Tyr Gly Gly Ala Trp Val
1               5

<210> SEQ ID NO 97
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 97

Ser Gly Ser Ser Ser Asp Ile Gly Asn His Tyr Val Ser
1               5               10

<210> SEQ ID NO 98
<211> LENGTH: 7
<212> TYPE: PRT
<213> ORGANISM: Artificial sequence
<220> FEATURE:
```

```
<223> OTHER INFORMATION: Antibody CDR fragment

<400> SEQUENCE: 98

Glu Asp Asn Lys Arg Pro Ser
1               5

<210> SEQ ID NO 99
<211> LENGTH: 11
<212> TYPE: PRT
<213> ORGANISM: Artificial sequence
<220> FEATURE:
<223> OTHER INFORMATION: Antibody CDR fragment

<400> SEQUENCE: 99

Gly Thr Trp Asp Asn Ser Leu Arg Ser Gly Phe
1               5                   10

<210> SEQ ID NO 100
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 100

Ser Gly Ser Ser Ser Asn Ile Gly Asn Asn Tyr Val Ser
1               5                   10

<210> SEQ ID NO 101
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 101

Glu Asn Asn Lys Arg Pro Ser
1               5

<210> SEQ ID NO 102
<211> LENGTH: 11
<212> TYPE: PRT
<213> ORGANISM: Artificial sequence
<220> FEATURE:
<223> OTHER INFORMATION: Antibody CDR fragment

<400> SEQUENCE: 102

Gly Thr Trp Asp Ser Ser Leu Ser Ala Val Val
1               5                   10

<210> SEQ ID NO 103
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 103

Ser Gly Ser Thr Ser Asn Ile Gly Ser Asn Ser Val Ser
1               5                   10

<210> SEQ ID NO 104
<211> LENGTH: 7
<212> TYPE: PRT
<213> ORGANISM: Artificial sequence
<220> FEATURE:
<223> OTHER INFORMATION: Antibody CDR fragment
```

<400> SEQUENCE: 104

Asp Asn Ala Lys Arg Pro Ser
1               5

<210> SEQ ID NO 105
<211> LENGTH: 11
<212> TYPE: PRT
<213> ORGANISM: Artificial sequence
<220> FEATURE:
<223> OTHER INFORMATION: Antibody CDR fragment

<400> SEQUENCE: 105

Gly Thr Trp Asp Ser Gly Leu Ser Val Met Val
1               5                   10

<210> SEQ ID NO 106
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 106

Ser Gly Ser Ser Ser Asn Ile Gly Ser Asn Phe Val Tyr
1               5                   10

<210> SEQ ID NO 107
<211> LENGTH: 7
<212> TYPE: PRT
<213> ORGANISM: Artificial sequence
<220> FEATURE:
<223> OTHER INFORMATION: Antibody CDR fragment

<400> SEQUENCE: 107

Arg Asn Asn Gln Arg Pro Ser
1               5

<210> SEQ ID NO 108
<211> LENGTH: 11
<212> TYPE: PRT
<213> ORGANISM: Artificial sequence
<220> FEATURE:
<223> OTHER INFORMATION: Antibody CDR fragment

<400> SEQUENCE: 108

Ala Thr Trp Asp Asp Ser Leu Ser Gly Tyr Val
1               5                   10

<210> SEQ ID NO 109
<211> LENGTH: 6
<212> TYPE: PRT
<213> ORGANISM: Artificial sequence
<220> FEATURE:
<223> OTHER INFORMATION: Antibody CDR fragment

<400> SEQUENCE: 109

Ser His Tyr Trp Ile Gly
1               5

<210> SEQ ID NO 110
<211> LENGTH: 13
<212> TYPE: PRT
<213> ORGANISM: Artificial sequence
<220> FEATURE:
<223> OTHER INFORMATION: Antibody CDR fragment

```
<400> SEQUENCE: 110

Trp Met Gly Ile Ile Tyr Pro Asp Asp Ser Asp Ser Arg
1               5                   10

<210> SEQ ID NO 111
<211> LENGTH: 16
<212> TYPE: PRT
<213> ORGANISM: Artificial sequence
<220> FEATURE:
<223> OTHER INFORMATION: Antibody CDR fragment

<400> SEQUENCE: 111

Val Arg His Trp Leu Lys Arg Gly Ser Asn Phe Gly Phe Gly Phe Asp
1               5                   10                  15

<210> SEQ ID NO 112
<211> LENGTH: 6
<212> TYPE: PRT
<213> ORGANISM: Artificial sequence
<220> FEATURE:
<223> OTHER INFORMATION: Antibody CDR fragment

<400> SEQUENCE: 112

Asn His Gln Gly Ile Ser
1               5

<210> SEQ ID NO 113
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 113

Trp Met Gly Trp Ile Ser Gly Phe Asn Gly Lys Thr Asn
1               5                   10

<210> SEQ ID NO 114
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 114

Ala Ser Gly Gly Glu Gln Trp Leu Val Gln Asn Phe Val
1               5                   10

<210> SEQ ID NO 115
<211> LENGTH: 6
<212> TYPE: PRT
<213> ORGANISM: Artificial sequence
<220> FEATURE:
<223> OTHER INFORMATION: Antibody CDR fragment

<400> SEQUENCE: 115

Asn Ala Tyr Tyr Ile His
1               5

<210> SEQ ID NO 116
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 116
```

```
Trp Met Gly Trp Ile Asn Pro Asn Ser Gly Gly Thr Asn
1               5                   10

<210> SEQ ID NO 117
<211> LENGTH: 16
<212> TYPE: PRT
<213> ORGANISM: Artificial sequence
<220> FEATURE:
<223> OTHER INFORMATION: Antibody CDR fragment

<400> SEQUENCE: 117

Ala Thr Glu Arg Gly Tyr Thr Ser Ser Phe Arg Arg Asp Ala Phe Asp
1               5                   10                  15

<210> SEQ ID NO 118
<211> LENGTH: 6
<212> TYPE: PRT
<213> ORGANISM: Artificial sequence
<220> FEATURE:
<223> OTHER INFORMATION: Antibody CDR fragment

<400> SEQUENCE: 118

Asn Ala Tyr Tyr Ile His
1               5

<210> SEQ ID NO 119
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 119

Trp Met Gly Trp Ile Asn Pro Asn Ser Gly Gly Thr Asn
1               5                   10

<210> SEQ ID NO 120
<211> LENGTH: 16
<212> TYPE: PRT
<213> ORGANISM: Artificial sequence
<220> FEATURE:
<223> OTHER INFORMATION: Antibody CDR fragment

<400> SEQUENCE: 120

Ala Thr Glu Arg Gly Tyr Thr Ser Ser Phe Arg Arg Asp Ala Phe Asp
1               5                   10                  15

<210> SEQ ID NO 121
<211> LENGTH: 6
<212> TYPE: PRT
<213> ORGANISM: Artificial sequence
<220> FEATURE:
<223> OTHER INFORMATION: Antibody CDR fragment

<400> SEQUENCE: 121

Asn Ala Tyr Tyr Ile His
1               5

<210> SEQ ID NO 122
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 122
```

-continued

```
Trp Met Gly Trp Ile Asn Pro Asn Ser Gly Gly Thr Asn
1               5                   10

<210> SEQ ID NO 123
<211> LENGTH: 16
<212> TYPE: PRT
<213> ORGANISM: Artificial sequence
<220> FEATURE:
<223> OTHER INFORMATION: Antibody CDR fragment

<400> SEQUENCE: 123

Ala Thr Glu Arg Gly Tyr Thr Ser Ser Phe Arg Arg Asp Ala Phe Asp
1               5                   10                  15

<210> SEQ ID NO 124
<211> LENGTH: 6
<212> TYPE: PRT
<213> ORGANISM: Artificial sequence
<220> FEATURE:
<223> OTHER INFORMATION: Antibody CDR fragment

<400> SEQUENCE: 124

Asn Ala Tyr Tyr Ile His
1               5

<210> SEQ ID NO 125
<211> LENGTH: 13
<212> TYPE: PRT
<213> ORGANISM: Artificial sequence
<220> FEATURE:
<223> OTHER INFORMATION: Antibody CDR fragment

<400> SEQUENCE: 125

Trp Met Gly Trp Ile Asn Pro Asn Ser Gly Gly Thr Asn
1               5                   10

<210> SEQ ID NO 126
<211> LENGTH: 16
<212> TYPE: PRT
<213> ORGANISM: Artificial sequence
<220> FEATURE:
<223> OTHER INFORMATION: Antibody CDR fragment

<400> SEQUENCE: 126

Ala Thr Glu Arg Gly Tyr Thr Ser Ser Phe Arg Arg Asp Ala Phe Asp
1               5                   10                  15

<210> SEQ ID NO 127
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 127

Val Gly Gly Tyr Asn Tyr Val Ser Trp Tyr
1               5                   10

<210> SEQ ID NO 128
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 128

Leu Met Ile Tyr Asp Val Ser Asn Arg Pro
```

```
1               5                    10
```

<210> SEQ ID NO 129
<211> LENGTH: 9
<212> TYPE: PRT
<213> ORGANISM: Artificial sequence
<220> FEATURE:
<223> OTHER INFORMATION: Antibody CDR fragment

<400> SEQUENCE: 129

```
Ser Ser Tyr Thr Ser Ser Ser Thr Leu
1               5
```

<210> SEQ ID NO 130
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 130

```
Val Thr Ser Gly Tyr Tyr Pro Asn Trp Phe
1               5                    10
```

<210> SEQ ID NO 131
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 131

```
Ala Leu Ile Tyr Ser Thr Ser Asn Lys His
1               5                    10
```

<210> SEQ ID NO 132
<211> LENGTH: 8
<212> TYPE: PRT
<213> ORGANISM: Artificial sequence
<220> FEATURE:
<223> OTHER INFORMATION: Antibody CDR fragment

<400> SEQUENCE: 132

```
Leu Leu Tyr Tyr Gly Gly Ala Trp
1               5
```

<210> SEQ ID NO 133
<211> LENGTH: 9
<212> TYPE: PRT
<213> ORGANISM: Artificial sequence
<220> FEATURE:
<223> OTHER INFORMATION: Antibody CDR fragment

<400> SEQUENCE: 133

```
Ile Gly Asn His Tyr Val Ser Trp Tyr
1               5
```

<210> SEQ ID NO 134
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 134

```
Leu Leu Ile Tyr Glu Asp Asn Lys Arg Pro
1               5                    10
```

-continued

```
<210> SEQ ID NO 135
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 135

Gly Thr Trp Asp Asn Ser Leu Arg Ser Gly
1               5                   10

<210> SEQ ID NO 136
<211> LENGTH: 9
<212> TYPE: PRT
<213> ORGANISM: Artificial sequence
<220> FEATURE:
<223> OTHER INFORMATION: Antibody CDR fragment

<400> SEQUENCE: 136

Ile Gly Asn Asn Tyr Val Ser Trp Tyr
1               5

<210> SEQ ID NO 137
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 137

Leu Leu Ile Tyr Glu Asn Asn Lys Arg Pro
1               5                   10

<210> SEQ ID NO 138
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 138

Gly Thr Trp Asp Ser Ser Leu Ser Ala Val
1               5                   10

<210> SEQ ID NO 139
<211> LENGTH: 9
<212> TYPE: PRT
<213> ORGANISM: Artificial sequence
<220> FEATURE:
<223> OTHER INFORMATION: Antibody CDR fragment

<400> SEQUENCE: 139

Ile Gly Ser Asn Ser Val Ser Trp Tyr
1               5

<210> SEQ ID NO 140
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 140

Leu Leu Leu Phe Asp Asn Ala Lys Arg Pro
1               5                   10
```

<210> SEQ ID NO 141
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 141

Gly Thr Trp Asp Ser Gly Leu Ser Val Met
1               5                   10

<210> SEQ ID NO 142
<211> LENGTH: 9
<212> TYPE: PRT
<213> ORGANISM: Artificial sequence
<220> FEATURE:
<223> OTHER INFORMATION: Antibody CDR fragment

<400> SEQUENCE: 142

Ile Gly Ser Asn Phe Val Tyr Trp Tyr
1               5

<210> SEQ ID NO 143
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 143

Leu Leu Ile Tyr Arg Asn Asn Gln Arg Pro
1               5                   10

<210> SEQ ID NO 144
<211> LENGTH: 10
<212> TYPE: PRT
<213> ORGANISM: Artificial sequence
<220> FEATURE:
<223> OTHER INFORMATION: Antibody CDR fragment

<400> SEQUENCE: 144

Ala Thr Trp Asp Asp Ser Leu Ser Gly Tyr
1               5                   10

<210> SEQ ID NO 145
<211> LENGTH: 473
<212> TYPE: PRT
<213> ORGANISM: Artificial sequence
<220> FEATURE:
<223> OTHER INFORMATION: Reformatted antibody

<400> SEQUENCE: 145

Met Gly Trp Ser Cys Ile Ile Leu Phe Leu Val Ala Thr Ala Thr Gly
1               5                   10                  15

Val His Ser Glu Val Gln Leu Val Glu Ser Ala Gly Glu Val Gln Lys
            20                  25                  30

Pro Gly Glu Ser Leu Arg Ile Ser Cys Lys Ala Ser Gly Tyr Thr Phe
        35                  40                  45

Ser His Tyr Trp Ile Gly Trp Val Arg Gln Leu Pro Gly Lys Gly Leu
    50                  55                  60

Glu Trp Met Gly Ile Ile Tyr Pro Asp Asp Ser Asp Ser Arg Tyr Ser
65                  70                  75                  80

Pro Ser Phe Gln Gly Gln Val Thr Met Ser Val Asp Lys Ser Ile Asn
                85                  90                  95

```
Thr Ala Tyr Leu Gln Trp Asn Ser Leu Lys Val Ser Asp Thr Ala Thr
            100                 105                 110

Tyr Tyr Cys Val Arg His Trp Leu Lys Arg Gly Ser Asn Phe Gly Phe
            115                 120                 125

Gly Phe Asp Pro Trp Gly Gln Gly Thr Thr Leu Thr Val Ser Ser Ala
            130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
            210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
                260                 265                 270

Pro Lys Asp Thr Leu Met Ile Ser Arg Thr Pro Glu Val Thr Cys Val
                275                 280                 285

Val Val Asp Val Ser His Glu Asp Pro Glu Val Lys Phe Asn Trp Tyr
            290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
                340                 345                 350

Ala Leu Pro Ala Pro Ile Glu Lys Thr Ile Ser Lys Ala Lys Gly Gln
                355                 360                 365

Pro Arg Glu Pro Gln Val Tyr Thr Leu Pro Pro Ser Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
                420                 425                 430

Tyr Ser Lys Leu Thr Val Asp Lys Ser Arg Trp Gln Gln Gly Asn Val
                435                 440                 445

Phe Ser Cys Ser Val Met His Glu Ala Leu His Asn His Tyr Thr Gln
            450                 455                 460

Lys Ser Leu Ser Leu Ser Pro Gly Lys
465                 470
```

```
<210> SEQ ID NO 146
<211> LENGTH: 470
<212> TYPE: PRT
<213> ORGANISM: Artificial sequence
<220> FEATURE:
```

-continued

<223> OTHER INFORMATION: Reformatted antibody

<400> SEQUENCE: 146

```
Met Gly Trp Ser Cys Ile Ile Leu Phe Leu Val Ala Thr Ala Thr Gly
1               5                   10                  15

Val His Ser Glu Met Gln Leu Val Gln Ser Gly Ala Glu Val Lys Lys
            20                  25                  30

Pro Gly Ala Ser Val Lys Val Ser Cys Lys Thr Ser Gly Tyr Asn Phe
            35                  40                  45

Asn His Gln Gly Ile Ser Trp Leu Arg Gln Ala Pro Gly Gln Gly Leu
        50                  55                  60

Glu Trp Met Gly Trp Ile Ser Gly Phe Asn Gly Lys Thr Asn Tyr Ala
65                  70                  75                  80

Gln Lys Phe Gln Gly Arg Val Thr Met Thr Ala Asp Arg Ser Thr Thr
                85                  90                  95

Thr Ala Tyr Met Glu Leu Arg Ser Leu Arg Ser Asp Asp Thr Ala Val
            100                 105                 110

Tyr Tyr Cys Ala Ser Gly Gly Glu Gln Trp Leu Val Gln Asn Phe Val
            115                 120                 125

His Trp Gly Gln Gly Thr Leu Leu Thr Val Ser Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
        210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400
```

-continued

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
        450                 455                 460

Ser Leu Ser Pro Gly Lys
465                 470

<210> SEQ ID NO 147
<211> LENGTH: 473
<212> TYPE: PRT
<213> ORGANISM: Artificial sequence
<220> FEATURE:
<223> OTHER INFORMATION: Antibody CDR fragment

<400> SEQUENCE: 147

Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Ala Ser Val Glu Val Ser Cys Lys Ala Ser Gly Tyr Thr Phe
        35                  40                  45

Asn Ala Tyr Tyr Ile His Trp Val Arg Gln Ala Pro Gly Gln Gly Leu
    50                  55                  60

Asp Trp Met Gly Trp Ile Asn Pro Asn Ser Gly Gly Thr Asn Tyr Ala
65                  70                  75                  80

Gln Asn Phe Lys Gly Arg Val Thr Met Thr Arg Asp Thr Ser Ile Ser
                85                  90                  95

Thr Ala Tyr Leu Glu Leu Arg Ser Leu Thr Ser Asp Asp Thr Ala Val
            100                 105                 110

Tyr Phe Cys Ala Thr Glu Arg Gly Tyr Thr Ser Ser Phe Arg Arg Asp
        115                 120                 125

Ala Phe Asp Lys Trp Gly Gln Gly Thr Leu Leu Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
            165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
        210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

-continued

```
Val Val Asp Val Ser His Glu Asp Pro Glu Val Lys Phe Asn Trp Tyr
290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470

<210> SEQ ID NO 148
<211> LENGTH: 473
<212> TYPE: PRT
<213> ORGANISM: Artificial sequence
<220> FEATURE:
<223> OTHER INFORMATION: Reformatted antibody

<400> SEQUENCE: 148

Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
                20                  25                  30

Pro Gly Ala Ser Val Glu Val Ser Cys Lys Ala Ser Gly Tyr Thr Phe
            35                  40                  45

Asn Ala Tyr Tyr Ile His Trp Val Arg Gln Ala Pro Gly Gln Gly Leu
    50                  55                  60

Asp Trp Met Gly Trp Ile Asn Pro Asn Ser Gly Gly Thr Asn Tyr Ala
65                  70                  75                  80

Gln Asn Phe Lys Gly Arg Val Thr Met Thr Arg Asp Thr Ser Ile Ser
                85                  90                  95

Thr Ala Tyr Leu Glu Leu Arg Ser Leu Thr Ser Asp Asp Thr Ala Val
            100                 105                 110

Tyr Phe Cys Ala Thr Glu Arg Gly Tyr Thr Ser Ser Phe Arg Arg Asp
            115                 120                 125

Ala Phe Asp Lys Trp Gly Gln Gly Thr Met Leu Thr Val Ser Ser Ala
    130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175
```

-continued

```
Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
            210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
            290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
            355                 360                 365

Pro Arg Glu Pro Gln Val Tyr Thr Leu Pro Pro Ser Arg Asp Glu Leu
            370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
                405                 410                 415

Tyr Lys Thr Thr Pro Pro Val Leu Asp Ser Asp Gly Ser Phe Phe Leu
            420                 425                 430

Tyr Ser Lys Leu Thr Val Asp Lys Ser Arg Trp Gln Gln Gly Asn Val
            435                 440                 445

Phe Ser Cys Ser Val Met His Glu Ala Leu His Asn His Tyr Thr Gln
    450                 455                 460

Lys Ser Leu Ser Leu Ser Pro Gly Lys
465                 470
```

<210> SEQ ID NO 149
<211> LENGTH: 473
<212> TYPE: PRT
<213> ORGANISM: Artificial sequence
<220> FEATURE:
<223> OTHER INFORMATION: Reformatted antibody

<400> SEQUENCE: 149

```
Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Ala Ser Val Glu Val Ser Cys Lys Ala Ser Gly Tyr Thr Phe
            35                  40                  45

Asn Ala Tyr Tyr Ile His Trp Val Arg Gln Ala Pro Gly Gln Gly Leu
    50                  55                  60
```

```
Asp Trp Met Gly Trp Ile Asn Pro Asn Ser Gly Gly Thr Asn Tyr Ala
65              70                  75                  80

Gln Asn Phe Lys Gly Arg Val Thr Met Thr Arg Asp Thr Ser Ile Ser
                85                  90                  95

Thr Ala Tyr Leu Glu Leu Arg Ser Leu Thr Ser Asp Asp Thr Ala Val
            100                 105                 110

Tyr Phe Cys Ala Thr Glu Arg Gly Tyr Thr Ser Ser Phe Arg Arg Asp
        115                 120                 125

Ala Phe Asp Lys Trp Gly Gln Gly Thr Met Leu Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
            165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
        195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
        275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
            325                 330                 335

Gln Asp Trp Leu Asn Gly Lys Glu Tyr Lys Cys Lys Val Ser Asn Lys
        340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
    370                 375                 380

Thr Lys Asn Gln Val Ser Leu Thr Cys Leu Val Lys Gly Phe Tyr Pro
385                 390                 395                 400

Ser Asp Ile Ala Val Glu Trp Glu Ser Asn Gly Gln Pro Glu Asn Asn
            405                 410                 415

Tyr Lys Thr Thr Pro Pro Val Leu Asp Ser Asp Gly Ser Phe Phe Leu
        420                 425                 430

Tyr Ser Lys Leu Thr Val Asp Lys Ser Arg Trp Gln Gln Gly Asn Val
        435                 440                 445

Phe Ser Cys Ser Val Met His Glu Ala Leu His Asn His Tyr Thr Gln
        450                 455                 460

Lys Ser Leu Ser Leu Ser Pro Gly Lys
465                 470
```

-continued

```
<210> SEQ ID NO 150
<211> LENGTH: 473
<212> TYPE: PRT
<213> ORGANISM: Artificial sequence
<220> FEATURE:
<223> OTHER INFORMATION: Reformatted antibody

<400> SEQUENCE: 150

Met Gly Trp Ser Cys Ile Ile Leu Phe Leu Val Ala Thr Ala Thr Gly
1               5                   10                  15

Val His Ser Glu Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Asn Ala Tyr Tyr Ile His Trp Val Arg Gln Ala Pro Gly Gln Gly Leu
    50                  55                  60

Asp Trp Met Gly Trp Ile Asn Pro Asn Ser Gly Gly Thr Asn Tyr Ala
65                  70                  75                  80

Gln Asn Phe Lys Gly Arg Val Thr Met Thr Arg Asp Thr Ser Ile Ser
                85                  90                  95

Thr Ala Tyr Leu Glu Leu Arg Ser Leu Thr Ser Asp Asp Thr Ala Val
            100                 105                 110

Tyr Phe Cys Ala Thr Glu Arg Gly Tyr Thr Ser Ser Phe Arg Arg Asp
            115                 120                 125

Ala Phe Asp Lys Trp Gly Gln Gly Thr Met Leu Thr Val Ser Ser Ala
        130                 135                 140

Ser Thr Lys Gly Pro Ser Val Phe Pro Leu Ala Pro Ser Ser Lys Ser
145                 150                 155                 160

Thr Ser Gly Gly Thr Ala Ala Leu Gly Cys Leu Val Lys Asp Tyr Phe
                165                 170                 175

Pro Glu Pro Val Thr Val Ser Trp Asn Ser Gly Ala Leu Thr Ser Gly
            180                 185                 190

Val His Thr Phe Pro Ala Val Leu Gln Ser Ser Gly Leu Tyr Ser Leu
            195                 200                 205

Ser Ser Val Val Thr Val Pro Ser Ser Ser Leu Gly Thr Gln Thr Tyr
    210                 215                 220

Ile Cys Asn Val Asn His Lys Pro Ser Asn Thr Lys Val Asp Lys Lys
225                 230                 235                 240

Val Glu Pro Lys Ser Cys Asp Lys Thr His Thr Cys Pro Pro Cys Pro
                245                 250                 255

Ala Pro Glu Leu Leu Gly Gly Pro Ser Val Phe Leu Phe Pro Pro Lys
            260                 265                 270

Pro Lys Asp Thr Leu Met Ile Ser Arg Thr Pro Glu Val Thr Cys Val
            275                 280                 285

Val Val Asp Val Ser His Glu Asp Pro Glu Val Lys Phe Asn Trp Tyr
    290                 295                 300

Val Asp Gly Val Glu Val His Asn Ala Lys Thr Lys Pro Arg Glu Glu
305                 310                 315                 320

Gln Tyr Asn Ser Thr Tyr Arg Val Val Ser Val Leu Thr Val Leu His
                325                 330                 335

Gln Asp Trp Leu Asn Gly Lys Glu Tyr Lys Cys Lys Val Ser Asn Lys
            340                 345                 350

Ala Leu Pro Ala Pro Ile Glu Lys Thr Ile Ser Lys Ala Lys Gly Gln
        355                 360                 365

Pro Arg Glu Pro Gln Val Tyr Thr Leu Pro Pro Ser Arg Asp Glu Leu
```

-continued

```
            370             375             380
Thr Lys Asn Gln Val Ser Leu Thr Cys Leu Val Lys Gly Phe Tyr Pro
385             390             395             400

Ser Asp Ile Ala Val Glu Trp Glu Ser Asn Gly Gln Pro Glu Asn Asn
                405             410             415

Tyr Lys Thr Thr Pro Pro Val Leu Asp Ser Asp Gly Ser Phe Phe Leu
                420             425             430

Tyr Ser Lys Leu Thr Val Asp Lys Ser Arg Trp Gln Gln Gly Asn Val
                435             440             445

Phe Ser Cys Ser Val Met His Glu Ala Leu His Asn His Tyr Thr Gln
        450             455             460

Lys Ser Leu Ser Leu Ser Pro Gly Lys
465             470

<210> SEQ ID NO 151
<211> LENGTH: 235
<212> TYPE: PRT
<213> ORGANISM: Artificial sequence
<220> FEATURE:
<223> OTHER INFORMATION: Reformatted antibody

<400> SEQUENCE: 151

Met Gly Trp Ser Cys Ile Ile Leu Phe Leu Val Ala Thr Ala Thr Gly
1               5               10              15

Val His Ser Glu Ser Ala Leu Thr Gln Pro Ala Ser Val Ser Gly Ser
                20              25              30

Pro Gly Gln Ser Ile Thr Ile Ser Cys Thr Gly Thr Ser Ser Asp Val
                35              40              45

Gly Gly Tyr Asn Tyr Val Ser Trp Tyr Gln Gln His Pro Gly Lys Ala
        50              55              60

Pro Lys Leu Met Ile Tyr Asp Val Ser Asn Arg Pro Ser Gly Val Ser
65              70              75              80

Asn Arg Phe Ser Gly Ser Lys Ser Gly Asn Thr Ala Ser Leu Thr Ile
                85              90              95

Ser Gly Leu Gln Ala Glu Asp Glu Ala Asp Tyr Tyr Cys Ser Ser Tyr
                100             105             110

Thr Ser Ser Ser Thr Leu Val Phe Gly Gly Gly Thr Lys Leu Thr Val
        115             120             125

Leu Gly Gln Pro Lys Ala Ala Pro Ser Val Thr Leu Phe Pro Pro Ser
        130             135             140

Ser Glu Glu Leu Gln Ala Asn Lys Ala Thr Leu Val Cys Leu Ile Ser
145             150             155             160

Asp Phe Tyr Pro Gly Ala Val Thr Val Ala Trp Lys Ala Asp Ser Ser
                165             170             175

Pro Val Lys Ala Gly Val Glu Thr Thr Thr Pro Ser Lys Gln Ser Asn
                180             185             190

Asn Lys Tyr Ala Ala Ser Ser Tyr Leu Ser Leu Thr Pro Glu Gln Trp
        195             200             205

Lys Ser His Arg Ser Tyr Ser Cys Gln Val Thr His Glu Gly Ser Thr
        210             215             220

Val Glu Lys Thr Val Ala Pro Thr Glu Cys Ser
225             230             235

<210> SEQ ID NO 152
<211> LENGTH: 234
<212> TYPE: PRT
```

<213> ORGANISM: Artificial sequence
<220> FEATURE:
<223> OTHER INFORMATION: Reformatted antibody

<400> SEQUENCE: 152

Met Gly Trp Ser Cys Ile Ile Leu Phe Leu Val Ala Thr Ala Thr Gly
1               5                   10                  15

Val His Ser Glu Thr Val Leu Thr Gln Glu Pro Ser Leu Thr Val Ser
                20                  25                  30

Pro Gly Gly Thr Val Thr Leu Thr Cys Ala Ser Ser Thr Gly Ala Val
            35                  40                  45

Thr Ser Gly Tyr Tyr Pro Asn Trp Phe Gln Gln Lys Pro Gly Gln Ala
    50                  55                  60

Pro Arg Ala Leu Ile Tyr Ser Thr Ser Asn Lys His Ser Trp Thr Pro
65                  70                  75                  80

Ala Arg Phe Ser Gly Ser Leu Leu Gly Gly Lys Ala Ala Leu Thr Leu
                85                  90                  95

Ser Gly Val Gln Pro Glu Asp Glu Ala Glu Tyr Tyr Cys Leu Leu Tyr
            100                 105                 110

Tyr Gly Gly Ala Trp Val Phe Gly Gly Gly Thr Lys Leu Thr Val Leu
            115                 120                 125

Gly Gln Pro Lys Ala Ala Pro Ser Val Thr Leu Phe Pro Pro Ser Ser
    130                 135                 140

Glu Glu Leu Gln Ala Asn Lys Ala Thr Leu Val Cys Leu Ile Ser Asp
145                 150                 155                 160

Phe Tyr Pro Gly Ala Val Thr Val Ala Trp Lys Ala Asp Ser Ser Pro
                165                 170                 175

Val Lys Ala Gly Val Glu Thr Thr Thr Pro Ser Lys Gln Ser Asn Asn
            180                 185                 190

Lys Tyr Ala Ala Ser Ser Tyr Leu Ser Leu Thr Pro Glu Gln Trp Lys
            195                 200                 205

Ser His Arg Ser Tyr Ser Cys Gln Val Thr His Glu Gly Ser Thr Val
    210                 215                 220

Glu Lys Thr Val Ala Pro Thr Glu Cys Ser
225                 230

<210> SEQ ID NO 153
<211> LENGTH: 235
<212> TYPE: PRT
<213> ORGANISM: Artificial sequence
<220> FEATURE:
<223> OTHER INFORMATION: Reformatted antibody

<400> SEQUENCE: 153

Met Gly Trp Ser Cys Ile Ile Leu Phe Leu Val Ala Thr Ala Thr Gly
1               5                   10                  15

Val His Ser Glu Ser Val Leu Thr Gln Pro Pro Ser Ile Ser Ala Ala
                20                  25                  30

Pro Gly Gln Arg Val Thr Ile Pro Cys Ser Gly Ser Ser Ser Asp Ile
            35                  40                  45

Gly Asn His Tyr Val Ser Trp Tyr Gln Gln Leu Pro Gly Ala Ala Pro
    50                  55                  60

Lys Leu Leu Ile Tyr Glu Asp Asn Lys Arg Pro Ser Gly Ile Pro Asp
65                  70                  75                  80

Arg Phe Ser Gly Ser Lys Ser Gly Thr Ser Ala Ser Leu Gly Ile Thr
                85                  90                  95

-continued

```
Gly Leu Gln Thr Gly Asp Glu Ala Asp Tyr Tyr Cys Gly Thr Trp Asp
        100                 105                 110

Asn Ser Leu Arg Ser Gly Phe Phe Gly Gly Gly Thr Lys Val Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 154
<211> LENGTH: 235
<212> TYPE: PRT
<213> ORGANISM: Artificial sequence
<220> FEATURE:
<223> OTHER INFORMATION: Reformatted antibody

<400> SEQUENCE: 154

Met Gly Trp Ser Cys Ile Ile Leu Phe Leu Val Ala Thr Ala Thr Gly
1               5                   10                  15

Val His Ser Glu Ser Val Leu Thr Gln Pro Pro Ser Val Ser Ala Ala
            20                  25                  30

Pro Gly Gln Lys Val Thr Ile Ser Cys Ser Gly Ser Ser Ser Asn Ile
        35                  40                  45

Gly Asn Asn Tyr Val Ser Trp Tyr Gln Gln Leu Pro Gly Thr Ala Pro
    50                  55                  60

Lys Leu Leu Ile Tyr Glu Asn Asn Lys Arg Pro Ser Gly Ile Pro Asp
65                  70                  75                  80

Arg Phe Ser Gly Ser Lys Ser Gly Thr Ser Ala Thr Leu Gly Ile Thr
                85                  90                  95

Gly Leu Gln Thr Gly Asp Glu Ala Gly Tyr Tyr Cys Gly Thr Trp Asp
        100                 105                 110

Ser Ser Leu Ser Ala Val Val Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220
```

-continued

```
Val Glu Lys Thr Val Ala Pro Thr Glu Cys Ser
225                 230                 235

<210> SEQ ID NO 155
<211> LENGTH: 235
<212> TYPE: PRT
<213> ORGANISM: Artificial sequence
<220> FEATURE:
<223> OTHER INFORMATION: Reformatted antibody

<400> SEQUENCE: 155

Met Gly Trp Ser Cys Ile Ile Leu Phe Leu Val Ala Thr Ala Thr Gly
1               5                   10                  15

Val His Ser Glu Ser Val Leu Thr Gln Pro Pro Ser Val Ser Ala Ala
                20                  25                  30

Pro Gly Gln Lys Val Thr Met Ser Cys Ser Gly Ser Thr Ser Asn Ile
            35                  40                  45

Gly Ser Asn Ser Val Ser Trp Tyr Gln His Leu Pro Gly Thr Ala Pro
        50                  55                  60

Lys Leu Leu Leu Phe Asp Asn Ala Lys Arg Pro Ser Gly Ile Pro Asp
65                  70                  75                  80

Arg Phe Ser Gly Ser Lys Ser Gly Thr Ser Ala Thr Leu Gly Ile Thr
                85                  90                  95

Gly Leu Gln Thr Gly Asp Glu Ala Asp Tyr Tyr Cys Gly Thr Trp Asp
            100                 105                 110

Ser Gly Leu Ser Val Met Val Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 156
<211> LENGTH: 235
<212> TYPE: PRT
<213> ORGANISM: Artificial sequence
<220> FEATURE:
<223> OTHER INFORMATION: Reformatted antibody

<400> SEQUENCE: 156

Met Gly Trp Ser Cys Ile Ile Leu Phe Leu Val Ala Thr Ala Thr Gly
1               5                   10                  15

Val His Ser Glu Ala Val Val Thr Gln Pro Pro Ser Ala Ser Gly Thr
                20                  25                  30

Pro Gly Gln Gly Val Thr Ile Ser Cys Ser Gly Ser Ser Ser Asn Ile
            35                  40                  45

Gly Ser Asn Phe Val Tyr Trp Tyr Gln Gln Leu Pro Gly Thr Ala Pro
        50                  55                  60
```

```
Lys Leu Leu Ile Tyr Arg Asn Asn Gln Arg Pro Ser Gly Val Pro Asp
65                  70                  75                  80

Arg Phe Ser Gly Ser Lys Ser Ala Thr Ser Ala Ser Leu Ala Ile Ser
                85                  90                  95

Gly Leu Arg Ser Glu Asp Glu Ala Asp Tyr Tyr Cys Ala Thr Trp Asp
            100                 105                 110

Asp Ser Leu Ser Gly Tyr Val Phe Gly Thr Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 157
<211> LENGTH: 14
<212> TYPE: PRT
<213> ORGANISM: Homo sapiens

<400> SEQUENCE: 157

Thr Val Ser Ser Ala Ser Thr Lys Gly Pro Ser Val Phe Pro
1               5                   10

<210> SEQ ID NO 158

<400> SEQUENCE: 158

000

<210> SEQ ID NO 159

<400> SEQUENCE: 159

000

<210> SEQ ID NO 160

<400> SEQUENCE: 160

000

<210> SEQ ID NO 161

<400> SEQUENCE: 161

000

<210> SEQ ID NO 162

<400> SEQUENCE: 162

000
```

-continued

```
<210> SEQ ID NO 163

<400> SEQUENCE: 163

000

<210> SEQ ID NO 164

<400> SEQUENCE: 164

000

<210> SEQ ID NO 165

<400> SEQUENCE: 165

000

<210> SEQ ID NO 166

<400> SEQUENCE: 166

000

<210> SEQ ID NO 167

<400> SEQUENCE: 167

000

<210> SEQ ID NO 168

<400> SEQUENCE: 168

000

<210> SEQ ID NO 169

<400> SEQUENCE: 169

000

<210> SEQ ID NO 170
<211> LENGTH: 25
<212> TYPE: PRT
<213> ORGANISM: Artificial Sequence
<220> FEATURE:
<223> OTHER INFORMATION: Synthetic sequence

<400> SEQUENCE: 170

Glu Val Gln Leu Val Glu Ser Ala Gly Glu Val Gln Lys Pro Gly Glu
1               5                   10                  15

Ser Leu Arg Ile Ser Cys Lys Ala Ser
            20                  25

<210> SEQ ID NO 171
<211> LENGTH: 19
<212> TYPE: PRT
<213> ORGANISM: Artificial Sequence
<220> FEATURE:
<223> OTHER INFORMATION: Synthetic sequence

<400> SEQUENCE: 171

Trp Ile Gly Trp Val Arg Gln Leu Pro Gly Lys Gly Leu Glu Trp Met
1               5                   10                  15
```

-continued

Gly Ile Ile

<210> SEQ ID NO 172
<211> LENGTH: 41
<212> TYPE: PRT
<213> ORGANISM: Artificial sequence
<220> FEATURE:
<223> OTHER INFORMATION: Synthetic construct

<400> SEQUENCE: 172

Ser Arg Tyr Ser Pro Ser Phe Gln Gly Gln Val Thr Met Ser Val Asp
1               5                   10                  15

Lys Ser Ile Asn Thr Ala Tyr Leu Gln Trp Asn Ser Leu Lys Val Ser
            20                  25                  30

Asp Thr Ala Thr Tyr Tyr Cys Val Arg
        35                  40

<210> SEQ ID NO 173
<211> LENGTH: 11
<212> TYPE: PRT
<213> ORGANISM: Artificial sequence
<220> FEATURE:
<223> OTHER INFORMATION: Synthetic construct

<400> SEQUENCE: 173

Trp Gly Gln Gly Thr Thr Leu Thr Val Ser Ser
1               5                   10

<210> SEQ ID NO 174
<211> LENGTH: 24
<212> TYPE: PRT
<213> ORGANISM: Artificial sequence
<220> FEATURE:
<223> OTHER INFORMATION: Synthetic construct

<400> SEQUENCE: 174

Met Gln Leu Val Gln Ser Gly Ala Glu Val Lys Lys Pro Gly Ala Ser
1               5                   10                  15

Val Lys Val Ser Cys Lys Thr Ser
            20

<210> SEQ ID NO 175
<211> LENGTH: 19
<212> TYPE: PRT
<213> ORGANISM: Artificial sequence
<220> FEATURE:
<223> OTHER INFORMATION: Synthetic construct

<400> SEQUENCE: 175

Gly Ile Ser Trp Leu Arg Gln Ala Pro Gly Gln Gly Leu Glu Trp Met
1               5                   10                  15

Gly Trp Ile

<210> SEQ ID NO 176
<211> LENGTH: 41
<212> TYPE: PRT
<213> ORGANISM: Artificial sequence
<220> FEATURE:
<223> OTHER INFORMATION: Synthetic construct

<400> SEQUENCE: 176

Thr Asn Tyr Ala Gln Lys Phe Gln Gly Arg Val Thr Met Thr Ala Asp
1               5                   10                  15

Arg Ser Thr Thr Thr Ala Tyr Met Glu Leu Arg Ser Leu Arg Ser Asp

-continued

```
                20              25              30

Asp Thr Ala Val Tyr Tyr Cys Ala Ser
       35              40

<210> SEQ ID NO 177
<211> LENGTH: 11
<212> TYPE: PRT
<213> ORGANISM: Artificial sequence
<220> FEATURE:
<223> OTHER INFORMATION: Synthetic construct

<400> SEQUENCE: 177

Trp Gly Gln Gly Thr Leu Leu Thr Val Ser Ser
1               5               10

<210> SEQ ID NO 178
<211> LENGTH: 25
<212> TYPE: PRT
<213> ORGANISM: Artificial sequence
<220> FEATURE:
<223> OTHER INFORMATION: Synthetic construct

<400> SEQUENCE: 178

Glu Val Gln Leu Val Gln Ser Gly Ala Glu Val Lys Lys Pro Gly Ala
1               5               10              15

Ser Val Glu Val Ser Cys Lys Ala Ser
            20              25

<210> SEQ ID NO 179
<211> LENGTH: 19
<212> TYPE: PRT
<213> ORGANISM: Artificial sequence
<220> FEATURE:
<223> OTHER INFORMATION: Synthetic construct

<400> SEQUENCE: 179

Tyr Ile His Trp Val Arg Gln Ala Pro Gly Gln Gly Leu Asp Trp Met
1               5               10              15

Gly Trp Ile

<210> SEQ ID NO 180
<211> LENGTH: 41
<212> TYPE: PRT
<213> ORGANISM: Artificial sequence
<220> FEATURE:
<223> OTHER INFORMATION: Synthetic construct

<400> SEQUENCE: 180

Thr Asn Tyr Ala Gln Asn Phe Lys Gly Arg Val Thr Met Thr Arg Asp
1               5               10              15

Thr Ser Ile Ser Thr Ala Tyr Leu Glu Leu Arg Ser Leu Thr Ser Asp
            20              25              30

Asp Thr Ala Val Tyr Phe Cys Ala Thr
       35              40

<210> SEQ ID NO 181
<211> LENGTH: 11
<212> TYPE: PRT
<213> ORGANISM: Artificial sequence
<220> FEATURE:
<223> OTHER INFORMATION: Synthetic construct

<400> SEQUENCE: 181

Trp Gly Gln Gly Thr Leu Leu Thr Val Ser Ser
```

1                    5                            10

<210> SEQ ID NO 182
<211> LENGTH: 25
<212> TYPE: PRT
<213> ORGANISM: Artificial sequence
<220> FEATURE:
<223> OTHER INFORMATION: Synthetic construct

<400> SEQUENCE: 182

Glu Val Gln Leu Val Gln Ser Gly Ala Glu Val Lys Lys Pro Gly Ala
1                    5                            10                            15

Ser Val Glu Val Ser Cys Lys Ala Ser
              20                            25

<210> SEQ ID NO 183
<211> LENGTH: 19
<212> TYPE: PRT
<213> ORGANISM: Artificial sequence
<220> FEATURE:
<223> OTHER INFORMATION: Synthetic construct

<400> SEQUENCE: 183

Tyr Ile His Trp Val Arg Gln Ala Pro Gly Gln Gly Leu Asp Trp Met
1                    5                            10                            15

Gly Trp Ile

<210> SEQ ID NO 184
<211> LENGTH: 41
<212> TYPE: PRT
<213> ORGANISM: Artificial sequence
<220> FEATURE:
<223> OTHER INFORMATION: Synthetic construct

<400> SEQUENCE: 184

Thr Asn Tyr Ala Gln Asn Phe Lys Gly Arg Val Thr Met Thr Arg Asp
1                    5                            10                            15

Thr Ser Ile Ser Thr Ala Tyr Leu Glu Leu Arg Ser Leu Thr Ser Asp
              20                            25                            30

Asp Thr Ala Val Tyr Phe Cys Ala Thr
        35                            40

<210> SEQ ID NO 185
<211> LENGTH: 11
<212> TYPE: PRT
<213> ORGANISM: Artificial sequence
<220> FEATURE:
<223> OTHER INFORMATION: Synthetic construct

<400> SEQUENCE: 185

Trp Gly Gln Gly Thr Met Leu Thr Val Ser Ser
1                    5                            10

<210> SEQ ID NO 186
<211> LENGTH: 25
<212> TYPE: PRT
<213> ORGANISM: Artificial sequence
<220> FEATURE:
<223> OTHER INFORMATION: Synthetic construct

<400> SEQUENCE: 186

Glu Val Gln Leu Val Gln Ser Gly Ala Glu Val Lys Lys Pro Gly Ala
1                    5                            10                            15

Ser Val Glu Val Ser Cys Lys Ala Ser

-continued

```
                    20                      25

<210> SEQ ID NO 187
<211> LENGTH: 19
<212> TYPE: PRT
<213> ORGANISM: Artificial sequence
<220> FEATURE:
<223> OTHER INFORMATION: Synthetic construct

<400> SEQUENCE: 187

Tyr Ile His Trp Val Arg Gln Ala Pro Gly Gln Gly Leu Asp Trp Met
1               5                   10                  15

Gly Trp Ile

<210> SEQ ID NO 188
<211> LENGTH: 41
<212> TYPE: PRT
<213> ORGANISM: Artificial sequence
<220> FEATURE:
<223> OTHER INFORMATION: Synthetic construct

<400> SEQUENCE: 188

Thr Asn Tyr Ala Gln Asn Phe Lys Gly Arg Val Thr Met Thr Arg Asp
1               5                   10                  15

Thr Ser Ile Ser Thr Ala Tyr Leu Glu Leu Arg Ser Leu Thr Ser Asp
                20                      25                  30

Asp Thr Ala Val Tyr Phe Cys Ala Thr
            35                  40

<210> SEQ ID NO 189
<211> LENGTH: 11
<212> TYPE: PRT
<213> ORGANISM: Artificial sequence
<220> FEATURE:
<223> OTHER INFORMATION: Synthetic construct

<400> SEQUENCE: 189

Trp Gly Gln Gly Thr Met Leu Thr Val Ser Ser
1               5                   10

<210> SEQ ID NO 190
<211> LENGTH: 25
<212> TYPE: PRT
<213> ORGANISM: Artificial Sequence
<220> FEATURE:
<223> OTHER INFORMATION: Synthetic construct

<400> SEQUENCE: 190

Glu Val Gln Leu Val Gln Ser Gly Ala Glu Val Lys Lys Pro Gly Ala
1               5                   10                  15

Ser Val Lys Val Ser Cys Lys Ala Ser
                20                      25

<210> SEQ ID NO 191
<211> LENGTH: 19
<212> TYPE: PRT
<213> ORGANISM: Artificial Sequence
<220> FEATURE:
<223> OTHER INFORMATION: Synthetic construct

<400> SEQUENCE: 191

Tyr Ile His Trp Val Arg Gln Ala Pro Gly Gln Gly Leu Asp Trp Met
1               5                   10                  15

Gly Trp Ile
```

-continued

```
<210> SEQ ID NO 192
<211> LENGTH: 41
<212> TYPE: PRT
<213> ORGANISM: Artificial Sequence
<220> FEATURE:
<223> OTHER INFORMATION: Synthetic construct

<400> SEQUENCE: 192

Thr Asn Tyr Ala Gln Asn Phe Lys Gly Arg Val Thr Met Thr Arg Asp
1               5                   10                  15

Thr Ser Ile Ser Thr Ala Tyr Leu Glu Leu Arg Ser Leu Thr Ser Asp
            20                  25                  30

Asp Thr Ala Val Tyr Phe Cys Ala Thr
        35                  40

<210> SEQ ID NO 193
<211> LENGTH: 11
<212> TYPE: PRT
<213> ORGANISM: Artificial sequence
<220> FEATURE:
<223> OTHER INFORMATION: Synthetic construct

<400> SEQUENCE: 193

Trp Gly Gln Gly Thr Met Leu Thr Val Ser Ser
1               5                   10

<210> SEQ ID NO 194
<211> LENGTH: 22
<212> TYPE: PRT
<213> ORGANISM: Artificial sequence
<220> FEATURE:
<223> OTHER INFORMATION: Synthetic construct

<400> SEQUENCE: 194

Glu Ser Ala Leu Thr Gln Pro Ala Ser Val Ser Gly Ser Pro Gly Gln
1               5                   10                  15

Ser Ile Thr Ile Ser Cys
            20

<210> SEQ ID NO 195
<211> LENGTH: 15
<212> TYPE: PRT
<213> ORGANISM: Artificial Sequence
<220> FEATURE:
<223> OTHER INFORMATION: Synthetic construct

<400> SEQUENCE: 195

Trp Tyr Gln Gln His Pro Gly Lys Ala Pro Lys Leu Met Ile Tyr
1               5                   10                  15

<210> SEQ ID NO 196
<211> LENGTH: 32
<212> TYPE: PRT
<213> ORGANISM: Artificial Sequence
<220> FEATURE:
<223> OTHER INFORMATION: Synthetic construct

<400> SEQUENCE: 196

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30
```

<210> SEQ ID NO 197
<211> LENGTH: 11
<212> TYPE: PRT
<213> ORGANISM: Artificial sequence
<220> FEATURE:
<223> OTHER INFORMATION: Synthetic construct

<400> SEQUENCE: 197

Phe Gly Gly Gly Thr Lys Leu Thr Val Leu Gly
1               5                   10

<210> SEQ ID NO 198
<211> LENGTH: 20
<212> TYPE: PRT
<213> ORGANISM: Artificial Sequence
<220> FEATURE:
<223> OTHER INFORMATION: Synthetic construct

<400> SEQUENCE: 198

Val Leu Thr Gln Glu Pro Ser Leu Thr Val Ser Pro Gly Gly Thr Val
1               5                   10                  15

Thr Leu Thr Cys
            20

<210> SEQ ID NO 199
<211> LENGTH: 15
<212> TYPE: PRT
<213> ORGANISM: Artificial Sequence
<220> FEATURE:
<223> OTHER INFORMATION: Synthetic construct

<400> SEQUENCE: 199

Trp Phe Gln Gln Lys Pro Gly Gln Ala Pro Arg Ala Leu Ile Tyr
1               5                   10                  15

<210> SEQ ID NO 200
<211> LENGTH: 32
<212> TYPE: PRT
<213> ORGANISM: Artificial Sequence
<220> FEATURE:
<223> OTHER INFORMATION: Synthetic construct

<400> SEQUENCE: 200

Trp Thr Pro Ala Arg Phe Ser Gly Ser Leu Leu Gly Gly Lys Ala Ala
1               5                   10                  15

Leu Thr Leu Ser Gly Val Gln Pro Glu Asp Glu Ala Glu Tyr Tyr Cys
            20                  25                  30

<210> SEQ ID NO 201
<211> LENGTH: 10
<212> TYPE: PRT
<213> ORGANISM: Artificial sequence
<220> FEATURE:
<223> OTHER INFORMATION: Synthetic construct

<400> SEQUENCE: 201

Phe Gly Gly Gly Thr Lys Leu Thr Val Leu
1               5                   10

<210> SEQ ID NO 202
<211> LENGTH: 22
<212> TYPE: PRT
<213> ORGANISM: Artificial sequence
<220> FEATURE:
<223> OTHER INFORMATION: Synthetic construct

<400> SEQUENCE: 202

-continued

```
Glu Ser Val Leu Thr Gln Pro Pro Ser Ile Ser Ala Ala Pro Gly Gln
1               5                   10                  15

Arg Val Thr Ile Pro Cys
            20

<210> SEQ ID NO 203
<211> LENGTH: 15
<212> TYPE: PRT
<213> ORGANISM: Artificial sequence
<220> FEATURE:
<223> OTHER INFORMATION: Synthetic construct

<400> SEQUENCE: 203

Trp Tyr Gln Gln Leu Pro Gly Ala Ala Pro Lys Leu Leu Ile Tyr
1               5                   10                  15

<210> SEQ ID NO 204
<211> LENGTH: 32
<212> TYPE: PRT
<213> ORGANISM: Artificial Sequence
<220> FEATURE:
<223> OTHER INFORMATION: Synthetic construct

<400> SEQUENCE: 204

Gly Ile Pro Asp Arg Phe Ser Gly Ser Lys Ser Gly Thr Ser Ala Ser
1               5                   10                  15

Leu Gly Ile Thr Gly Leu Gln Thr Gly Asp Glu Ala Asp Tyr Tyr Cys
            20                  25                  30

<210> SEQ ID NO 205
<211> LENGTH: 11
<212> TYPE: PRT
<213> ORGANISM: Artificial sequence
<220> FEATURE:
<223> OTHER INFORMATION: Synthetic construct

<400> SEQUENCE: 205

Phe Gly Gly Gly Thr Lys Val Thr Val Leu Gly
1               5                   10

<210> SEQ ID NO 206
<211> LENGTH: 22
<212> TYPE: PRT
<213> ORGANISM: Artificial sequence
<220> FEATURE:
<223> OTHER INFORMATION: Synthetic construct

<400> SEQUENCE: 206

Glu Ser Val Leu Thr Gln Pro Pro Ser Val Ser Ala Ala Pro Gly Gln
1               5                   10                  15

Lys Val Thr Ile Ser Cys
            20

<210> SEQ ID NO 207
<211> LENGTH: 15
<212> TYPE: PRT
<213> ORGANISM: Artificial sequence
<220> FEATURE:
<223> OTHER INFORMATION: Synthetic construct

<400> SEQUENCE: 207

Trp Tyr Gln Gln Leu Pro Gly Thr Ala Pro Lys Leu Leu Ile Tyr
1               5                   10                  15
```

<210> SEQ ID NO 208
<211> LENGTH: 32
<212> TYPE: PRT
<213> ORGANISM: Artificial Sequence
<220> FEATURE:
<223> OTHER INFORMATION: Synthetic construct

<400> SEQUENCE: 208

Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Gly Tyr Tyr Cys
            20                  25                  30

<210> SEQ ID NO 209
<211> LENGTH: 11
<212> TYPE: PRT
<213> ORGANISM: Artificial sequence
<220> FEATURE:
<223> OTHER INFORMATION: Synthetic construct

<400> SEQUENCE: 209

Phe Gly Gly Gly Thr Lys Leu Thr Val Leu Gly
1               5                   10

<210> SEQ ID NO 210
<211> LENGTH: 22
<212> TYPE: PRT
<213> ORGANISM: Artificial sequence
<220> FEATURE:
<223> OTHER INFORMATION: Synthetic construct

<400> SEQUENCE: 210

Glu Ser Val Leu Thr Gln Pro Pro Ser Val Ser Ala Ala Pro Gly Gln
1               5                   10                  15

Lys Val Thr Met Ser Cys
            20

<210> SEQ ID NO 211
<211> LENGTH: 22
<212> TYPE: PRT
<213> ORGANISM: Artificial sequence
<220> FEATURE:
<223> OTHER INFORMATION: Synthetic construct

<400> SEQUENCE: 211

Glu Ser Val Leu Thr Gln Pro Pro Ser Val Ser Ala Ala Pro Gly Gln
1               5                   10                  15

Lys Val Thr Met Ser Cys
            20

<210> SEQ ID NO 212
<211> LENGTH: 32
<212> TYPE: PRT
<213> ORGANISM: Artificial sequence
<220> FEATURE:
<223> OTHER INFORMATION: Synthetic construct

<400> SEQUENCE: 212

Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Asp Tyr Tyr Cys
            20                  25                  30

<210> SEQ ID NO 213
<211> LENGTH: 11

-continued

```
<212> TYPE: PRT
<213> ORGANISM: Artificial sequence
<220> FEATURE:
<223> OTHER INFORMATION: Synthetic construct

<400> SEQUENCE: 213

Phe Gly Gly Gly Thr Lys Leu Thr Val Leu Gly
1               5                   10

<210> SEQ ID NO 214
<211> LENGTH: 22
<212> TYPE: PRT
<213> ORGANISM: Artificial sequence
<220> FEATURE:
<223> OTHER INFORMATION: Synthetic construct

<400> SEQUENCE: 214

Glu Ala Val Val Thr Gln Pro Pro Ser Ala Ser Gly Thr Pro Gly Gln
1               5                   10                  15

Gly Val Thr Ile Ser Cys
            20

<210> SEQ ID NO 215
<211> LENGTH: 15
<212> TYPE: PRT
<213> ORGANISM: Artificial sequence
<220> FEATURE:
<223> OTHER INFORMATION: Synthetic construct

<400> SEQUENCE: 215

Trp Tyr Gln Gln Leu Pro Gly Thr Ala Pro Lys Leu Leu Ile Tyr
1               5                   10                  15

<210> SEQ ID NO 216
<211> LENGTH: 32
<212> TYPE: PRT
<213> ORGANISM: Artificial sequence
<220> FEATURE:
<223> OTHER INFORMATION: Synthetic construct

<400> SEQUENCE: 216

Gly Val Pro Asp Arg Phe Ser Gly Ser Lys Ser Ala Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 217
<211> LENGTH: 11
<212> TYPE: PRT
<213> ORGANISM: Artificial sequence
<220> FEATURE:
<223> OTHER INFORMATION: Synthetic construct

<400> SEQUENCE: 217

Phe Gly Thr Gly Thr Lys Leu Thr Val Leu Gly
1               5                   10

<210> SEQ ID NO 218
<211> LENGTH: 25
<212> TYPE: PRT
<213> ORGANISM: Artificial sequence
<220> FEATURE:
<223> OTHER INFORMATION: Synthetic construct

<400> SEQUENCE: 218

Glu Val Gln Leu Val Glu Ser Ala Gly Glu Val Gln Lys Pro Gly Glu
```

-continued

```
1               5               10              15

Ser Leu Arg Ile Ser Cys Lys Ala Ser
                20              25

<210> SEQ ID NO 219
<211> LENGTH: 14
<212> TYPE: PRT
<213> ORGANISM: Artificial sequence
<220> FEATURE:
<223> OTHER INFORMATION: Synthetic construct

<400> SEQUENCE: 219

Trp Val Arg Gln Leu Pro Gly Lys Gly Leu Glu Trp Met Gly
1               5               10

<210> SEQ ID NO 220
<211> LENGTH: 39
<212> TYPE: PRT
<213> ORGANISM: Artificial sequence
<220> FEATURE:
<223> OTHER INFORMATION: Synthetic construct

<400> SEQUENCE: 220

Tyr Ser Pro Ser Phe Gln Gly Gln Val Thr Met Ser Val Asp Lys Ser
1               5               10              15

Ile Asn Thr Ala Tyr Leu Gln Trp Asn Ser Leu Lys Val Ser Asp Thr
                20              25              30

Ala Thr Tyr Tyr Cys Val Arg
        35

<210> SEQ ID NO 221
<211> LENGTH: 11
<212> TYPE: PRT
<213> ORGANISM: Artificial sequence
<220> FEATURE:
<223> OTHER INFORMATION: Synthetic construct

<400> SEQUENCE: 221

Trp Gly Gln Gly Thr Thr Leu Thr Val Ser Ser
1               5               10

<210> SEQ ID NO 222
<211> LENGTH: 24
<212> TYPE: PRT
<213> ORGANISM: Artificial sequence
<220> FEATURE:
<223> OTHER INFORMATION: Synthetic construct

<400> SEQUENCE: 222

Met Gln Leu Val Gln Ser Gly Ala Glu Val Lys Lys Pro Gly Ala Ser
1               5               10              15

Val Lys Val Ser Cys Lys Thr Ser
                20

<210> SEQ ID NO 223
<211> LENGTH: 14
<212> TYPE: PRT
<213> ORGANISM: Artificial sequence
<220> FEATURE:
<223> OTHER INFORMATION: Synthetic construct

<400> SEQUENCE: 223

Trp Leu Arg Gln Ala Pro Gly Gln Gly Leu Glu Trp Met Gly
1               5               10
```

```
<210> SEQ ID NO 224
<211> LENGTH: 39
<212> TYPE: PRT
<213> ORGANISM: Artificial sequence
<220> FEATURE:
<223> OTHER INFORMATION: Synthetic construct

<400> SEQUENCE: 224

Tyr Ala Gln Lys Phe Gln Gly Arg Val Thr Met Thr Ala Asp Arg Ser
1               5                   10                  15

Thr Thr Thr Ala Tyr Met Glu Leu Arg Ser Leu Arg Ser Asp Asp Thr
            20                  25                  30

Ala Val Tyr Tyr Cys Ala Ser
        35

<210> SEQ ID NO 225
<211> LENGTH: 11
<212> TYPE: PRT
<213> ORGANISM: Artificial sequence
<220> FEATURE:
<223> OTHER INFORMATION: Synthetic construct

<400> SEQUENCE: 225

Trp Gly Gln Gly Thr Leu Leu Thr Val Ser Ser
1               5                   10

<210> SEQ ID NO 226
<211> LENGTH: 25
<212> TYPE: PRT
<213> ORGANISM: Artificial sequence
<220> FEATURE:
<223> OTHER INFORMATION: Synthetic construct

<400> SEQUENCE: 226

Glu Val Gln Leu Val Gln Ser Gly Ala Glu Val Lys Lys Pro Gly Ala
1               5                   10                  15

Ser Val Glu Val Ser Cys Lys Ala Ser
            20                  25

<210> SEQ ID NO 227
<211> LENGTH: 14
<212> TYPE: PRT
<213> ORGANISM: Artificial sequence
<220> FEATURE:
<223> OTHER INFORMATION: Synthetic construct

<400> SEQUENCE: 227

Trp Val Arg Gln Ala Pro Gly Gln Gly Leu Asp Trp Met Gly
1               5                   10

<210> SEQ ID NO 228
<211> LENGTH: 39
<212> TYPE: PRT
<213> ORGANISM: Artificial sequence
<220> FEATURE:
<223> OTHER INFORMATION: Synthetic construct

<400> SEQUENCE: 228

Tyr Ala Gln Asn Phe Lys Gly Arg Val Thr Met Thr Arg Asp Thr Ser
1               5                   10                  15

Ile Ser Thr Ala Tyr Leu Glu Leu Arg Ser Leu Thr Ser Asp Asp Thr
            20                  25                  30

Ala Val Tyr Phe Cys Ala Thr
        35
```

```
<210> SEQ ID NO 229
<211> LENGTH: 11
<212> TYPE: PRT
<213> ORGANISM: Artificial sequence
<220> FEATURE:
<223> OTHER INFORMATION: Synthetic construct

<400> SEQUENCE: 229

Trp Gly Gln Gly Thr Leu Leu Thr Val Ser Ser
1               5                   10

<210> SEQ ID NO 230
<211> LENGTH: 25
<212> TYPE: PRT
<213> ORGANISM: Artificial sequence
<220> FEATURE:
<223> OTHER INFORMATION: Synthetic construct

<400> SEQUENCE: 230

Glu Val Gln Leu Val Gln Ser Gly Ala Glu Val Lys Lys Pro Gly Ala
1               5                   10                  15

Ser Val Glu Val Ser Cys Lys Ala Ser
            20                  25

<210> SEQ ID NO 231
<211> LENGTH: 14
<212> TYPE: PRT
<213> ORGANISM: Artificial Sequence
<220> FEATURE:
<223> OTHER INFORMATION: Synthetic construct

<400> SEQUENCE: 231

Trp Val Arg Gln Ala Pro Gly Gln Gly Leu Asp Trp Met Gly
1               5                   10

<210> SEQ ID NO 232
<211> LENGTH: 39
<212> TYPE: PRT
<213> ORGANISM: Artificial sequence
<220> FEATURE:
<223> OTHER INFORMATION: Synthetic construct

<400> SEQUENCE: 232

Tyr Ala Gln Asn Phe Lys Gly Arg Val Thr Met Thr Arg Asp Thr Ser
1               5                   10                  15

Ile Ser Thr Ala Tyr Leu Glu Leu Arg Ser Leu Thr Ser Asp Asp Thr
            20                  25                  30

Ala Val Tyr Phe Cys Ala Thr
        35

<210> SEQ ID NO 233
<211> LENGTH: 11
<212> TYPE: PRT
<213> ORGANISM: Artificial sequence
<220> FEATURE:
<223> OTHER INFORMATION: Synthetic construct

<400> SEQUENCE: 233

Trp Gly Gln Gly Thr Met Leu Thr Val Ser Ser
1               5                   10

<210> SEQ ID NO 234
<211> LENGTH: 25
<212> TYPE: PRT
```

-continued

```
<213> ORGANISM: Artificial sequence
<220> FEATURE:
<223> OTHER INFORMATION: Synthetic construct

<400> SEQUENCE: 234

Glu Val Gln Leu Val Gln Ser Gly Ala Glu Val Lys Lys Pro Gly Ala
1               5                   10                  15

Ser Val Glu Val Ser Cys Lys Ala Ser
            20                  25

<210> SEQ ID NO 235
<211> LENGTH: 14
<212> TYPE: PRT
<213> ORGANISM: Artificial sequence
<220> FEATURE:
<223> OTHER INFORMATION: Synthetic construct

<400> SEQUENCE: 235

Trp Val Arg Gln Ala Pro Gly Gln Gly Leu Asp Trp Met Gly
1               5                   10

<210> SEQ ID NO 236
<211> LENGTH: 39
<212> TYPE: PRT
<213> ORGANISM: Artificial sequence
<220> FEATURE:
<223> OTHER INFORMATION: Synthetic construct

<400> SEQUENCE: 236

Tyr Ala Gln Asn Phe Lys Gly Arg Val Thr Met Thr Arg Asp Thr Ser
1               5                   10                  15

Ile Ser Thr Ala Tyr Leu Glu Leu Arg Ser Leu Thr Ser Asp Asp Thr
            20                  25                  30

Ala Val Tyr Phe Cys Ala Thr
        35

<210> SEQ ID NO 237
<211> LENGTH: 11
<212> TYPE: PRT
<213> ORGANISM: Artificial sequence
<220> FEATURE:
<223> OTHER INFORMATION: Synthetic construct

<400> SEQUENCE: 237

Trp Gly Gln Gly Thr Met Leu Thr Val Ser Ser
1               5                   10

<210> SEQ ID NO 238
<211> LENGTH: 25
<212> TYPE: PRT
<213> ORGANISM: Artificial sequence
<220> FEATURE:
<223> OTHER INFORMATION: Synthetic construct

<400> SEQUENCE: 238

Glu Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 239
<211> LENGTH: 14
<212> TYPE: PRT
<213> ORGANISM: Artificial sequence
<220> FEATURE:
```

<223> OTHER INFORMATION: Synthetic construct

<400> SEQUENCE: 239

Trp Val Arg Gln Ala Pro Gly Gln Gly Leu Asp Trp Met Gly
1               5                   10

<210> SEQ ID NO 240
<211> LENGTH: 39
<212> TYPE: PRT
<213> ORGANISM: Artificial sequence
<220> FEATURE:
<223> OTHER INFORMATION: Synthetic construct

<400> SEQUENCE: 240

Tyr Ala Gln Asn Phe Lys Gly Arg Val Thr Met Thr Arg Asp Thr Ser
1               5                   10                  15

Ile Ser Thr Ala Tyr Leu Glu Leu Arg Ser Leu Thr Ser Asp Asp Thr
            20                  25                  30

Ala Val Tyr Phe Cys Ala Thr
        35

<210> SEQ ID NO 241
<211> LENGTH: 11
<212> TYPE: PRT
<213> ORGANISM: Artificial sequence
<220> FEATURE:
<223> OTHER INFORMATION: Synthetic construct

<400> SEQUENCE: 241

Trp Gly Gln Gly Thr Met Leu Thr Val Ser Ser
1               5                   10

<210> SEQ ID NO 242
<211> LENGTH: 22
<212> TYPE: PRT
<213> ORGANISM: Artificial sequence
<220> FEATURE:
<223> OTHER INFORMATION: Synthetic construct

<400> SEQUENCE: 242

Glu Ser Ala Leu Thr Gln Pro Ala Ser Val Ser Gly Ser Pro Gly Gln
1               5                   10                  15

Ser Ile Thr Ile Ser Cys
            20

<210> SEQ ID NO 243
<211> LENGTH: 15
<212> TYPE: PRT
<213> ORGANISM: Artificial sequence
<220> FEATURE:
<223> OTHER INFORMATION: Synthetic construct

<400> SEQUENCE: 243

Trp Tyr Gln Gln His Pro Gly Lys Ala Pro Lys Leu Met Ile Tyr
1               5                   10                  15

<210> SEQ ID NO 244
<211> LENGTH: 32
<212> TYPE: PRT
<213> ORGANISM: Artificial sequence
<220> FEATURE:
<223> OTHER INFORMATION: Synthetic construct

<400> SEQUENCE: 244

Gly Val Ser Asn Arg Phe Ser Gly Ser Lys Ser Gly Asn Thr Ala Ser

-continued

```
1               5                   10                  15

Leu Thr Ile Ser Gly Leu Gln Ala Glu Asp Glu Ala Asp Tyr Tyr Cys
            20                  25                  30
```

<210> SEQ ID NO 245
<211> LENGTH: 11
<212> TYPE: PRT
<213> ORGANISM: Artificial sequence
<220> FEATURE:
<223> OTHER INFORMATION: Synthetic construct

<400> SEQUENCE: 245

```
Phe Gly Gly Gly Thr Lys Leu Thr Val Leu Gly
1               5                   10
```

<210> SEQ ID NO 246
<211> LENGTH: 20
<212> TYPE: PRT
<213> ORGANISM: Artificial sequence
<220> FEATURE:
<223> OTHER INFORMATION: Synthetic construct

<400> SEQUENCE: 246

```
Val Leu Thr Gln Glu Pro Ser Leu Thr Val Ser Pro Gly Gly Thr Val
1               5                   10                  15

Thr Leu Thr Cys
            20
```

<210> SEQ ID NO 247
<211> LENGTH: 15
<212> TYPE: PRT
<213> ORGANISM: Artificial sequence
<220> FEATURE:
<223> OTHER INFORMATION: Synthetic construct

<400> SEQUENCE: 247

```
Trp Phe Gln Gln Lys Pro Gly Gln Ala Pro Arg Ala Leu Ile Tyr
1               5                   10                  15
```

<210> SEQ ID NO 248
<211> LENGTH: 32
<212> TYPE: PRT
<213> ORGANISM: Artificial sequence
<220> FEATURE:
<223> OTHER INFORMATION: Synthetic construct

<400> SEQUENCE: 248

```
Trp Thr Pro Ala Arg Phe Ser Gly Ser Leu Leu Gly Gly Lys Ala Ala
1               5                   10                  15

Leu Thr Leu Ser Gly Val Gln Pro Glu Asp Glu Ala Glu Tyr Tyr Cys
            20                  25                  30
```

<210> SEQ ID NO 249
<211> LENGTH: 10
<212> TYPE: PRT
<213> ORGANISM: Artificial sequence
<220> FEATURE:
<223> OTHER INFORMATION: Synthetic construct

<400> SEQUENCE: 249

```
Phe Gly Gly Gly Thr Lys Leu Thr Val Leu
1               5                   10
```

<210> SEQ ID NO 250
<211> LENGTH: 22

```
<212> TYPE: PRT
<213> ORGANISM: Artificial sequence
<220> FEATURE:
<223> OTHER INFORMATION: Synthetic construct

<400> SEQUENCE: 250

Glu Ser Val Leu Thr Gln Pro Pro Ser Ile Ser Ala Ala Pro Gly Gln
1               5                   10                  15

Arg Val Thr Ile Pro Cys
            20

<210> SEQ ID NO 251
<211> LENGTH: 15
<212> TYPE: PRT
<213> ORGANISM: Artificial sequence
<220> FEATURE:
<223> OTHER INFORMATION: Synthetic construct

<400> SEQUENCE: 251

Trp Tyr Gln Gln Leu Pro Gly Ala Ala Pro Lys Leu Leu Ile Tyr
1               5                   10                  15

<210> SEQ ID NO 252
<211> LENGTH: 32
<212> TYPE: PRT
<213> ORGANISM: Artificial sequence
<220> FEATURE:
<223> OTHER INFORMATION: Synthetic construct

<400> SEQUENCE: 252

Gly Ile Pro Asp Arg Phe Ser Gly Ser Lys Ser Gly Thr Ser Ala Ser
1               5                   10                  15

Leu Gly Ile Thr Gly Leu Gln Thr Gly Asp Glu Ala Asp Tyr Tyr Cys
            20                  25                  30

<210> SEQ ID NO 253
<211> LENGTH: 11
<212> TYPE: PRT
<213> ORGANISM: Artificial sequence
<220> FEATURE:
<223> OTHER INFORMATION: Synthetic construct

<400> SEQUENCE: 253

Phe Gly Gly Gly Thr Lys Val Thr Val Leu Gly
1               5                   10

<210> SEQ ID NO 254
<211> LENGTH: 22
<212> TYPE: PRT
<213> ORGANISM: Artificial sequence
<220> FEATURE:
<223> OTHER INFORMATION: Synthetic construct

<400> SEQUENCE: 254

Glu Ser Val Leu Thr Gln Pro Pro Ser Val Ser Ala Ala Pro Gly Gln
1               5                   10                  15

Lys Val Thr Ile Ser Cys
            20

<210> SEQ ID NO 255
<211> LENGTH: 15
<212> TYPE: PRT
<213> ORGANISM: Artificial sequence
<220> FEATURE:
<223> OTHER INFORMATION: Synthetic construct
```

-continued

```
<400> SEQUENCE: 255

Trp Tyr Gln Gln Leu Pro Gly Thr Ala Pro Lys Leu Leu Ile Tyr
1               5                   10                  15

<210> SEQ ID NO 256
<211> LENGTH: 32
<212> TYPE: PRT
<213> ORGANISM: Artificial sequence
<220> FEATURE:
<223> OTHER INFORMATION: Synthetic construct

<400> SEQUENCE: 256

Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Gly Tyr Tyr Cys
            20                  25                  30

<210> SEQ ID NO 257
<211> LENGTH: 11
<212> TYPE: PRT
<213> ORGANISM: Artificial sequence
<220> FEATURE:
<223> OTHER INFORMATION: Synthetic construct

<400> SEQUENCE: 257

Phe Gly Gly Gly Thr Lys Leu Thr Val Leu Gly
1               5                   10

<210> SEQ ID NO 258
<211> LENGTH: 22
<212> TYPE: PRT
<213> ORGANISM: Artificial sequence
<220> FEATURE:
<223> OTHER INFORMATION: Synthetic construct

<400> SEQUENCE: 258

Glu Ser Val Leu Thr Gln Pro Pro Ser Val Ser Ala Ala Pro Gly Gln
1               5                   10                  15

Lys Val Thr Met Ser Cys
            20

<210> SEQ ID NO 259
<211> LENGTH: 15
<212> TYPE: PRT
<213> ORGANISM: Artificial sequence
<220> FEATURE:
<223> OTHER INFORMATION: Synthetic construct

<400> SEQUENCE: 259

Trp Tyr Gln His Leu Pro Gly Thr Ala Pro Lys Leu Leu Leu Phe
1               5                   10                  15

<210> SEQ ID NO 260
<211> LENGTH: 32
<212> TYPE: PRT
<213> ORGANISM: Artificial sequence
<220> FEATURE:
<223> OTHER INFORMATION: Synthetic construct

<400> SEQUENCE: 260

Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Asp Tyr Tyr Cys
            20                  25                  30
```

-continued

```
<210> SEQ ID NO 261
<211> LENGTH: 11
<212> TYPE: PRT
<213> ORGANISM: Artificial sequence
<220> FEATURE:
<223> OTHER INFORMATION: Synthetic construct

<400> SEQUENCE: 261

Phe Gly Gly Gly Thr Lys Leu Thr Val Leu Gly
1               5                   10

<210> SEQ ID NO 262
<211> LENGTH: 22
<212> TYPE: PRT
<213> ORGANISM: Artificial sequence
<220> FEATURE:
<223> OTHER INFORMATION: Synthetic construct

<400> SEQUENCE: 262

Glu Ala Val Val Thr Gln Pro Pro Ser Ala Ser Gly Thr Pro Gly Gln
1               5                   10                  15

Gly Val Thr Ile Ser Cys
            20

<210> SEQ ID NO 263
<211> LENGTH: 15
<212> TYPE: PRT
<213> ORGANISM: Artificial sequence
<220> FEATURE:
<223> OTHER INFORMATION: Synthetic construct

<400> SEQUENCE: 263

Trp Tyr Gln Gln Leu Pro Gly Thr Ala Pro Lys Leu Leu Ile Tyr
1               5                   10                  15

<210> SEQ ID NO 264
<211> LENGTH: 32
<212> TYPE: PRT
<213> ORGANISM: Artificial sequence
<220> FEATURE:
<223> OTHER INFORMATION: Synthetic construct

<400> SEQUENCE: 264

Gly Val Pro Asp Arg Phe Ser Gly Ser Lys Ser Ala Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 265
<211> LENGTH: 11
<212> TYPE: PRT
<213> ORGANISM: Artificial sequence
<220> FEATURE:
<223> OTHER INFORMATION: Synthetic construct

<400> SEQUENCE: 265

Phe Gly Thr Gly Thr Lys Leu Thr Val Leu Gly
1               5                   10

<210> SEQ ID NO 266
<211> LENGTH: 30
<212> TYPE: PRT
<213> ORGANISM: Artificial sequence
<220> FEATURE:
<223> OTHER INFORMATION: Synthetic construct
```

```
<400> SEQUENCE: 266

Glu Val Gln Leu Val Glu Ser Ala Gly Glu Val Gln Lys Pro Gly Glu
1               5                   10                  15

Ser Leu Arg Ile Ser Cys Lys Ala Ser Gly Tyr Thr Phe Ser
            20                  25                  30

<210> SEQ ID NO 267
<211> LENGTH: 14
<212> TYPE: PRT
<213> ORGANISM: Artificial sequence
<220> FEATURE:
<223> OTHER INFORMATION: Synthetic construct

<400> SEQUENCE: 267

Trp Val Arg Gln Leu Pro Gly Lys Gly Leu Glu Trp Met Gly
1               5                   10

<210> SEQ ID NO 268
<211> LENGTH: 32
<212> TYPE: PRT
<213> ORGANISM: Artificial sequence
<220> FEATURE:
<223> OTHER INFORMATION: Synthetic construct

<400> SEQUENCE: 268

Gln Val Thr Met Ser Val Asp Lys Ser Ile Asn Thr Ala Tyr Leu Gln
1               5                   10                  15

Trp Asn Ser Leu Lys Val Ser Asp Thr Ala Thr Tyr Tyr Cys Val Arg
            20                  25                  30

<210> SEQ ID NO 269
<211> LENGTH: 11
<212> TYPE: PRT
<213> ORGANISM: Artificial sequence
<220> FEATURE:
<223> OTHER INFORMATION: Synthetic construct

<400> SEQUENCE: 269

Trp Gly Gln Gly Thr Thr Leu Thr Val Ser Ser
1               5                   10

<210> SEQ ID NO 270
<211> LENGTH: 29
<212> TYPE: PRT
<213> ORGANISM: Artificial sequence
<220> FEATURE:
<223> OTHER INFORMATION: Synthetic construct

<400> SEQUENCE: 270

Met Gln Leu Val Gln Ser Gly Ala Glu Val Lys Lys Pro Gly Ala Ser
1               5                   10                  15

Val Lys Val Ser Cys Lys Thr Ser Gly Tyr Asn Phe Asn
            20                  25

<210> SEQ ID NO 271
<211> LENGTH: 14
<212> TYPE: PRT
<213> ORGANISM: Artificial sequence
<220> FEATURE:
<223> OTHER INFORMATION: Synthetic construct

<400> SEQUENCE: 271

Trp Leu Arg Gln Ala Pro Gly Gln Gly Leu Glu Trp Met Gly
1               5                   10
```

-continued

```
<210> SEQ ID NO 272
<211> LENGTH: 32
<212> TYPE: PRT
<213> ORGANISM: Artificial sequence
<220> FEATURE:
<223> OTHER INFORMATION: Synthetic construct

<400> SEQUENCE: 272

Arg Val Thr Met Thr Ala Asp Arg Ser Thr Thr Thr Ala Tyr Met Glu
1               5                   10                  15

Leu Arg Ser Leu Arg Ser Asp Asp Thr Ala Val Tyr Tyr Cys Ala Ser
            20                  25                  30

<210> SEQ ID NO 273
<211> LENGTH: 11
<212> TYPE: PRT
<213> ORGANISM: Artificial sequence
<220> FEATURE:
<223> OTHER INFORMATION: Synthetic construct

<400> SEQUENCE: 273

Trp Gly Gln Gly Thr Leu Leu Thr Val Ser Ser
1               5                   10

<210> SEQ ID NO 274
<211> LENGTH: 30
<212> TYPE: PRT
<213> ORGANISM: Artificial sequence
<220> FEATURE:
<223> OTHER INFORMATION: Synthetic construct

<400> SEQUENCE: 274

Glu Val Gln Leu Val Gln Ser Gly Ala Glu Val Lys Lys Pro Gly Ala
1               5                   10                  15

Ser Val Glu Val Ser Cys Lys Ala Ser Gly Tyr Thr Phe Asn
            20                  25                  30

<210> SEQ ID NO 275
<211> LENGTH: 14
<212> TYPE: PRT
<213> ORGANISM: Artificial sequence
<220> FEATURE:
<223> OTHER INFORMATION: Synthetic construct

<400> SEQUENCE: 275

Trp Val Arg Gln Ala Pro Gly Gln Gly Leu Asp Trp Met Gly
1               5                   10

<210> SEQ ID NO 276
<211> LENGTH: 32
<212> TYPE: PRT
<213> ORGANISM: Artificial sequence
<220> FEATURE:
<223> OTHER INFORMATION: Synthetic construct

<400> SEQUENCE: 276

Arg Val Thr Met Thr Arg Asp Thr Ser Ile Ser Thr Ala Tyr Leu Glu
1               5                   10                  15

Leu Arg Ser Leu Thr Ser Asp Asp Thr Ala Val Tyr Phe Cys Ala Thr
            20                  25                  30

<210> SEQ ID NO 277
<211> LENGTH: 11
<212> TYPE: PRT
<213> ORGANISM: Artificial sequence
```

-continued

```
<220> FEATURE:
<223> OTHER INFORMATION: Synthetic construct

<400> SEQUENCE: 277

Trp Gly Gln Gly Thr Leu Leu Thr Val Ser Ser
1               5                   10

<210> SEQ ID NO 278
<211> LENGTH: 30
<212> TYPE: PRT
<213> ORGANISM: Artificial sequence
<220> FEATURE:
<223> OTHER INFORMATION: Synthetic construct

<400> SEQUENCE: 278

Glu Val Gln Leu Val Gln Ser Gly Ala Glu Val Lys Lys Pro Gly Ala
1               5                   10                  15

Ser Val Glu Val Ser Cys Lys Ala Ser Gly Tyr Thr Phe Asn
            20                  25                  30

<210> SEQ ID NO 279
<211> LENGTH: 14
<212> TYPE: PRT
<213> ORGANISM: Artificial sequence
<220> FEATURE:
<223> OTHER INFORMATION: Synthetic construct

<400> SEQUENCE: 279

Trp Val Arg Gln Ala Pro Gly Gln Gly Leu Asp Trp Met Gly
1               5                   10

<210> SEQ ID NO 280
<211> LENGTH: 32
<212> TYPE: PRT
<213> ORGANISM: Artificial sequence
<220> FEATURE:
<223> OTHER INFORMATION: Synthetic construct

<400> SEQUENCE: 280

Arg Val Thr Met Thr Arg Asp Thr Ser Ile Ser Thr Ala Tyr Leu Glu
1               5                   10                  15

Leu Arg Ser Leu Thr Ser Asp Asp Thr Ala Val Tyr Phe Cys Ala Thr
            20                  25                  30

<210> SEQ ID NO 281
<211> LENGTH: 11
<212> TYPE: PRT
<213> ORGANISM: Artificial sequence
<220> FEATURE:
<223> OTHER INFORMATION: Synthetic construct

<400> SEQUENCE: 281

Trp Gly Gln Gly Thr Met Leu Thr Val Ser Ser
1               5                   10

<210> SEQ ID NO 282
<211> LENGTH: 30
<212> TYPE: PRT
<213> ORGANISM: Artificial sequence
<220> FEATURE:
<223> OTHER INFORMATION: Synthetic construct

<400> SEQUENCE: 282

Glu Val Gln Leu Val Gln Ser Gly Ala Glu Val Lys Lys Pro Gly Ala
1               5                   10                  15
```

Ser Val Glu Val Ser Cys Lys Ala Ser Gly Tyr Thr Phe Asn
            20                  25                  30

<210> SEQ ID NO 283
<211> LENGTH: 14
<212> TYPE: PRT
<213> ORGANISM: Artificial sequence
<220> FEATURE:
<223> OTHER INFORMATION: Synthetic construct

<400> SEQUENCE: 283

Trp Val Arg Gln Ala Pro Gly Gln Gly Leu Asp Trp Met Gly
1               5                   10

<210> SEQ ID NO 284
<211> LENGTH: 32
<212> TYPE: PRT
<213> ORGANISM: Artificial sequence
<220> FEATURE:
<223> OTHER INFORMATION: Synthetic construct

<400> SEQUENCE: 284

Arg Val Thr Met Thr Arg Asp Thr Ser Ile Ser Thr Ala Tyr Leu Glu
1               5                   10                  15

Leu Arg Ser Leu Thr Ser Asp Asp Thr Ala Val Tyr Phe Cys Ala Thr
            20                  25                  30

<210> SEQ ID NO 285
<211> LENGTH: 11
<212> TYPE: PRT
<213> ORGANISM: Artificial sequence
<220> FEATURE:
<223> OTHER INFORMATION: Synthetic construct

<400> SEQUENCE: 285

Trp Gly Gln Gly Thr Met Leu Thr Val Ser Ser
1               5                   10

<210> SEQ ID NO 286
<211> LENGTH: 30
<212> TYPE: PRT
<213> ORGANISM: Artificial sequence
<220> FEATURE:
<223> OTHER INFORMATION: Synthetic construct

<400> SEQUENCE: 286

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn
            20                  25                  30

<210> SEQ ID NO 287
<211> LENGTH: 14
<212> TYPE: PRT
<213> ORGANISM: Artificial sequence
<220> FEATURE:
<223> OTHER INFORMATION: Synthetic construct

<400> SEQUENCE: 287

Trp Val Arg Gln Ala Pro Gly Gln Gly Leu Asp Trp Met Gly
1               5                   10

<210> SEQ ID NO 288
<211> LENGTH: 32
<212> TYPE: PRT
<213> ORGANISM: Artificial sequence

```
<220> FEATURE:
<223> OTHER INFORMATION: Synthetic construct

<400> SEQUENCE: 288

Arg Val Thr Met Thr Arg Asp Thr Ser Ile Ser Thr Ala Tyr Leu Glu
1               5                   10                  15

Leu Arg Ser Leu Thr Ser Asp Asp Thr Ala Val Tyr Phe Cys Ala Thr
            20                  25                  30

<210> SEQ ID NO 289
<211> LENGTH: 11
<212> TYPE: PRT
<213> ORGANISM: Artificial sequence
<220> FEATURE:
<223> OTHER INFORMATION: Synthetic construct

<400> SEQUENCE: 289

Trp Gly Gln Gly Thr Met Leu Thr Val Ser Ser
1               5                   10

<210> SEQ ID NO 290
<211> LENGTH: 22
<212> TYPE: PRT
<213> ORGANISM: Artificial sequence
<220> FEATURE:
<223> OTHER INFORMATION: Synthetic construct

<400> SEQUENCE: 290

Glu Ser Ala Leu Thr Gln Pro Ala Ser Val Ser Gly Ser Pro Gly Gln
1               5                   10                  15

Ser Ile Thr Ile Ser Cys
            20

<210> SEQ ID NO 291
<211> LENGTH: 15
<212> TYPE: PRT
<213> ORGANISM: Artificial Sequence
<220> FEATURE:
<223> OTHER INFORMATION: Synthetic construct

<400> SEQUENCE: 291

Trp Tyr Gln Gln His Pro Gly Lys Ala Pro Lys Leu Met Ile Tyr
1               5                   10                  15

<210> SEQ ID NO 292
<211> LENGTH: 32
<212> TYPE: PRT
<213> ORGANISM: Artificial sequence
<220> FEATURE:
<223> OTHER INFORMATION: Synthetic construct

<400> SEQUENCE: 292

Gly Val Ser Asn Arg Phe Ser Gly Ser Lys Ser Gly Asn Thr Ala Ser
1               5                   10                  15

Leu Thr Ile Ser Gly Leu Gln Ala Glu Asp Glu Ala Asp Tyr Tyr Cys
            20                  25                  30

<210> SEQ ID NO 293
<211> LENGTH: 11
<212> TYPE: PRT
<213> ORGANISM: Artificial sequence
<220> FEATURE:
<223> OTHER INFORMATION: Synthetic construct

<400> SEQUENCE: 293
```

```
Phe Gly Gly Gly Thr Lys Leu Thr Val Leu Gly
1               5                   10

<210> SEQ ID NO 294
<211> LENGTH: 20
<212> TYPE: PRT
<213> ORGANISM: Artificial sequence
<220> FEATURE:
<223> OTHER INFORMATION: Synthetic construct

<400> SEQUENCE: 294

Val Leu Thr Gln Glu Pro Ser Leu Thr Val Ser Pro Gly Gly Thr Val
1               5                   10                  15

Thr Leu Thr Cys
            20

<210> SEQ ID NO 295
<211> LENGTH: 15
<212> TYPE: PRT
<213> ORGANISM: Artificial sequence
<220> FEATURE:
<223> OTHER INFORMATION: Synthetic construct

<400> SEQUENCE: 295

Trp Phe Gln Gln Lys Pro Gly Gln Ala Pro Arg Ala Leu Ile Tyr
1               5                   10                  15

<210> SEQ ID NO 296
<211> LENGTH: 32
<212> TYPE: PRT
<213> ORGANISM: Artificial sequence
<220> FEATURE:
<223> OTHER INFORMATION: Synthetic construct

<400> SEQUENCE: 296

Trp Thr Pro Ala Arg Phe Ser Gly Ser Leu Leu Gly Gly Lys Ala Ala
1               5                   10                  15

Leu Thr Leu Ser Gly Val Gln Pro Glu Asp Glu Ala Glu Tyr Tyr Cys
            20                  25                  30

<210> SEQ ID NO 297
<211> LENGTH: 10
<212> TYPE: PRT
<213> ORGANISM: Artificial sequence
<220> FEATURE:
<223> OTHER INFORMATION: Synthetic construct

<400> SEQUENCE: 297

Phe Gly Gly Gly Thr Lys Leu Thr Val Leu
1               5                   10

<210> SEQ ID NO 298
<211> LENGTH: 22
<212> TYPE: PRT
<213> ORGANISM: Artificial sequence
<220> FEATURE:
<223> OTHER INFORMATION: Synthetic construct

<400> SEQUENCE: 298

Glu Ser Val Leu Thr Gln Pro Pro Ser Ile Ser Ala Ala Pro Gly Gln
1               5                   10                  15

Arg Val Thr Ile Pro Cys
            20

<210> SEQ ID NO 299
```

-continued

```
<211> LENGTH: 15
<212> TYPE: PRT
<213> ORGANISM: Artificial sequence
<220> FEATURE:
<223> OTHER INFORMATION: Synthetic construct

<400> SEQUENCE: 299

Trp Tyr Gln Gln Leu Pro Gly Ala Ala Pro Lys Leu Leu Ile Tyr
1               5                   10                  15

<210> SEQ ID NO 300
<211> LENGTH: 32
<212> TYPE: PRT
<213> ORGANISM: Artificial sequence
<220> FEATURE:
<223> OTHER INFORMATION: Synthetic construct

<400> SEQUENCE: 300

Gly Ile Pro Asp Arg Phe Ser Gly Ser Lys Ser Gly Thr Ser Ala Ser
1               5                   10                  15

Leu Gly Ile Thr Gly Leu Gln Thr Gly Asp Glu Ala Asp Tyr Tyr Cys
            20                  25                  30

<210> SEQ ID NO 301
<211> LENGTH: 11
<212> TYPE: PRT
<213> ORGANISM: Artificial sequence
<220> FEATURE:
<223> OTHER INFORMATION: Synthetic construct

<400> SEQUENCE: 301

Phe Gly Gly Gly Thr Lys Val Thr Val Leu Gly
1               5                   10

<210> SEQ ID NO 302
<211> LENGTH: 22
<212> TYPE: PRT
<213> ORGANISM: Artificial sequence
<220> FEATURE:
<223> OTHER INFORMATION: Synthetic construct

<400> SEQUENCE: 302

Glu Ser Val Leu Thr Gln Pro Pro Ser Val Ser Ala Ala Pro Gly Gln
1               5                   10                  15

Lys Val Thr Ile Ser Cys
            20

<210> SEQ ID NO 303
<211> LENGTH: 15
<212> TYPE: PRT
<213> ORGANISM: Artificial sequence
<220> FEATURE:
<223> OTHER INFORMATION: Synthetic construct

<400> SEQUENCE: 303

Trp Tyr Gln Gln Leu Pro Gly Thr Ala Pro Lys Leu Leu Ile Tyr
1               5                   10                  15

<210> SEQ ID NO 304
<211> LENGTH: 32
<212> TYPE: PRT
<213> ORGANISM: Artificial sequence
<220> FEATURE:
<223> OTHER INFORMATION: Synthetic construct

<400> SEQUENCE: 304
```

```
Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Gly Tyr Tyr Cys
            20                  25                  30

<210> SEQ ID NO 305
<211> LENGTH: 11
<212> TYPE: PRT
<213> ORGANISM: Artificial sequence
<220> FEATURE:
<223> OTHER INFORMATION: Synthetic construct

<400> SEQUENCE: 305

Phe Gly Gly Gly Thr Lys Leu Thr Val Leu Gly
1               5                   10

<210> SEQ ID NO 306
<211> LENGTH: 22
<212> TYPE: PRT
<213> ORGANISM: Artificial sequence
<220> FEATURE:
<223> OTHER INFORMATION: Synthetic construct

<400> SEQUENCE: 306

Glu Ser Val Leu Thr Gln Pro Pro Ser Val Ser Ala Ala Pro Gly Gln
1               5                   10                  15

Lys Val Thr Met Ser Cys
            20

<210> SEQ ID NO 307
<211> LENGTH: 15
<212> TYPE: PRT
<213> ORGANISM: Artificial sequence
<220> FEATURE:
<223> OTHER INFORMATION: Synthetic construct

<400> SEQUENCE: 307

Trp Tyr Gln His Leu Pro Gly Thr Ala Pro Lys Leu Leu Leu Phe
1               5                   10                  15

<210> SEQ ID NO 308
<211> LENGTH: 32
<212> TYPE: PRT
<213> ORGANISM: Artificial sequence
<220> FEATURE:
<223> OTHER INFORMATION: Synthetic construct

<400> SEQUENCE: 308

Gly Ile Pro Asp Arg Phe Ser Gly Ser Lys Ser Gly Thr Ser Ala Thr
1               5                   10                  15

Leu Gly Ile Thr Gly Leu Gln Thr Gly Asp Glu Ala Asp Tyr Tyr Cys
            20                  25                  30

<210> SEQ ID NO 309
<211> LENGTH: 11
<212> TYPE: PRT
<213> ORGANISM: Artificial sequence
<220> FEATURE:
<223> OTHER INFORMATION: Synthetic construct

<400> SEQUENCE: 309

Phe Gly Gly Gly Thr Lys Leu Thr Val Leu Gly
1               5                   10

<210> SEQ ID NO 310
```

```
<211> LENGTH: 22
<212> TYPE: PRT
<213> ORGANISM: Artificial sequence
<220> FEATURE:
<223> OTHER INFORMATION: Synthetic construct

<400> SEQUENCE: 310

Glu Ala Val Val Thr Gln Pro Pro Ser Ala Ser Gly Thr Pro Gly Gln
1               5                   10                  15

Gly Val Thr Ile Ser Cys
            20

<210> SEQ ID NO 311
<211> LENGTH: 15
<212> TYPE: PRT
<213> ORGANISM: Artificial sequence
<220> FEATURE:
<223> OTHER INFORMATION: Synthetic construct

<400> SEQUENCE: 311

Trp Tyr Gln Gln Leu Pro Gly Thr Ala Pro Lys Leu Leu Ile Tyr
1               5                   10                  15

<210> SEQ ID NO 312
<211> LENGTH: 32
<212> TYPE: PRT
<213> ORGANISM: Artificial sequence
<220> FEATURE:
<223> OTHER INFORMATION: Synthetic construct

<400> SEQUENCE: 312

Gly Val Pro Asp Arg Phe Ser Gly Ser Lys Ser Ala Thr Ser Ala Ser
1               5                   10                  15

Leu Ala Ile Ser Gly Leu Arg Ser Glu Asp Glu Ala Asp Tyr Tyr Cys
            20                  25                  30

<210> SEQ ID NO 313
<211> LENGTH: 11
<212> TYPE: PRT
<213> ORGANISM: Artificial sequence
<220> FEATURE:
<223> OTHER INFORMATION: Synthetic construct

<400> SEQUENCE: 313

Phe Gly Thr Gly Thr Lys Leu Thr Val Leu Gly
1               5                   10

<210> SEQ ID NO 314
<211> LENGTH: 29
<212> TYPE: PRT
<213> ORGANISM: Artificial sequence
<220> FEATURE:
<223> OTHER INFORMATION: Synthetic construct

<400> SEQUENCE: 314

Glu Val Gln Leu Val Glu Ser Ala Gly Glu Val Gln Lys Pro Gly Glu
1               5                   10                  15

Ser Leu Arg Ile Ser Cys Lys Ala Ser Gly Tyr Thr Phe
            20                  25

<210> SEQ ID NO 315
<211> LENGTH: 11
<212> TYPE: PRT
<213> ORGANISM: Artificial sequence
<220> FEATURE:
<223> OTHER INFORMATION: Synthetic construct
```

<400> SEQUENCE: 315

Trp Val Arg Gln Leu Pro Gly Lys Gly Leu Glu
1               5                   10

<210> SEQ ID NO 316
<211> LENGTH: 37
<212> TYPE: PRT
<213> ORGANISM: Artificial sequence
<220> FEATURE:
<223> OTHER INFORMATION: Synthetic construct

<400> SEQUENCE: 316

Tyr Ser Pro Ser Phe Gln Gly Gln Val Thr Met Ser Val Asp Lys Ser
1               5                   10                  15

Ile Asn Thr Ala Tyr Leu Gln Trp Asn Ser Leu Lys Val Ser Asp Thr
            20                  25                  30

Ala Thr Tyr Tyr Cys
        35

<210> SEQ ID NO 317
<211> LENGTH: 12
<212> TYPE: PRT
<213> ORGANISM: Artificial sequence
<220> FEATURE:
<223> OTHER INFORMATION: Synthetic construct

<400> SEQUENCE: 317

Pro Trp Gly Gln Gly Thr Thr Leu Thr Val Ser Ser
1               5                   10

<210> SEQ ID NO 318
<211> LENGTH: 28
<212> TYPE: PRT
<213> ORGANISM: Artificial sequence
<220> FEATURE:
<223> OTHER INFORMATION: Synthetic construct

<400> SEQUENCE: 318

Met Gln Leu Val Gln Ser Gly Ala Glu Val Lys Lys Pro Gly Ala Ser
1               5                   10                  15

Val Lys Val Ser Cys Lys Thr Ser Gly Tyr Asn Phe
            20                  25

<210> SEQ ID NO 319
<211> LENGTH: 11
<212> TYPE: PRT
<213> ORGANISM: Artificial sequence
<220> FEATURE:
<223> OTHER INFORMATION: Synthetic construct

<400> SEQUENCE: 319

Trp Leu Arg Gln Ala Pro Gly Gln Gly Leu Glu
1               5                   10

<210> SEQ ID NO 320
<211> LENGTH: 37
<212> TYPE: PRT
<213> ORGANISM: Artificial sequence
<220> FEATURE:
<223> OTHER INFORMATION: Synthetic construct

<400> SEQUENCE: 320

Tyr Ala Gln Lys Phe Gln Gly Arg Val Thr Met Thr Ala Asp Arg Ser
1               5                   10                  15

```
Thr Thr Thr Ala Tyr Met Glu Leu Arg Ser Leu Arg Ser Asp Asp Thr
              20                  25                  30

Ala Val Tyr Tyr Cys
      35

<210> SEQ ID NO 321
<211> LENGTH: 12
<212> TYPE: PRT
<213> ORGANISM: Artificial sequence
<220> FEATURE:
<223> OTHER INFORMATION: Synthetic construct

<400> SEQUENCE: 321

His Trp Gly Gln Gly Thr Leu Leu Thr Val Ser Ser
1               5                   10

<210> SEQ ID NO 322
<211> LENGTH: 29
<212> TYPE: PRT
<213> ORGANISM: Artificial sequence
<220> FEATURE:
<223> OTHER INFORMATION: Synthetic construct

<400> SEQUENCE: 322

Glu Val Gln Leu Val Gln Ser Gly Ala Glu Val Lys Lys Pro Gly Ala
1               5                   10                  15

Ser Val Glu Val Ser Cys Lys Ala Ser Gly Tyr Thr Phe
              20                  25

<210> SEQ ID NO 323
<211> LENGTH: 11
<212> TYPE: PRT
<213> ORGANISM: Artificial sequence
<220> FEATURE:
<223> OTHER INFORMATION: Synthetic construct

<400> SEQUENCE: 323

Trp Val Arg Gln Ala Pro Gly Gln Gly Leu Asp
1               5                   10

<210> SEQ ID NO 324
<211> LENGTH: 37
<212> TYPE: PRT
<213> ORGANISM: Artificial sequence
<220> FEATURE:
<223> OTHER INFORMATION: Synthetic construct

<400> SEQUENCE: 324

Tyr Ala Gln Asn Phe Lys Gly Arg Val Thr Met Thr Arg Asp Thr Ser
1               5                   10                  15

Ile Ser Thr Ala Tyr Leu Glu Leu Arg Ser Leu Thr Ser Asp Asp Thr
              20                  25                  30

Ala Val Tyr Phe Cys
      35

<210> SEQ ID NO 325
<211> LENGTH: 12
<212> TYPE: PRT
<213> ORGANISM: Artificial sequence
<220> FEATURE:
<223> OTHER INFORMATION: Synthetic construct

<400> SEQUENCE: 325

Lys Trp Gly Gln Gly Thr Leu Leu Thr Val Ser Ser
```

-continued

```
1               5                   10
```

<210> SEQ ID NO 326
<211> LENGTH: 29
<212> TYPE: PRT
<213> ORGANISM: Artificial sequence
<220> FEATURE:
<223> OTHER INFORMATION: Synthetic construct

<400> SEQUENCE: 326

```
Glu Val Gln Leu Val Gln Ser Gly Ala Glu Val Lys Lys Pro Gly Ala
1               5                   10                  15

Ser Val Glu Val Ser Cys Lys Ala Ser Gly Tyr Thr Phe
            20                  25
```

<210> SEQ ID NO 327
<211> LENGTH: 11
<212> TYPE: PRT
<213> ORGANISM: Artificial sequence
<220> FEATURE:
<223> OTHER INFORMATION: Synthetic construct

<400> SEQUENCE: 327

```
Trp Val Arg Gln Ala Pro Gly Gln Gly Leu Asp
1               5                   10
```

<210> SEQ ID NO 328
<211> LENGTH: 37
<212> TYPE: PRT
<213> ORGANISM: Artificial sequence
<220> FEATURE:
<223> OTHER INFORMATION: Synthetic construct

<400> SEQUENCE: 328

```
Tyr Ala Gln Asn Phe Lys Gly Arg Val Thr Met Thr Arg Asp Thr Ser
1               5                   10                  15

Ile Ser Thr Ala Tyr Leu Glu Leu Arg Ser Leu Thr Ser Asp Asp Thr
            20                  25                  30

Ala Val Tyr Phe Cys
        35
```

<210> SEQ ID NO 329
<211> LENGTH: 12
<212> TYPE: PRT
<213> ORGANISM: Artificial sequence
<220> FEATURE:
<223> OTHER INFORMATION: Synthetic construct

<400> SEQUENCE: 329

```
Lys Trp Gly Gln Gly Thr Met Leu Thr Val Ser Ser
1               5                   10
```

<210> SEQ ID NO 330
<211> LENGTH: 29
<212> TYPE: PRT
<213> ORGANISM: Artificial sequence
<220> FEATURE:
<223> OTHER INFORMATION: Synthetic construct

<400> SEQUENCE: 330

```
Glu Val Gln Leu Val Gln Ser Gly Ala Glu Val Lys Lys Pro Gly Ala
1               5                   10                  15

Ser Val Glu Val Ser Cys Lys Ala Ser Gly Tyr Thr Phe
            20                  25
```

-continued

<210> SEQ ID NO 331
<211> LENGTH: 11
<212> TYPE: PRT
<213> ORGANISM: Artificial sequence
<220> FEATURE:
<223> OTHER INFORMATION: Synthetic construct

<400> SEQUENCE: 331

Trp Val Arg Gln Ala Pro Gly Gln Gly Leu Asp
1               5                   10

<210> SEQ ID NO 332
<211> LENGTH: 37
<212> TYPE: PRT
<213> ORGANISM: Artificial sequence
<220> FEATURE:
<223> OTHER INFORMATION: Synthetic construct

<400> SEQUENCE: 332

Tyr Ala Gln Asn Phe Lys Gly Arg Val Thr Met Thr Arg Asp Thr Ser
1               5                   10                  15

Ile Ser Thr Ala Tyr Leu Glu Leu Arg Ser Leu Thr Ser Asp Asp Thr
                20                  25                  30

Ala Val Tyr Phe Cys
        35

<210> SEQ ID NO 333
<211> LENGTH: 12
<212> TYPE: PRT
<213> ORGANISM: Artificial sequence
<220> FEATURE:
<223> OTHER INFORMATION: Synthetic construct

<400> SEQUENCE: 333

Lys Trp Gly Gln Gly Thr Met Leu Thr Val Ser Ser
1               5                   10

<210> SEQ ID NO 334
<211> LENGTH: 29
<212> TYPE: PRT
<213> ORGANISM: Artificial sequence
<220> FEATURE:
<223> OTHER INFORMATION: Synthetic construct

<400> SEQUENCE: 334

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe
                20                  25

<210> SEQ ID NO 335
<211> LENGTH: 11
<212> TYPE: PRT
<213> ORGANISM: Artificial sequence
<220> FEATURE:
<223> OTHER INFORMATION: Synthetic construct

<400> SEQUENCE: 335

Trp Val Arg Gln Ala Pro Gly Gln Gly Leu Asp
1               5                   10

<210> SEQ ID NO 336
<211> LENGTH: 37
<212> TYPE: PRT
<213> ORGANISM: Artificial sequence
<220> FEATURE:
<223> OTHER INFORMATION: Synthetic construct

<400> SEQUENCE: 336

Tyr Ala Gln Asn Phe Lys Gly Arg Val Thr Met Thr Arg Asp Thr Ser
1               5                   10                  15

Ile Ser Thr Ala Tyr Leu Glu Leu Arg Ser Leu Thr Ser Asp Asp Thr
            20                  25                  30

Ala Val Tyr Phe Cys
        35

<210> SEQ ID NO 337
<211> LENGTH: 12
<212> TYPE: PRT
<213> ORGANISM: Artificial sequence
<220> FEATURE:
<223> OTHER INFORMATION: Synthetic construct

<400> SEQUENCE: 337

Lys Trp Gly Gln Gly Thr Met Leu Thr Val Ser Ser
1               5                   10

<210> SEQ ID NO 338
<211> LENGTH: 28
<212> TYPE: PRT
<213> ORGANISM: Artificial sequence
<220> FEATURE:
<223> OTHER INFORMATION: Synthetic construct

<400> SEQUENCE: 338

Glu Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp
            20                  25

<210> SEQ ID NO 339
<211> LENGTH: 9
<212> TYPE: PRT
<213> ORGANISM: Artificial sequence
<220> FEATURE:
<223> OTHER INFORMATION: Synthetic construct

<400> SEQUENCE: 339

Gln Gln His Pro Gly Lys Ala Pro Lys
1               5

<210> SEQ ID NO 340
<211> LENGTH: 33
<212> TYPE: PRT
<213> ORGANISM: Artificial sequence
<220> FEATURE:
<223> OTHER INFORMATION: Synthetic construct

<400> SEQUENCE: 340

Ser Gly Val Ser Asn Arg Phe Ser Gly Ser Lys Ser Gly Asn Thr Ala
1               5                   10                  15

Ser Leu Thr Ile Ser Gly Leu Gln Ala Glu Asp Glu Ala Asp Tyr Tyr
            20                  25                  30

Cys

<210> SEQ ID NO 341
<211> LENGTH: 12
<212> TYPE: PRT
<213> ORGANISM: Artificial sequence
<220> FEATURE:
<223> OTHER INFORMATION: Synthetic construct

<400> SEQUENCE: 341

Val Phe Gly Gly Gly Thr Lys Leu Thr Val Leu Gly
1               5                   10

<210> SEQ ID NO 342
<211> LENGTH: 26
<212> TYPE: PRT
<213> ORGANISM: Artificial sequence
<220> FEATURE:
<223> OTHER INFORMATION: Synthetic construct

<400> SEQUENCE: 342

Val Leu Thr Gln Glu Pro Ser Leu Thr Val Ser Pro Gly Gly Thr Val
1               5                   10                  15

Thr Leu Thr Cys Ala Ser Ser Thr Gly Ala
            20                  25

<210> SEQ ID NO 343
<211> LENGTH: 9
<212> TYPE: PRT
<213> ORGANISM: Artificial sequence
<220> FEATURE:
<223> OTHER INFORMATION: Synthetic construct

<400> SEQUENCE: 343

Gln Gln Lys Pro Gly Gln Ala Pro Arg
1               5

<210> SEQ ID NO 344
<211> LENGTH: 33
<212> TYPE: PRT
<213> ORGANISM: Artificial sequence
<220> FEATURE:
<223> OTHER INFORMATION: Synthetic construct

<400> SEQUENCE: 344

Ser Trp Thr Pro Ala Arg Phe Ser Gly Ser Leu Leu Gly Gly Lys Ala
1               5                   10                  15

Ala Leu Thr Leu Ser Gly Val Gln Pro Glu Asp Glu Ala Glu Tyr Tyr
            20                  25                  30

Cys

<210> SEQ ID NO 345
<211> LENGTH: 11
<212> TYPE: PRT
<213> ORGANISM: Artificial sequence
<220> FEATURE:
<223> OTHER INFORMATION: Synthetic construct

<400> SEQUENCE: 345

Val Phe Gly Gly Gly Thr Lys Leu Thr Val Leu
1               5                       10

<210> SEQ ID NO 346
<211> LENGTH: 28
<212> TYPE: PRT
<213> ORGANISM: Artificial sequence
<220> FEATURE:
<223> OTHER INFORMATION: Synthetic construct

<400> SEQUENCE: 346

Glu Ser Val Leu Thr Gln Pro Pro Ser Ile Ser Ala Ala Pro Gly Gln

```
1               5               10              15

Arg Val Thr Ile Pro Cys Ser Gly Ser Ser Ser Asp
            20              25

<210> SEQ ID NO 347
<211> LENGTH: 9
<212> TYPE: PRT
<213> ORGANISM: Artificial sequence
<220> FEATURE:
<223> OTHER INFORMATION: Synthetic construct

<400> SEQUENCE: 347

Gln Gln Leu Pro Gly Ala Ala Pro Lys
1               5

<210> SEQ ID NO 348
<211> LENGTH: 33
<212> TYPE: PRT
<213> ORGANISM: Artificial sequence
<220> FEATURE:
<223> OTHER INFORMATION: Synthetic construct

<400> SEQUENCE: 348

Ser Gly Ile Pro Asp Arg Phe Ser Gly Ser Lys Ser Gly Thr Ser Ala
1               5               10              15

Ser Leu Gly Ile Thr Gly Leu Gln Thr Gly Asp Glu Ala Asp Tyr Tyr
            20              25              30

Cys

<210> SEQ ID NO 349
<211> LENGTH: 12
<212> TYPE: PRT
<213> ORGANISM: Artificial sequence
<220> FEATURE:
<223> OTHER INFORMATION: Synthetic construct

<400> SEQUENCE: 349

Phe Phe Gly Gly Gly Thr Lys Val Thr Val Leu Gly
1               5               10

<210> SEQ ID NO 350
<211> LENGTH: 28
<212> TYPE: PRT
<213> ORGANISM: Artificial sequence
<220> FEATURE:
<223> OTHER INFORMATION: Synthetic construct

<400> SEQUENCE: 350

Glu Ser Val Leu Thr Gln Pro Pro Ser Val Ser Ala Ala Pro Gly Gln
1               5               10              15

Lys Val Thr Ile Ser Cys Ser Gly Ser Ser Ser Asn
            20              25

<210> SEQ ID NO 351
<211> LENGTH: 9
<212> TYPE: PRT
<213> ORGANISM: Artificial sequence
<220> FEATURE:
<223> OTHER INFORMATION: Synthetic construct

<400> SEQUENCE: 351

Gln Gln Leu Pro Gly Thr Ala Pro Lys
1               5
```

```
<210> SEQ ID NO 352
<211> LENGTH: 33
<212> TYPE: PRT
<213> ORGANISM: Artificial sequence
<220> FEATURE:
<223> OTHER INFORMATION: Synthetic construct

<400> SEQUENCE: 352

Ser Gly Ile Pro Asp Arg Phe Ser Gly Ser Lys Ser Gly Thr Ser Ala
1               5                   10                  15

Thr Leu Gly Ile Thr Gly Leu Gln Thr Gly Asp Glu Ala Gly Tyr Tyr
            20                  25                  30

Cys

<210> SEQ ID NO 353
<211> LENGTH: 12
<212> TYPE: PRT
<213> ORGANISM: Artificial sequence
<220> FEATURE:
<223> OTHER INFORMATION: Synthetic construct

<400> SEQUENCE: 353

Val Phe Gly Gly Gly Thr Lys Leu Thr Val Leu Gly
1               5                   10

<210> SEQ ID NO 354
<211> LENGTH: 28
<212> TYPE: PRT
<213> ORGANISM: Artificial sequence
<220> FEATURE:
<223> OTHER INFORMATION: Synthetic construct

<400> SEQUENCE: 354

Glu Ser Val Leu Thr Gln Pro Pro Ser Val Ser Ala Ala Pro Gly Gln
1               5                   10                  15

Lys Val Thr Met Ser Cys Ser Gly Ser Thr Ser Asn
            20                  25

<210> SEQ ID NO 355
<211> LENGTH: 9
<212> TYPE: PRT
<213> ORGANISM: Artificial sequence
<220> FEATURE:
<223> OTHER INFORMATION: Synthetic construct

<400> SEQUENCE: 355

Gln His Leu Pro Gly Thr Ala Pro Lys
1               5

<210> SEQ ID NO 356
<211> LENGTH: 33
<212> TYPE: PRT
<213> ORGANISM: Artificial sequence
<220> FEATURE:
<223> OTHER INFORMATION: Synthetic construct

<400> SEQUENCE: 356

Ser Gly Ile Pro Asp Arg Phe Ser Gly Ser Lys Ser Gly Thr Ser Ala
1               5                   10                  15

Thr Leu Gly Ile Thr Gly Leu Gln Thr Gly Asp Glu Ala Asp Tyr Tyr
            20                  25                  30

Cys

<210> SEQ ID NO 357
```

-continued

```
<211> LENGTH: 12
<212> TYPE: PRT
<213> ORGANISM: Artificial sequence
<220> FEATURE:
<223> OTHER INFORMATION: Synthetic construct

<400> SEQUENCE: 357

Val Phe Gly Gly Gly Thr Lys Leu Thr Val Leu Gly
1               5                   10

<210> SEQ ID NO 358
<211> LENGTH: 28
<212> TYPE: PRT
<213> ORGANISM: Artificial sequence
<220> FEATURE:
<223> OTHER INFORMATION: Synthetic construct

<400> SEQUENCE: 358

Glu Ala Val Val Thr Gln Pro Pro Ser Ala Ser Gly Thr Pro Gly Gln
1               5                   10                  15

Gly Val Thr Ile Ser Cys Ser Gly Ser Ser Ser Asn
            20                  25

<210> SEQ ID NO 359
<211> LENGTH: 9
<212> TYPE: PRT
<213> ORGANISM: Artificial sequence
<220> FEATURE:
<223> OTHER INFORMATION: Synthetic construct

<400> SEQUENCE: 359

Gln Gln Leu Pro Gly Thr Ala Pro Lys
1               5

<210> SEQ ID NO 360
<211> LENGTH: 33
<212> TYPE: PRT
<213> ORGANISM: Artificial sequence
<220> FEATURE:
<223> OTHER INFORMATION: Synthetic construct

<400> SEQUENCE: 360

Ser Gly Val Pro Asp Arg Phe Ser Gly Ser Lys Ser Ala Thr Ser Ala
1               5                   10                  15

Ser Leu Ala Ile Ser Gly Leu Arg Ser Glu Asp Glu Ala Asp Tyr Tyr
            20                  25                  30

Cys

<210> SEQ ID NO 361
<211> LENGTH: 12
<212> TYPE: PRT
<213> ORGANISM: Artificial sequence
<220> FEATURE:
<223> OTHER INFORMATION: Synthetic construct

<400> SEQUENCE: 361

Val Phe Gly Thr Gly Thr Lys Leu Thr Val Leu Gly
1               5                   10
```